(12) United States Patent
Hölder et al.

(10) Patent No.: US 9,387,204 B2
(45) Date of Patent: Jul. 12, 2016

(54) FUSED BICYCLIC IMIDAZOLES

(71) Applicant: BAYER INTELLECTUAL PROPERTY GmbH, Monheim (DE)

(72) Inventors: Swen Hölder, London (GB); Armin Zülch, Schriesheim (DE); Thomas Bär, Reichenau (DE); Thomas Maier, Stockach (DE); Astrid Zimmermann, Constance (DE); Thomas Beckers, Constance (DE); Volker Gekeler, Constance (DE); Hemant Joshi, Navi Mumbai (IN); Yogesh Munot, Providence, RI (US); Umesh Bhise, Ahmednagar (IN); Sunil Chavan, Nashik (IN); Sachin Shivatare, Pune (IN); Sarvesh Patel, Nashik (IN); Vikas Gore, Ahmednagar (IN)

(73) Assignee: Bayer Intellectual Property GmbH, Monheim (DE)

( * ) Notice: Subject to any disclaimer, the term of this patent is extended or adjusted under 35 U.S.C. 154(b) by 0 days.

(21) Appl. No.: 14/090,367

(22) Filed: Nov. 26, 2013

(65) Prior Publication Data
US 2014/0088110 A1 Mar. 27, 2014

Related U.S. Application Data

(62) Division of application No. 12/191,706, filed on Aug. 14, 2008, now Pat. No. 8,592,591.

(30) Foreign Application Priority Data

Aug. 14, 2007 (IN) .......................... 1573/MUM/2007
Oct. 18, 2007 (EP) ...................................... 07118733

(51) Int. Cl.
| | |
|---|---|
| C07D 487/04 | (2006.01) |
| C07D 401/10 | (2006.01) |
| A61K 31/519 | (2006.01) |
| A61P 35/00 | (2006.01) |
| A61K 31/454 | (2006.01) |
| C07D 471/04 | (2006.01) |
| C07D 498/04 | (2006.01) |
| C07D 513/04 | (2006.01) |
| A61K 31/4545 | (2006.01) |
| A61K 31/5025 | (2006.01) |
| A61K 45/06 | (2006.01) |
| C07D 417/04 | (2006.01) |

(52) U.S. Cl.
CPC ............ *A61K 31/454* (2013.01); *A61K 31/4545* (2013.01); *A61K 31/5025* (2013.01); *A61K 31/519* (2013.01); *A61K 45/06* (2013.01); *C07D 401/10* (2013.01); *C07D 417/04* (2013.01); *C07D 471/04* (2013.01); *C07D 487/04* (2013.01); *C07D 498/04* (2013.01); *C07D 513/04* (2013.01)

(58) Field of Classification Search
CPC .. C07D 487/04; C07D 401/10; A61K 31/519; A61K 45/06
USPC ................................ 544/282, 281; 514/259.1
See application file for complete search history.

(56) References Cited

U.S. PATENT DOCUMENTS 8,592,591 B2 * 11/2013 Holder et al. ................. 546/121

OTHER PUBLICATIONS

Pyne et al. Cancer Res 2011;71:6576-6582.*
Ferrara, N, Oncology, 69 Suppl. 3, 11-16, 2005.*
Jain et al., Nature Clinical Practice Oncology, 3(1), 24-40, 2006.*
Qiu Y. Oncogene 19, 5651-5661, 2000.*
Gautschi et al., Clin. Cancer Res., 14(6), 1639-1648, 2008.*
Mountzios et al., Cancer Treatments Reviews, 34, 175-182, 2008.*

* cited by examiner

*Primary Examiner* — Venkataraman Balasubramanian

(57) ABSTRACT

Compounds of formula (I)

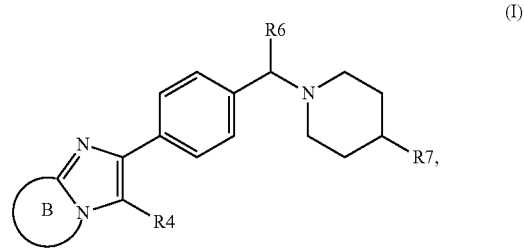

a tautomer or stereoisomer thereof, or a salt thereof, wherein ring B and the imidazole to which it is fused, R4, R6 and R7 have the meanings as given in the description and the claims, are effective inhibitors of the Pi3K/Akt pathway.

12 Claims, No Drawings

FUSED BICYCLIC IMIDAZOLES

FIELD OF APPLICATION OF THE INVENTION

The invention relates to fused imidazole compounds, which are used in the pharmaceutical industry for the manufacture of pharmaceutical compositions.

KNOWN TECHNICAL BACKGROUND

Cancer is the second most prevalent cause of death in the United States, causing 450,000 deaths per year. While substantial progress has been made in identifying some of the likely environmental and hereditary causes of cancer, there is a need for additional therapeutic modalities that target cancer and related diseases. In particular there is a need for therapeutic methods for treating diseases associated with dysregulated growth/proliferation.

Cancer is a complex disease arising after a selection process for cells with acquired functional capabilities like enhanced survival/resistance towards apoptosis and a limitless proliferative potential. Thus, it is preferred to develop drugs for cancer therapy addressing distinct features of established tumors.

One pathway that has been shown to mediate important survival signals for mammalian cells comprises receptor tyrosine kinases like platelet-derived growth factor receptor (PDGF-R), human epidermal growth factor 2/3 receptor (HER2/3), or the insulin-like growth factor 1 receptor (IGF-1R). After activation the respectives by ligand, these receptors activate the phoshatidylinositol 3-kinase (Pi3K)/Akt pathway. The phoshatidylinositol 3-kinase (Pi3K)/Akt protein kinase pathway is central to the control of cell growth, proliferation and survival, driving progression of tumors. Therefore within the class of serine-threonine specific signalling kinases, Akt (protein kinase B; PKB) with the isoenzmyes Akt1 (PKBα), Akt2 (PKB β) and Akt3 (PKB γ) is of high interest for therapeutic intervention. Akt is mainly activated in a Pi3-kinase dependent manner and the activation is regulated through the tumor suppressor PTEN (phosphatase and tensin homolog), which works essentially as the functional antagonist of Pi3K.

The Pi3K/Akt pathway regulates fundamental cellular functions (e.g. transcription, translation, growth and survival), and is implicated in human diseases including diabetes and cancer. The pathway is frequently overactivated in a wide range of tumor entities like breast and prostate carcinomas. Upregulation can be due to overexpression or constitutively activation of receptor tyrosine kinases (e.g. EGFR, HER2/3), which are upstream and involved in its direct activation, or gain- or loss-of-function mutants of some of the components like loss of PTEN. The pathway is targeted by genomic alterations including mutation, amplification and rearrangement more frequently than any other pathway in human cancer, with the possible exception of the p53 and retinoblastoma pathways. The alterations of the Pi3K/Akt pathway trigger a cascade of biological events, that drive tumor progression, survival, angiogenesis and metastasis.

Activation of Akt kinases promotes increased nutrient uptake, converting cells to a glucose-dependent metabolism that redirects lipid precursors and amino acids to anabolic processes that support cell growth and proliferation. These metabolic phenotype with overactivated Akt lead to malignancies that display a metabolic conversion to aerobic glycolysis (the Warburg effect). In that respect the Pi3K/Akt pathway is discussed to be central for survival despite unfavourable growth conditions such as glucose depletion or hypoxia.

A further aspect of the activated PI3K/Akt pathway is to protect cells from programmed cell death ("apoptosis") and is hence considered to transduce a survival signal. By acting as a modulator of anti-apoptotic signalling in tumor cells, the Pi3K/Akt pathway, particular Akt itself is a target for cancer therapy. Activated Akt phosphorylates and regulates several targets, e.g. BAD, GSK3 or FKHRL1, that affect different signalling pathways like cell survival, protein synthesis or cell movement. This Pi3K/Akt pathway also plays a major part in resistance of tumor cells to conventional anti-cancer therapies. Blocking the Pi3K/Akt pathway could therefore simultaneously inhibit the proliferation of tumor cells (e.g. via the inhibition of the metabolic effect) and sensitize towards pro-apoptotic agents.

Akt inhibition selectively sensitized tumor cells to apoptotic stimuli like Trail, Campthothecin and Doxorubicin. Dependent on the genetic background/molecular apperations of tumors, Akt inhibitors might induce apoptotic cell death in monotherapy as well.

In the European patent EP1268478 phenyl-substituted imidazopyridines are disclosed as H3-antagonists for treating diseases in the central nervous system. In the International patent application WO2005014598 substituted imidazopyrimidines are disclosed for the treatment of cancer. In the International patent application WO2007025090 substituted imidazopyridazines are disclosed for the treatment of cancer. In the International patent applications WO2004096131, WO2005100344, WO2006036395, WO2006065601, WO2006091395 and WO2006135627 Akt inhibitors are described.

DESCRIPTION OF THE INVENTION

It has now been found that the fused imidazole compounds, which are described in detail below, have surprising and advantageous properties.

In accordance with a first aspect, the invention relates to compounds of formula (I)

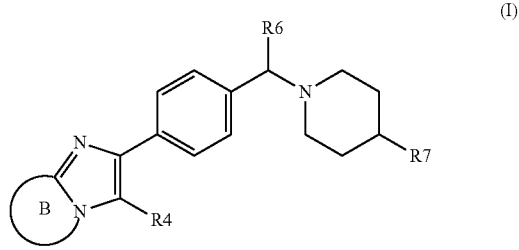

wherein
ring B and the imidazole to which it is fused form a ring system selected from

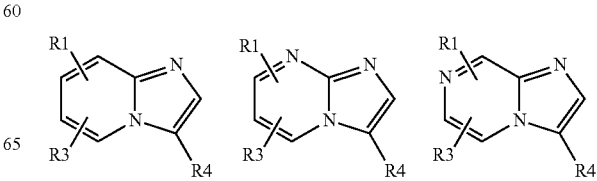

-continued

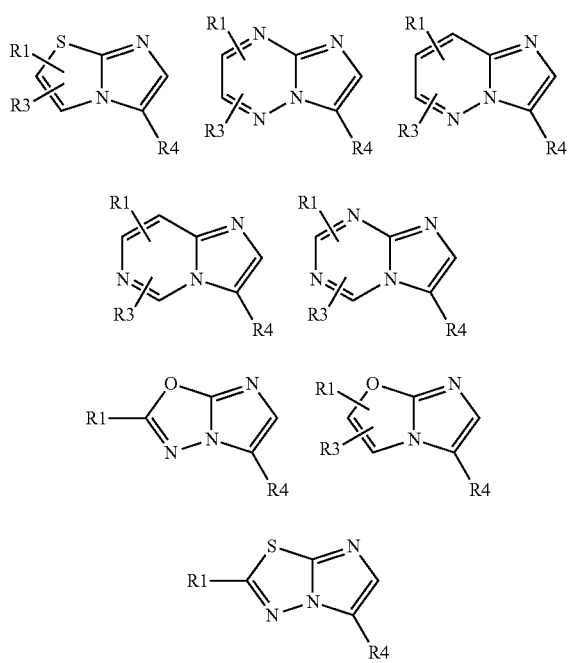

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10

R2 is hydrogen, 1-4C-alkyl or 3-7C-cycloalkyl,

R3 is hydrogen, 1-4C-alkyl or halogen,

R4 is phenyl substituted by R5, unsubstituted phenyl, thienyl, pyridinyl, thiazolyl or oxazolyl, R5 is 1-4C-alkyl, halogen or 1-4C-alkoxy, R6 is hydrogen or 1-4C-alkyl, R7 is -W-Y, W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8, R8 is 1-4C-alkyl or 3-7C-cycloalkyl, Y is phenyl or a monocyclic 5- or 6-membered heteroaryl comprising 1 nitrogen atom and optionally 1 or 2 further heteroatoms independently selected from oxygen, nitrogen, sulphur
and wherein the heteroaryl is optionally substituted by R9, R9 is 1-4C-alkyl, 1-4C-alkoxy or halogen, R10 is hydrogen or 1-4C-alkyl, or a salt, particularly a pharmaceutically acceptable salt, a tautomer, or a stereoisomer of said compound, or a salt, particularly a pharmaceutically acceptable salt, of said tautomer or said stereoisomer.

In accordance with a second aspect, the invention relates to compounds of formula (I)

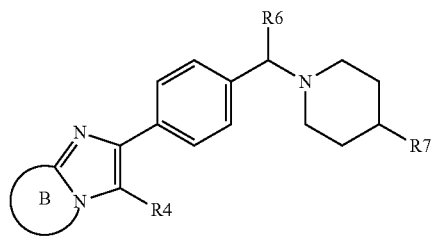

wherein ring B and the imidazole to which it is fused form a ring system selected from

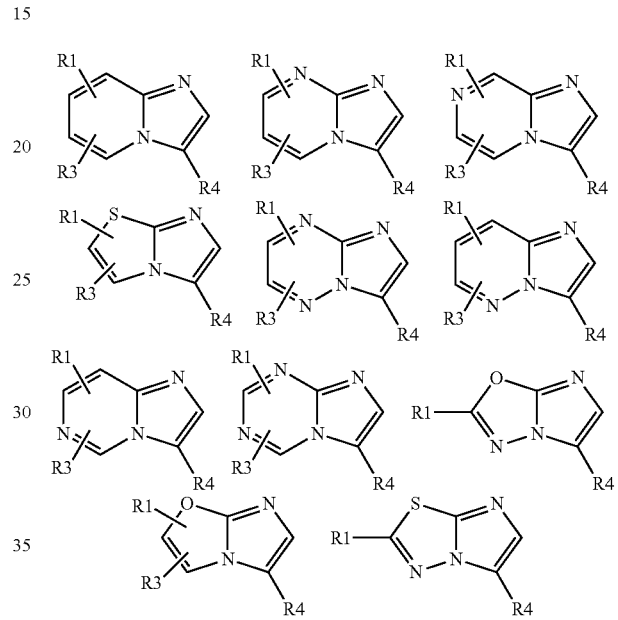

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10

R2 is hydrogen, 1-4C-alkyl or 3-7C-cycloalkyl,

R3 is hydrogen, 1-4C-alkyl or halogen,

R4 is phenyl substituted by R5, unsubstituted phenyl, thienyl, pyridinyl, thiazolyl or oxazolyl, R5 is 1-4C-alkyl, halogen or 1-4C-alkoxy, R6 is hydrogen or 1-4C-alkyl, R7 is -W-Y, W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8, R8 is 1-4C-alkyl or 3-7C-cycloalkyl, Y is a monocyclic 5- or 6-membered heteroaryl comprising 1 nitrogen atom and optionally 1 or 2 further heteroatoms independently selected from oxygen, nitrogen, sulphur
and wherein the heteroaryl is optionally substituted by R9, R9 is 1-4C-alkyl, 1-4C-alkoxy or halogen, R10 is hydrogen or 1-4C-alkyl, or a salt, particularly a pharmaceutically acceptable salt, a tautomer, or a stereoisomer of said compound, or a salt, particularly a pharmaceutically acceptable salt, of said tautomer or said stereoisomer.

1-4C-Alkyl is a straight-chain or branched alkyl group having 1 to 4 carbon atoms. Examples are methyl, ethyl, n-propyl, iso-propyl, n-butyl, iso-butyl, sec-butyl and tert-butyl.

Mono- or di-1-4C-alkylamino radicals contain in addition to the nitrogen atom, one or two of the abovementioned 1-4C-alkyl radicals. Examples are the methylamino, the ethylamino, the isopropylamino, the dimethylamino, the diethylamino and the diisopropylamino radical.

Mono- or di-1-4C-alkylaminocarbonyl radicals contain in addition to the carbonyl group one of the abovementioned mono- or di-1-4C-alkylamino radicals. Examples are the N-methylaminocarbonyl, the N,N-dimethylaminocarbonyl, the N-ethylaminocarbonyl, the N-propylaminocarbonyl, the N,N-diethylaminocarbonyl and the N-isopropylaminocarbonyl.

Halogen within the meaning of the present invention is iodine, or particularly bromine, chlorine and fluorine.

1-4C-Alkoxy represents radicals, which in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy, ethoxy and methoxy radicals.

3-7C-Cycloalkyl stands for cyclopropyl, cyclobutyl, cyclopentyl, cyclohexyl or cycloheptyl.

3-7C-Cycloalkyloxy stands for cyclopropyloxy, cyclobutyloxy, cyclopentyloxy, cyclohexyloxy or cycloheptyloxy.

2-4C-Alkenyl is a straight chain or branched alkenyl radical having 2 to 4 carbon atoms. Examples are the but-2-enyl, but-3-enyl (homoallyl), prop-1-enyl, prop-2-enyl (allyl) and the ethenyl (vinyl) radicals.

2-4C-Alkynyl is a straight chain or branched alkynyl radical having 2 to 4 carbon atoms. Examples are the but-2-ynyl, but-3-ynyl (homopropargyl), prop-1-ynyl, 1-methylprop-2-ynyl (1-methylpropargyl), prop-2-ynyl (propargyl) and the ethynyl radicals.

The term "monocyclic 5- or 6-membered heteroaryl" comprised without being restricted thereto, the 5-membered heteroaryl radicals furyl, thienyl, pyrrolyl, oxazolyl, isoxazolyl, thiazolyl, isothiazolyl, imidazolyl, pyrazolyl, triazolyl (1,2,4-triazolyl, 1,3,4-triazolyl or 1,2,3-triazolyl), thiadiazolyl (1,3,4-thiadiazolyl, 1,2,5-thiadiazolyl, 1,2,3-thiadiazolyl or 1,2,4-thiadiazolyl) and oxadiazolyl (1,3,4-oxadiazolyl, 1,2,5-oxadiazolyl, 1,2,3-oxadiazolyl or 1,2,4-oxadiazolyl), as well as the 6-membered heteroaryl radicals pyridinyl, pyrimidinyl, pyrazinyl and pyridazinyl. Preferred 5- or 6-membered heteroaryl radicals are furanyl, thienyl, pyrrolyl, thiazolyl, oxazolyl, thiadiazolyl, oxadiazolyl, pyridinyl, pyrimidinyl, pyrimidinyl, pyrazinyl or pyridazinyl. More preferred 5- or 6-membered heteroaryl radicals are furan-2-yl, thien-2-yl, pyrrol-2-yl, thiazolyl, oxazolyl, 1,3,4-thiadiazolyl, 1,3,4-oxadiazolyl, pyridin-2-yl, pyridin-4-yl, pyrimidin-2-yl, pyrimidin-4-yl, pyrazin-2-yl or pyridazin-3-yl.

The term "monocyclic 5-membered heteroarylene" is a divalent radical in which arbitrary one hydrogen atom is eliminated from the above described "heteroaryl" and may include, without being restricted thereto, the 5-membered heteroaryl radicals furylene, thienylene, pyrrolylene, oxazolylene, isoxazolylene, thiazolylene, isothiazolylene, imidazolylene, pyrazolylene, triazolylene (1,2,4-triazolylene, 1,3,4-triazolylene or 1,2,3-triazolylene), thiadiazolylene (1,3,4-thiadiazolylene, 1,2,5-thiadiazolylene, 1,2,3-thiadiazolylene or 1,2,4-thiadiazolylene) and oxadiazolylene (1,3,4-oxadiazolylene, 1,2,5-oxadiazolylene, 1,2,3-oxadiazolylene or 1,2,4-oxadiazolylene). Preferred 5-membered heteroaryl radicals are triazolylene, pyrazolylene, oxadiazolylene or imidazolylene. More preferred 5-membered heteroaryl radicals are 1,2,4-triazolylene, pyrazolylene, 1,2,4-oxadiazolylene or imidazolylene.

In general and unless otherwise mentioned, the heteroarylic or heteroarylenic radicals include all the possible isomeric forms thereof, e.g. the positional isomers thereof. Thus, for some illustrative non-restricting example, the term pyridinyl or pyridinylene includes pyridin-2-yl, pyridin-2-ylene, pyridin-3-yl, pyridin-3-ylene, pyridin-4-yl and pyridin-4-ylene; or the term thienyl or thienylene includes thien-2-yl, thien-2-ylene, thien-3-yl and thien-3-ylene.

Constituents which are optionally substituted as stated herein, may be substituted, unless otherwise noted, at any possible position. Analogously it is being understood that it is possible for any heteroaryl group if chemically suitable that said heteroaryl group may be attached to the rest of the molecule via any suitable atom.

The heteroarylic or heteroarylenic groups mentioned herein may be substituted by their given substituents or parent molecular groups, unless otherwise noted, at any possible position, such as e.g. at any substitutable ring carbon or ring nitrogen atom.

Unless otherwise noted, rings containing quaternizable amino- or imino-type ring nitrogen atoms (—N=) may be preferably not quaternized on these amino- or imino-type ring nitrogen atoms by the mentioned substituents or parent molecular groups.

Unless otherwise noted, any heteroatom of a heteroarylic or heteroarylenic ring with unsatisfied valences mentioned herein is assumed to have the hydrogen atom(s) to satisfy the valences.

When any variable occurs more than one time in any constituent, each definition is independent.

In another embodiment of the above-mentioned first or second aspect, the invention relates to compounds of formula (I), wherein ring B and the imidazole to which it is fused form a ring system selected from

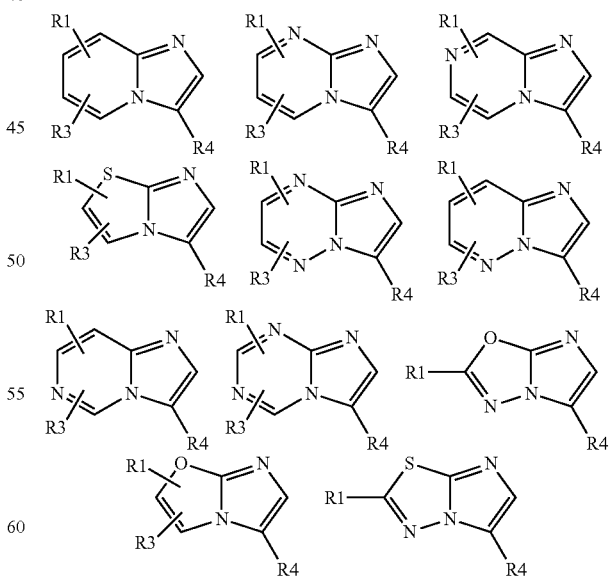

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-

4C-alkylamino, mono- or di-1-4C-alkylaminocarbonyl, —C(NH)NH2, —C(O)NH2 or

R2 is hydrogen, 1-4C-alkyl or 3-7C-cycloalkyl,

R3 is hydrogen, 1-4C-alkyl or halogen,

R4 is phenyl substituted by R5, unsubstituted phenyl, thienyl, pyridinyl, thiazolyl or oxazolyl, R5 is 1-4C-alkyl, halogen or 1-4C-alkoxy, R6 is hydrogen or 1-4C-alkyl, R7 is -W-Y, W is a monocyclic 5-membered heteroarylene comprising 1 nitrogen atom and optionally 1 or 2 further heteroatoms independently selected from oxygen, nitrogen and sulphur, and wherein the heteroarylene is optionally substituted by R8, R8 is 1-4C-alkyl or 3-7C-cycloalkyl, Y is a monocyclic 5- or 6-membered heteroaryl comprising 1 nitrogen atom and optionally 1 or 2 further heteroatoms independently selected from oxygen, nitrogen, sulphur and wherein the heteroaryl is optionally substituted by R9, R9 is 1-4C-alkyl or halogen, or a salt, as well as the stereoisomer and salt of the stereoisomer thereof.

In a further embodiment, the invention relates to compounds of formula (I), wherein ring B and the imidazole to which it is fused form a ring system selected from

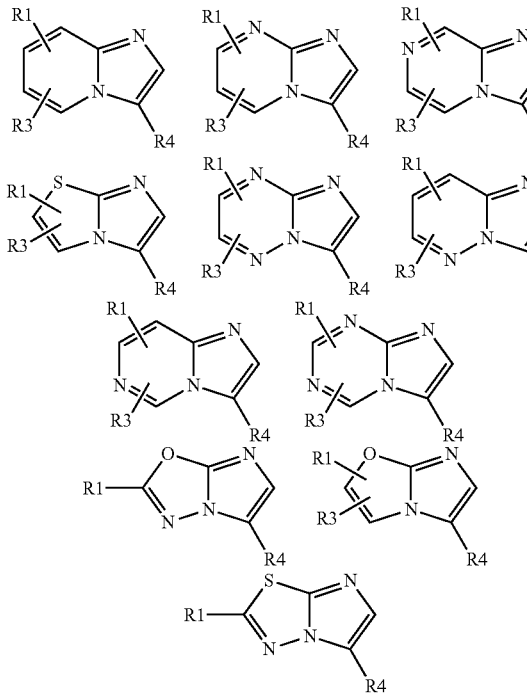

wherein

R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2 or —C(O)NH2, R2 is hydrogen, 1-4C-alkyl or 3-7C-cycloalkyl, R3 is hydrogen, R4 is phenyl substituted by R5, unsubstituted phenyl, thienyl, pyridinyl or thiazolyl, R5 is 1-4C-alkyl, halogen or 1-4C-alkoxy, R6 is hydrogen or methyl, R7 is -W-Y, W is triazolylene, pyrazolylene, oxadiazolylene or imidazolylene, each of which is optionally substituted by R8, R8 is 1-4C-alkyl or 3-7C-cycloalkyl, Y is thiazolyl, oxazolyl, thiadiazolyl, oxadiazolyl, pyridinyl, pyrimidinyl, pyrazinyl or pyridazinyl, each of which is optionally substituted by R9, R9 is 1-4C alkyl or halogen, or a salt, as well as the stereoisomer and salt of the stereoisomer thereof.

In another embodiment, the invention relates to compounds of formula (I), wherein ring B and the imidazole to which it is fused form a ring system selected from

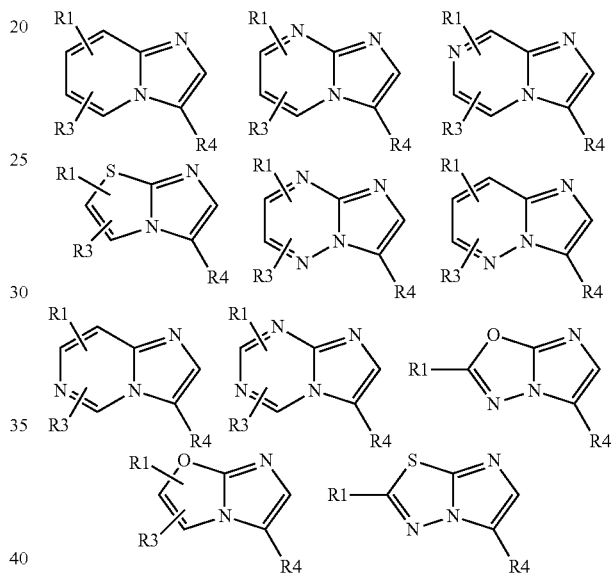

wherein

R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2 or —C(O)NH2, R2 is hydrogen, 1-4C-alkyl or 3-7C-cycloalkyl, R3 is hydrogen, R4 is phenyl substituted by R5, unsubstituted phenyl, thienyl, pyridinyl or thiazolyl, R5 is 1-4C-alkyl, halogen or 1-4C-alkoxy, R6 is hydrogen or methyl, R7 is -W-Y, W is 1,2,4-triazolylene, pyrazolylene, 1,2,4-oxadiazolylene or imidazolylene, Y is thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, or a salt as well as the stereoisomer and salt of the stereoisomer thereof.

In a further preferred embodiment, the invention relates to compounds of formula (I), wherein ring B and the imidazole to which it is fused form a ring system selected from

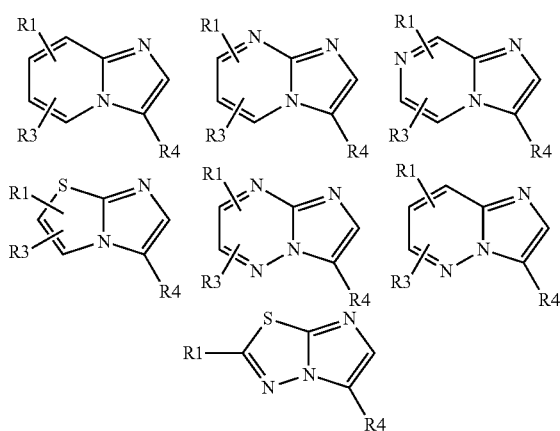

wherein
R1 is hydrogen, 1-4C-alkyl, halogen, amino, trifluoromethyl, cyano, 2-4C-alkenyl, 2-4C-alkynyl, 1-4C-alkoxy, mono- or di-1-4C-alkylamino, mono- or di-1-4C-alkylaminocarbonyl, —C(NH)NH2 or —C(O)NH2,
R3 is hydrogen,
R4 is unsubstituted phenyl or thienyl,
R6 is hydrogen,
R7 is -W-Y,
W is 1,2,4-triazolylene, pyrazolylene, 1,2,4-oxadiazolylene or imidazolylene,
Y is pyridin-2-yl, pyrimidin-2-yl, pyrimidin-4-yl, pyrazin-2-yl or pyridazin-3-yl,
or a salt thereof.

In a further preferred embodiment, the invention relates to compounds of formula (I), wherein
ring B and the imidazole to which it is fused form a ring system selected from

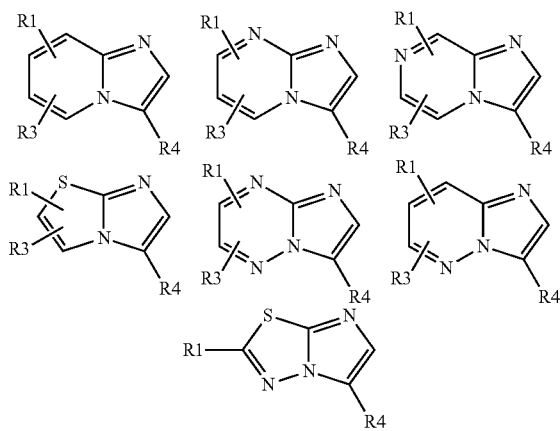

wherein
R1 is hydrogen, 1-4C-alkyl, halogen, amino, trifluoromethyl, cyano, 1-4C-alkoxy, —C(NH)NH2 or —C(O)NH2,
R3 is hydrogen,
R4 is phenyl substituted by R5, unsubstituted phenyl, thienyl, pyridinyl or thiazolyl,
R5 is 1-4C-alkyl, halogen or 1-4C-alkoxy,
R6 is hydrogen,
R7 is -W-Y,
W is 1,2,4-triazolylene, 1,2,4-oxadiazolylene or pyrazolylene,
Y is pyridin-2-yl or pyrazin-2-yl,
and the salts, as well as the stereoisomers and salts of the stereoisomers thereof In a further preferred embodiment, the invention relates to compounds of formula (I), wherein
ring B and the imidazole to which it is fused form a ring system selected from

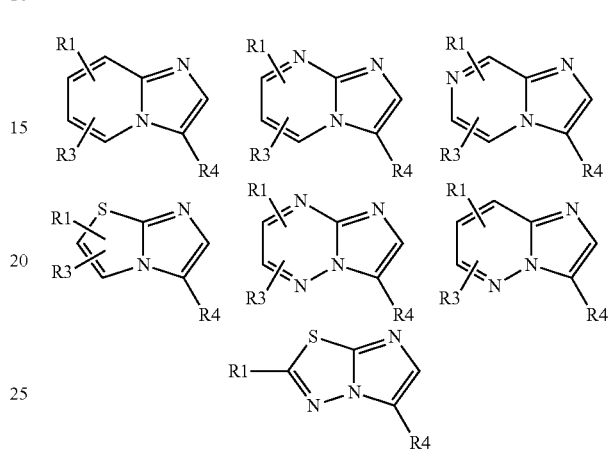

wherein
R1 is hydrogen, 1-4C-alkyl, halogen, amino, trifluoromethyl, cyano, 1-4C-alkoxy, —C(NH)NH2 or —C(O)NH2,
R3 is hydrogen,
R4 is phenyl substituted by R5, unsubstituted phenyl, thienyl, pyridinyl or thiazolyl,
R5 is 1-4C-alkyl, halogen or 1-4C-alkoxy,
R6 is hydrogen,
R7 is -W-Y,
W is 1,2,4-triazolylene, 1,2,4-oxadiazolylene or pyrazolylene,
Y is pyridin-2-yl or pyrazin-2-yl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment, the invention relates to compounds of formula (I), wherein
ring B and the imidazole to which it is fused form a ring system selected from

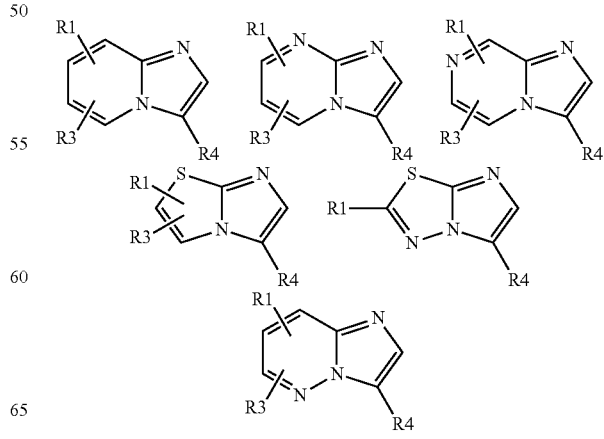

wherein
R1 is hydrogen, methyl, halogen, trifluoromethyl, cyano, methoxy, —C(NH)NH2 or —C(O)NH2,
R3 is hydrogen,
R4 is unsubstituted phenyl,
R6 is hydrogen,
R7 is -W-Y,
W is 1,2,4-triazolylene,
Y is pyridin-2-yl,
and the salts, as well as the stereoisomers and salts of the stereoisomers thereof.

In a further preferred embodiment, the invention relates to compounds of formula (I), wherein
ring B and the imidazole to which it is fused form a ring system selected from

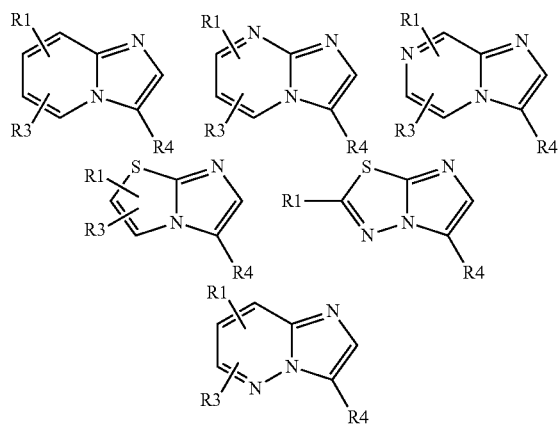

wherein
R1 is hydrogen, methyl, halogen, trifluoromethyl, cyano, methoxy, —C(NH)NH2 or —C(O)NH2,
R3 is hydrogen,
R4 is unsubstituted phenyl,
R6 is hydrogen,
R7 is -W-Y,
W is 1,2,4-triazolylene,
Y is pyridin-2-yl,
or a salt, particularly a pharmaceutically acceptable salt, a tautomer, or a stereoisomer of said compound, or a salt, particularly a pharmaceutically acceptable salt, of said tautomer or said stereoisomer.

In a further embodiment, the invention relates to compounds of formula (I), wherein
ring B and the imidazole to which it is fused form a ring system selected from

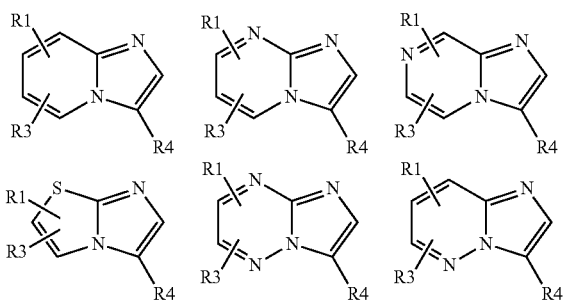

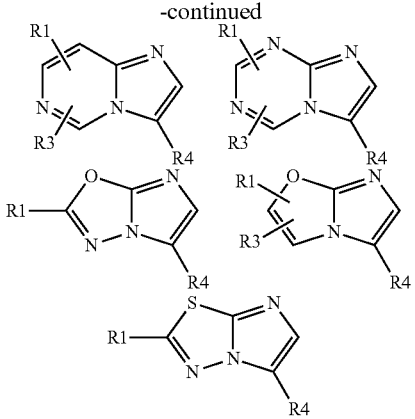

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10
R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, oxazolyl or thiazolyl,
R5 is 1-4C-alkyl, halogen or 1-4C-alkoxy,
R6 is hydrogen or methyl,
R7 is -W-Y,
W is triazolylene, pyrazolylene, oxadiazolylene or imidazolylene, each of which is optionally substituted by R8,
R8 is 1-4C-alkyl or 3-7C-cycloalkyl,
Y is phenyl, furanyl, thienyl, pyrrolyl, thiazolyl, oxazolyl, thiadiazolyl, oxadiazolyl, pyridinyl, pyrimidinyl, pyrazinyl or pyridazinyl, each of which is optionally substituted by R9,
R9 is 1-4C-alkyl, 1-4C-alkoxy or halogen,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In another embodiment, the invention relates to compounds of formula (I), wherein
ring B and the imidazole to which it is fused form a ring system selected from

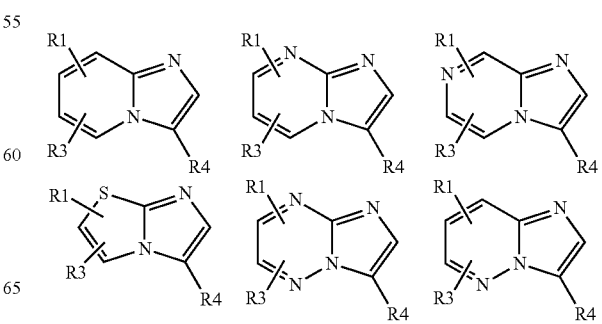

-continued wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10
R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, oxazolyl or thiazolyl,
R5 is 1-4C-alkyl, halogen or 1-4C-alkoxy,
R6 is hydrogen or methyl,
R7 is -W-Y,
W is 1,2,4-triazolylene, pyrazolylene, 1,2,4-oxadiazolylene or imidazolylene,
Y is phenyl, furan-2-yl, thien-2-yl, pyrrol-2-yl, pyridin-4-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, each of which is optionally substituted by R9,
R9 is 1-4C-alkyl, 1-4C-alkoxy or halogen,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment, the invention relates to compounds of formula (I), wherein
ring B and the imidazole to which it is fused form a ring system selected from wherein
R1 is hydrogen, 1-4C-alkyl, halogen, —SR2, amino, trifluoromethyl, cyano, 2-4C-alkenyl, 2-4C-alkynyl, 1-4C-alkoxy, mono- or di-1-4C-alkylamino, mono- or di-1-4C-alkylaminocarbonyl, —C(NH)NH2, —C(O)NH2 or —C(O)OR10

R2 is 1-4C-alkyl,
R3 is hydrogen or halogen,
R4 is phenyl substituted by R5, unsubstituted phenyl, thienyl, pyridinyl, oxazolyl or thiazolyl,
R6 is hydrogen,
R7 is -W-Y,
W is 1,2,4-triazolylene, pyrazolylene or 1,2,4-oxadiazolylene,
Y is phenyl, furan-2-yl, thien-2-yl, pyrrol-2-yl, pyridin-4-yl, thiazol-2-yl, pyridin-2-yl, pyrimidin-2-yl, pyrimidin-4-yl, pyrazin-2-yl or pyridazin-3-yl, each of which is optionally substituted by R9,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment the invention relates to compounds of formula (I), wherein ring B and the imidazole to which it is fused form a ring system selected from wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10
R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, oxazolyl or thiazolyl,
R5 is 1-4C-alkyl, halogen or 1-4C-alkoxy,
R6 is hydrogen or methyl,
R7 is -W-Y,
W is triazolylene, pyrazolylene, oxadiazolylene or imidazolylene, each of which is optionally substituted by R8,
R8 is 1-4C-alkyl or 3-7C-cycloalkyl,
Y is furanyl, thienyl, pyrrolyl, thiazolyl, oxazolyl, thiadiazolyl, oxadiazolyl, pyridinyl, pyrimidinyl, pyrazinyl or pyridazinyl, each of which is optionally substituted by R9,
R9 is 1-4C-alkyl, 1-4C-alkoxy or halogen,
R10 is hydrogen or 1-4C-alkyl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the second aspect, the invention relates to compounds of formula (I), wherein ring B and the imidazole to which it is fused form a ring system selected from

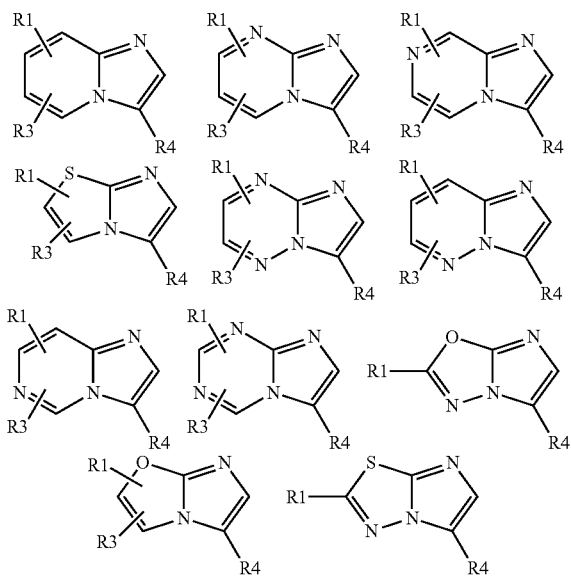

wherein

R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10

R2 is hydrogen, 1-4C-alkyl or 3-7C-cycloalkyl,

R3 is hydrogen, 1-4C-alkyl or halogen,

R4 is phenyl substituted by R5, unsubstituted phenyl, thienyl, pyridinyl, oxazolyl or thiazolyl, R5 is 1-4C-alkyl, halogen or 1-4C-alkoxy, R6 is hydrogen or methyl, R7 is -W-Y, W is 1,2,4-triazolylene, pyrazolylene, 1,2,4-oxadiazolylene or imidazolylene, Y is furan-2-yl, thien-2-yl, pyrrol-2-yl, pyridin-4-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, each of which is optionally substituted by R9, R9 is 1-4C-alkyl, 1-4C-alkoxy or halogen, R10 is hydrogen or 1-4C-alkyl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the second aspect, the invention relates to compounds of formula (I), wherein ring B and the imidazole to which it is fused form a ring system selected from

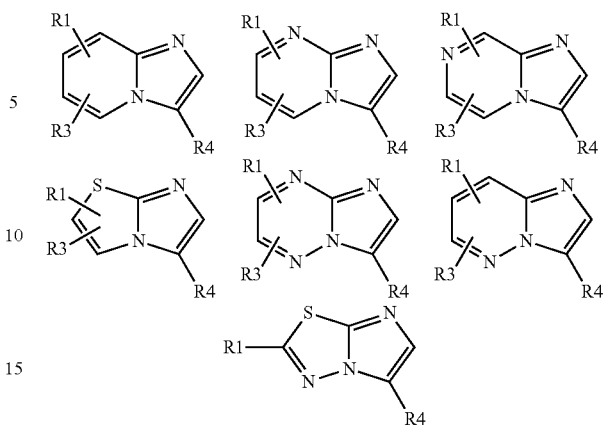

wherein

R1 is hydrogen, 1-4C-alkyl, halogen, —SR2, amino, trifluoromethyl, cyano, 2-4C-alkenyl, 2-4C-alkynyl, 1-4C-alkoxy, mono- or di-1-4C-alkylamino, mono- or di-1-4C-alkylaminocarbonyl, —C(NH)NH2, —C(O)NH2 or —C(O)OR10

R2 is 1-4C-alkyl,

R3 is hydrogen or halogen,

R4 is phenyl substituted by R5, unsubstituted phenyl, thienyl, pyridinyl, oxazolyl or thiazolyl, R6 is hydrogen, R7 is -W-Y, W is 1,2,4-triazolylene, pyrazolylene or 1,2,4-oxadiazolylene, Y is furan-2-yl, thien-2-yl, pyrrol-2-yl, pyridin-4-yl, thiazol-2-yl, pyridin-2-yl, pyrimidin-2-yl, pyrimidin-4-yl, pyrazin-2-yl or pyridazin-3-yl, each of which is optionally substituted by R9, R9 is 1-4C-alkyl, 1-4C-alkoxy or halogen, R10 is hydrogen or 1-4C-alkyl, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment, the invention relates to compounds of formula (I), wherein ring B and the imidazole to which it is fused form a ring system selected from

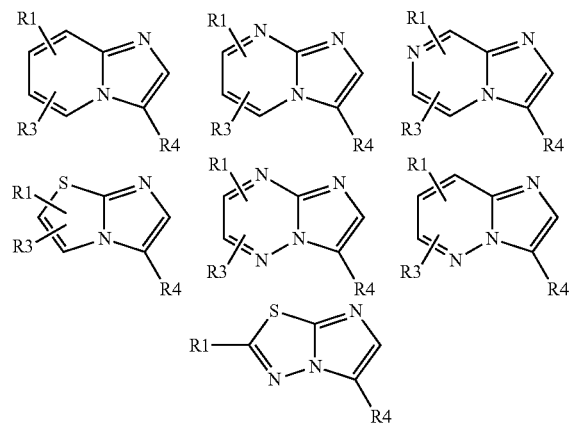

wherein
R1 is hydrogen, 1-4C-alkyl, halogen, —SR2, amino, trifluoromethyl, cyano, 1-4C-alkoxy, —C(NH)NH2, —C(O)NH2 or —C(O)OR10,
R2 is 1-4C-alkyl,
R3 is hydrogen or halogen,
R4 is phenyl substituted by R5, unsubstituted phenyl, thienyl, pyridinyl or thiazolyl,
R5 is 1-4C-alkyl, halogen or 1-4C-alkoxy,
R6 is hydrogen,
R7 is -W-Y,
W is 1,2,4-triazolylene, 1,2,4-oxadiazolylene or pyrazolylene,
Y is pyridin-2-yl or pyrazin-2-yl, each of which is optionally substituted by R9,
R9 is 1-4C-alkyl, 1-4C-alkoxy or halogen,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment, the invention relates to compounds of formula (I), wherein
ring B and the imidazole to which it is fused form a ring system selected from

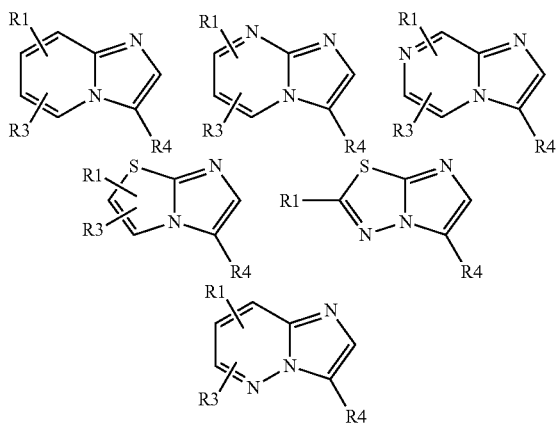

wherein
R1 is hydrogen, methyl, halogen, —SR2, trifluoromethyl, cyano, methoxy, —C(NH)NH2, —C(O)NH2 or —C(O)OR10,
R2 is 1-4C-alkyl,
R3 is hydrogen or halogen,
R4 is unsubstituted phenyl,
R6 is hydrogen,
R7 is -W-Y,
W is 1,2,4-triazolylene,
Y is pyridin-2-yl which is optionally substituted by R9,
R9 is 1-4C-alkyl, 1-4C-alkoxy or halogen,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein
ring B and the imidazole to which it is fused form a ring system selected from

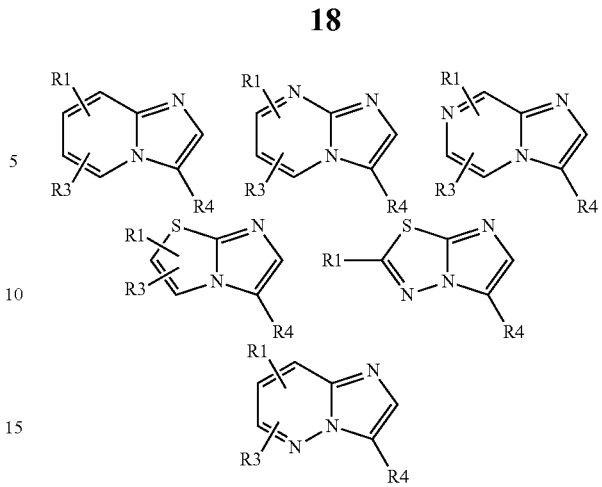

wherein
R1 is hydrogen, methyl, halogen, —SR2, trifluoromethyl, cyano, methoxy, —C(NH)NH2, —C(O)NH2 or —C(O)OR10,
R2 is 1-4C-alkyl,
R3 is hydrogen,
R4 is unsubstituted phenyl,
R6 is hydrogen,
R7 is -W-Y,
W is 1,2,4-triazolylene,
Y is pyridin-2-yl,
R10 is hydrogen or 1-4C-alkyl,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

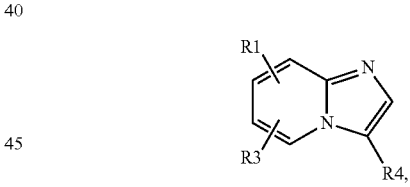

R3 is hydrogen, R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

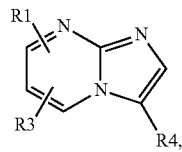

R3 is hydrogen, R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

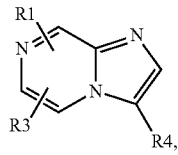

R3 is hydrogen, R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

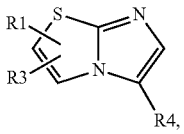

R3 is hydrogen, R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

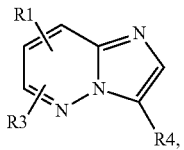

R3 is hydrogen, R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

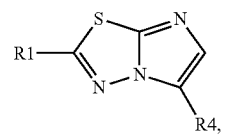

R6 is hydrogen and R1, R2, R4, R5, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

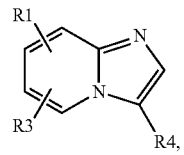

R3 is hydrogen, R6 is hydrogen, R4 is phenyl and R1, R2, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

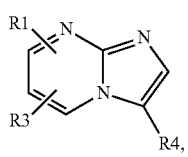

R3 is hydrogen, R6 is hydrogen, R4 is phenyl and R1, R2, R7, R8, R9, W and Y are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

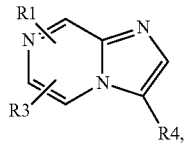

R3 is hydrogen, R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

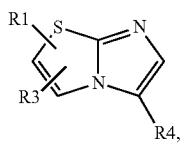

R3 is hydrogen, R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

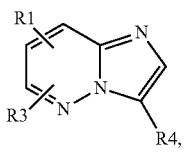

R3 is hydrogen, R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused form the following ring system

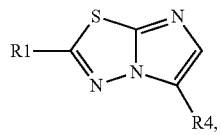

R6 is hydrogen, R4 is phenyl and R1, R2, R7, R8, R9, W and Y are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

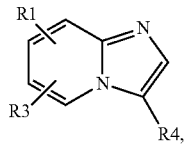

R3 is hydrogen, R6 is hydrogen, R4 is phenyl, R7 is -W-Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

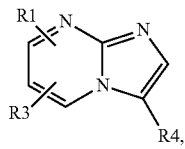

R3 is hydrogen, R6 is hydrogen, R4 is phenyl, R7 is -W-Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

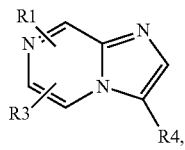

R3 is hydrogen, R6 is hydrogen, R4 is phenyl, R7 is -W-Y, W is 1,2,4-triazolylene, Y is pyridin-2-yl and R1 and R2 are as described above, or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

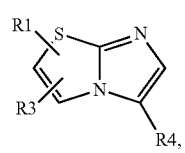

R3 is hydrogen, R6 is hydrogen, R4 is phenyl, R7 is -W-Y, W is 1,2,4-triazolylene, Y is pyridin-2-yl and R1 and R2 are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

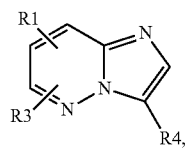

R3 is hydrogen, R6 is hydrogen, R4 is phenyl, R7 is -W-Y, W is 1,2,4-triazolylene, Y is pyridin-2-yl and R1 and R2 are as described above,
or a salt, particularly a pharmaceutically acceptable salt, a tautomer, or a stereoisomer of said compound, or a salt, particularly a pharmaceutically acceptable salt, of said tautomer or said stereoisomer.

In a further preferred embodiment of the above-mentioned first or second aspect, the invention relates to compounds of formula (I), wherein ring B and the imidazole to which it is fused is

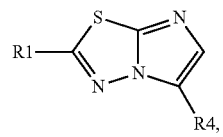

R6 is hydrogen, R4 is phenyl, R7 is -W-Y, W is 1,2,4-triazolylene, Y is pyridin-2-yl and R1 and R2 are as described above,
or a salt, particularly a pharmaceutically acceptable salt, a tautomer, or a stereoisomer of said compound, or a salt, particularly a pharmaceutically acceptable salt, of said tautomer or said stereoisomer.

Salts of the compounds according to the invention include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, salts of sulfamic acid, formates, acetates, propionates, citrates, D-gluconates, benzoates, 2-(4-hydroxybenzoyl)benzoates, butyrates, salicylates, sulfosalicylates, lactates, maleates, laurates, malates, fumarates, succinates, oxalates, malonates, pyruvates, acetoacetates, tartarates, stearates, benzensulfontes, toluenesulfonates, methanesulfonates, trifluoromethansulfonates, 3-hydroxy-2-naphthoates, benzenesulfonates, naphthalinedisulfonates, and trifluoroacetates.

Examples of salts with bases include, but are not limited to, lithium, sodium, potassium, calcium, aluminum, magnesium, titanium, meglumine, ammonium salts optionally derived from $NH_3$ or organic amines having from 1 to 16 C-atoms such as e.g. ethylamine, diethylamine, triethylamine, ethyldiisopropylamine, monoethanolamine, diethanolamine, triethanolamine, dicyclohexylamine, dimethylaminoethanol, procaine, dibenzylamine, N-methylmorpholine, arginine, lysine, ethylendiamine, N-methylpiperindine and guanidinium salts.

The salts include water-insoluble and, particularly, water-soluble salts.

According to the person skilled in the art the compounds of formula (I) according to this invention as well as their salts may contain, e.g. when isolated in crystalline form, varying amounts of solvents. Included within the scope of the invention are therefore all solvates and in particular all hydrates of the compounds of formula (I) according to this invention as well as all solvates and in particular all hydrates of the salts of the compounds of formula (I) according to this invention.

The compounds according to the invention and their salts can exist in the form of tautomers. In particular, those compounds of the invention which contain a pyrazole moiety for example can exist as a 1H tautomer, or a 2H tautomer, or even a mixture in any amount of the two tautomers, or a triazole moiety for example can exist as a 1H tautomer, a 2H tautomer, or a 4H tautomer, or even a mixture in any amount of said 1H, 2H and 4H tautomers:

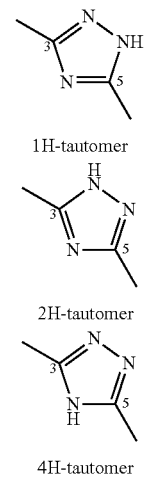

1H-tautomer 2H-tautomer 4H-tautomer

The compounds according to the invention and the salts thereof include stereoisomers. Each of the stereogenic centers present in said stereoisomers may have the absolute configuration R or the absolute configuration S (according to the rules of Cahn, Ingold and Prelog). Accordingly, the stereoisomers (1 S) and (1R) in case of a compound of formula (Ia*)

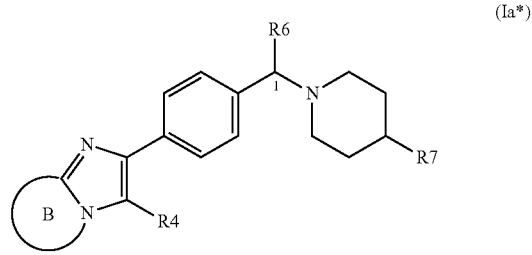

(Ia*)

and the salts thereof are part of the invention.

The invention further includes all mixtures of the stereoisomers mentioned above independent of the ratio, including the racemates.

Some of the compounds and salts according to the invention may exist in different crystalline forms (polymorphs) which are within the scope of the invention.

Furthermore, derivatives of the compounds of formula (I) and the salts thereof which are converted into a compound of formula (I) or a salt thereof in a biological system (bioprecursors or pro-drugs) are covered by the invention. Said biological system is e.g. a mammalian organism, particularly a human subject. The bioprecursor is, for example, converted into the compound of formula (I) or a salt thereof by metabolic processes.

The intermediates used for the synthesis of the compounds of claims 1-5 as described below as well as their use for the synthesis of the compounds of claims 1-5 are one further aspect of the present invention.

The compounds according to the invention can be prepared as follows:

As shown in reaction scheme 1 the compounds of formula (I), wherein ring B and the imidazole to which it is fused, R4 and R7 have the above mentioned meanings and R6 is hydrogen or 1-4C-alkyl, can be obtained by a reductive amination reaction of a corresponding compound of formula (III), wherein R has the meaning —C(O)R6, with a piperidine derivative of formula (II), wherein R7 has the above-mentioned meanings. The reductive amination can be carried out according to standard procedures, for example by the use of NaBH(OAc)3 or NaBH3CN in a suitable solvent exemplified by dimethylformamide (DMF) or methanol or mixtures of methanol and DMF.

The piperidine derivatives of formula (II), wherein R7 has the above-mentioned meanings are known or can be prepared according to known procedures (they may contain protecting group(s) in certain cases to protect other functionalities such as but not limited to NH functions).

The use of the compounds of formula (II) for the synthesis of the compounds of claims 1-5 is one aspect of the present invention.

Compounds of formula (III), wherein R has the meaning —C(O)H can be obtained from corresponding compounds of formula (III), wherein R has the meaning —C(O)O(1-4C-alkyl), in a one or two step procedure. The ester group is selectively reduced to the aldehyde group by methods known to the skilled person, for example by the use of DIBALH under low temperature for example –80 to –60° C. in the one step procedure. Alternatively, the ester group is reduced to the alcohol group (—CH2OH) according to known procedures, for example by the use of LiAlH4 or NaBH4, and then, the resulting alcohol is selectively oxidized to the —C(O)H group by methods known to the skilled person, for example with SO3-pyridine complex or Dess-Martin Periodinane, in the two step procedure.

Alternatively to the reaction sequence described above, the compounds of formula (I), wherein ring B and the imidazole to which it is fused, R4 and R7 have the above mentioned meanings and R6 is hydrogen or 1-4C-alkyl, can be obtained by reaction of a corresponding compound of formula (IIIa), wherein X is a suitable leaving group, such as for example a halogen atom or a sulfonester, with piperidine derivatives of formula (II), wherein R7 has the above-mentioned meanings. The reaction is preferably carried out in an inert solvent, such as for example DMF, at a temperature of from 60 to 100° C. in presence of a base, such as for example triethylamine.

Compounds of formula (IIIa), wherein X is a suitable leaving group, for example a halogen atom can be obtained from corresponding compounds of formula (III), wherein R is —CH(R6)OH and R6 is hydrogen or 1-4C-alkyl, by a halogenation reaction. Such a halogenation reaction can be accomplished, for example, by the use of PBr3 in dichloromethane.

Alternatively, compounds of formula (IIIa), wherein X is a suitable leaving group, for example a halogen atom can be obtained from corresponding compounds of formula (III), wherein R is —CH2R6 and R6 is hydrogen or 1-4C-alkyl, by means of benzylic halogenation. Benzylic halogenation can, for example, be achieved by the use of N-bromosuccinimide (NBS).

Compounds of formula (III), wherein R is —CH(R6)OH and R6 is hydrogen or 1-4C-alkyl, can, for example, be obtained from corresponding compounds of formula (III), wherein R is —C(O)R6, by methods known to the person skilled in the art, for example by reduction with NaBH4 or LiAlH4.

Alternatively, compounds of formula (III), wherein R is —CH(R6)OH and R6 is hydrogen or 1-4C-alkyl, can be obtained from corresponding compounds of formula (III), wherein R is —CH2R6, by means of benzylic oxidation, which can be achieved, for example, by the use of catalytic or equimolar amounts of SeO2.

In a further alternative, compounds of formula (III), wherein R is —CH(1-4C-alkyl)OH can be obtained from corresponding compounds of formula (III), wherein R is —C(O)H by the addition of a suitable metal organic reagent, such as, but not limited to Gringnard or Lithium reagents.

If necessary for the reactions in reaction scheme 1, for the synthesis of compounds of formula (III), wherein ring B and the imidazole to which it is fused and R4 have the above mentioned meanings and R is —C(O)R6 or —CH(R6)OH, these groups can be protected in some or all of the precursors by suitable protecting groups known to the person skilled in the art. Compounds of formula (III), wherein ring B and the imidazole to which it is fused and R4 have the above mentioned meanings and R is a protected ketone, aldehyde or alcohol group, can be deprotected by art-known removal of the protecting groups to generate the corresponding deprotected compounds.

Compounds of formula (III), wherein R has the meanings —C(O)O(1-4C-alkyl), —C(O)R6, —CH(R6)OH or —CH2R6 and R6 is hydrogen or 1-4C-alkyl, can be obtained as shown in reaction scheme 1 by cyclocondensation of compounds of formula (IV) with compounds of formula (V), wherein R4 has the meanings given above, R has the meanings —C(O)O(1-4C-alkyl), —C(O)R6, —CH(R6)OH or —CH2R6 and R6 is hydrogen or 1-4C-alkyl and X1 is a suitable leaving group, such as for example a halogen or a sulfonate. This reaction can be carried out for example in DMF at a temperature from 80 to 140° C.

Reaction scheme 1:

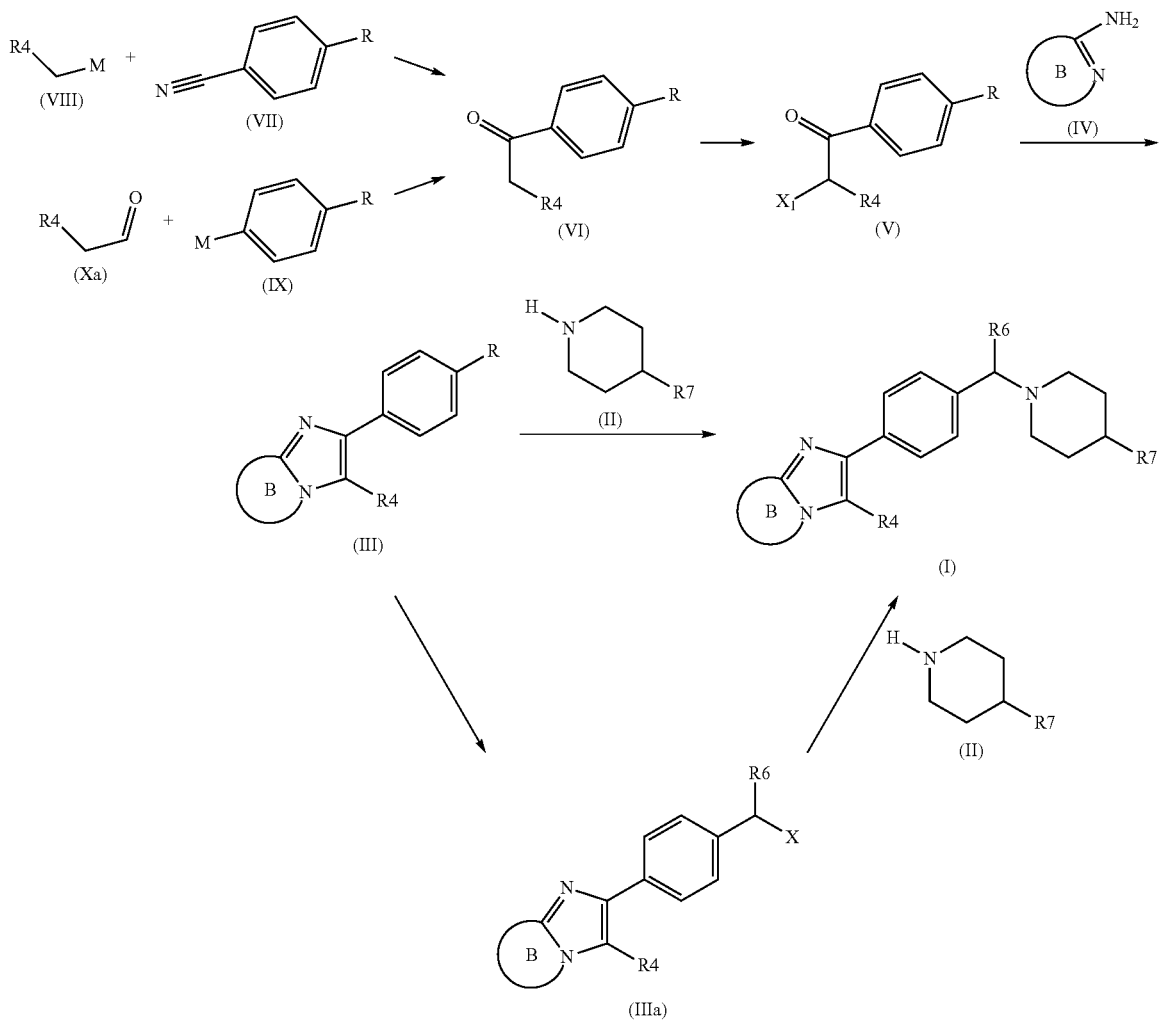

In the case that the substituent of ring B and the imidazole to which it is fused, which is described above as R1 or R3 is a halogen, preferably Cl, Br or I, these halogens can be transformed to other functionalities at this or a later stage of the overall synthesis. This transformation can be achieved for example by the means of catalyzed or uncatalyzed replacement of the halogen by certain reagents exemplified but not limited to boronic acids, tin reagents, Gringnard reagents, cyanide salts, alcohols or amines. Certain Cu or Pd complexes are examples of catalysts, which can be employed for these transformations.

As further shown in reaction scheme 1, compounds of formula (V), wherein R4 has the meanings given above, R has the meanings —C(O)O(1-4C-alkyl), —C(O)R6, —CH(R6)OH or —CH2R6 and R6 is hydrogen or 1-4C-alkyl and X1 is a suitable leaving group, such as for example a halogen or a sulfonate, can be obtained from the corresponding compounds of formula (VI) by procedures known to the skilled person, for example by alpha-halogenation reaction of ketones e.g. using CuBr in suitable solvents such as a mixture of chloroform and ethylacetate. This can also lead to a concomitant cleavage of certain protecting groups, which are part of R, for example acetal protection groups.

Compounds of formula (VI), wherein R4 has the meanings given above and R has the meanings —C(O)O(1-4C-alkyl), —C(O)R6, —CH(R6)OH or —CH2R6 and R6 is hydrogen or 1-4C-alkyl, can for example be synthesized starting from nitriles of formula (VII), wherein R has the meanings —C(O)O(1-4C-alkyl), —C(O)R6, —CH(R6)OH or —CH2R6 and R6 is hydrogen or 1-4C-alkyl, by means of addition of a metal organic reagent of formula (VIII), wherein R4 has the above-mentioned meanings.

Alternatively, compounds of formula (VI), wherein R4 has the meanings given above and R has the meanings —C(O)O (1-4C-alkyl), —C(O)R6, —CH(R6)OH or —CH2R6 and R6 is hydrogen or 1-4C-alkyl, can be synthesized starting from compounds of formula (Xa), wherein R4 has the above-mentioned meanings, by means of addition of a metal organic reagent of formula (IX), wherein R has the meanings —C(O) O(1-4C-alkyl), —C(O)R6, —CH(R6)OH or —CH2R6 and R6 is hydrogen or 1-4C-alkyl. The metal organic reagent of formula (IX) can be a Grignard or a lithium reagent; if necessary the addition of the metal organic reagent is followed by an oxidation reaction.

The oxidation reaction can be carried out by using reagents known to those skilled in the art, for example the pyridine-SO3 complex or Dess-Martin Periodinane.

Compounds of formulae (VII), (VIII), (IX) and (Xa) are either commercially available or can be prepared from commercially available compounds by methods known to the person skilled in the art.

An alternative synthesis route to compounds of formula (III) is described in the reaction scheme 2.

Compounds of formula (III), wherein ring B and the imidazole to which it is fused and R4 have the meanings mentioned above and R is —C(O)O(1-4C-alkyl), —C(O)R6, —CH(R6)OH or —CH2R6 and R6 is hydrogen or 1-4C-alkyl, can be obtained by reaction of a corresponding compound of formula (XI) with compounds of formula (XIII), wherein X3 has the meaning of Cl, Br, I or —OS(O2)CF3. This reaction can, for example, be conducted with palladium acetate, triphenyl phosphine and triethylamine in dioxan.

Compounds of formula (XIII), are either commercially available or can be prepared from commercially available compounds by methods known to the person skilled in the art.

Alternatively, compounds of formula (III), wherein ring B and the imidazole to which it is fused and R4 have the meanings mentioned above and R is —C(O)O(1-4C-alkyl), —C(O)R6, —CH(R6)OH or —CH2R6 and R6 is hydrogen or 1-4C-alkyl, can be obtained by a transition metal catalysed C—C bond formation of a corresponding compound of formula (XII), wherein X2 is Cl, Br or I, with a corresponding compound of formula (XIV), wherein R4-A is R4-B(OH)2, R4-B(O-1-4C-alkly)2,
R4-BOCH(CH3) CH(CH3)O, R4ZnCl, R4ZnBr, R4ZnI or (1-4C-alkyl)3SnR4
and R4 has the meaning mentioned above. This reaction can be carried out for example by the use of tetrakis triphenylphosphine palladium in suitable solvent exemplified by dioxan or mixtures of ethanol in water at a temperature of from 60 to 100° C.

Compounds of formula (XIV) are either commercially available or can be prepared from commercially available compounds by methods known to the person skilled in the art. Compounds of the formula (XII), wherein ring B and the imidazole to which it is fused have the meaning mentioned above and R is —C(O)O(1-4C-alkyl), —C(O)R6, —CH(R6)OH or —CH2R6 and R6 is hydrogen or 1-4C-alkyl and X2 is Cl, Br or I, can be obtained by a halogenation reaction of a corresponding compound of formula (XI) with, for example, N-bromosuccinimide (NBS) or N-iodosuccinimide (NIS).

Compounds of formula (XI), wherein ring B and the imidazole to which it is fused and R is
—C(O)O(1-4C-alkyl), —C(O)R6, —CH(R6)OH or —CH2R6 and R6 is hydrogen or 1-4C-alkyl, can be obtained by cyclocondensation of corresponding compounds of formula (IV) with a corresponding compound of formula (XV), wherein X4 has the meaning of a halogene or tosylate. This reaction can be carried out, for example, in DMF at temperature from 80-140° C.

Compounds of formula (XV), wherein R is —C(O)O(1-4C-alkyl), —C(O)R6, —CH(R6)OH or
—CH2R6 and R6 is hydrogen or 1-4C-alkyl and X4 is mesylate or toyslate, can be prepared with a corresponding compound of formula (XVII) by treatment with suitable reagents such as, but not limited, to sulfonylchlorides.

Compounds of the formula (XV), wherein R is —C(O)O (1-4C-alkyl), —C(O)R6, —CH(R6)OH or
—CH2R6 and R6 is hydrogen or 1-4C-alkyl and X4 is halogen, can be prepared by a halogenation reaction of a corresponding compound of formula (XVI) with, for example, Br2 or NBS in the case that the halogen is Br.

Compounds of formulae (XVI) or (XVII) are either commercially available or can be prepared from commercially available compounds by methods known to the person skilled in the art.

Compounds of the formula (III) in reaction scheme 2, wherein ring B and the imidazole to which it is fused and R4 have the meaning mentioned above and R is —C(O)O(1-4C-alkyl), —C(O)R6, —CH(R6)OH or —CH2R6 and R6 is hydrogen or 1-4C-alkyl, can be transformed into compounds of formula (I) or into compounds of formula (IIIa) and then to compounds of formula (I), as described above in reaction scheme 1.

If necessary for the reactions in reaction scheme 2, for the synthesis of compounds of formula (III), wherein ring B and the imidazole to which it is fused have the meaning mentioned above and R is —C(O)R6 or —CH(R6)OH and R6 is hydrogen or 1-4C-alkyl, these groups can be protected in some or all of the precursors by suitable protecting groups known to the person skilled in the art. Compounds of formula (III), in which R is a protected ketone, aldehyde or alcohol group, can be deprotected by art-known removal of the protecting groups to generate the corresponding deprotected compounds.

Reaction scheme 2:

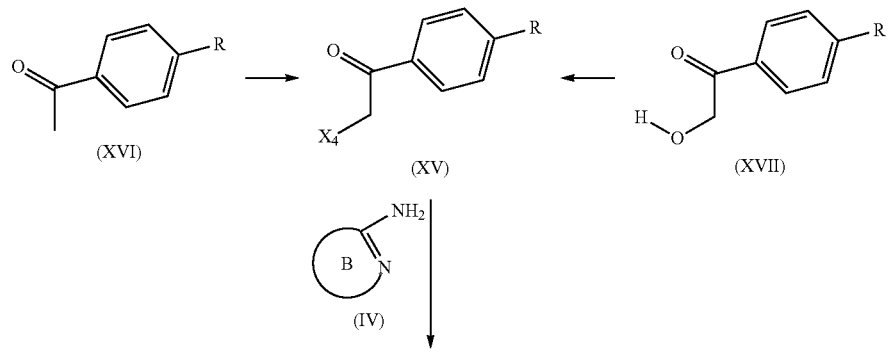

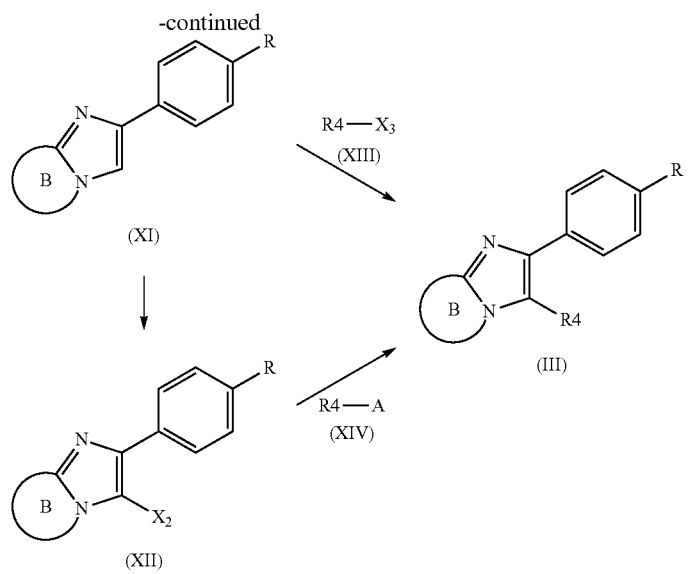

One preferred aspect of the invention is the process for the preparation of the compounds of claims 1-5 according to the examples.

Optionally, compounds of the formula (I) can be converted into their salts, or, optionally, salts of the compounds of the formula (I) can be converted into the free compounds. Corresponding processes are customary for the skilled person.

It is known to the person skilled in the art that, if there are a number of reactive centers on a starting or intermediate compound, it may be necessary to block one or more reactive centers temporarily by protective groups in order to allow a reaction to proceed specifically at the desired reaction center. A detailed description for the use of a large number of proven protective groups is found, for example, in T. W. Greene, Protective Groups in Organic Synthesis, John Wiley & Sons, 1999, 3rd Ed., or in P. Kocienski, Protecting Groups, Thieme Medical Publishers, 2000.

The compounds according to the invention are isolated and purified in a manner known per se, e.g. by distilling off the solvent in vacuo and recrystallizing the residue obtained from a suitable solvent or subjecting it to one of the customary purification methods, such as column chromatography on a suitable support material.

Salts of the compounds of formula (I) according to the invention can be obtained by dissolving the free compound in a suitable solvent (for example a ketone such as acetone, methylethylketone or methylisobutylketone, an ether such as diethyl ether, tetrahydrofuran or dioxane, a chlorinated hydrocarbon such as methylene chloride or chloroform, or a low molecular weight aliphatic alcohol such as methanol, ethanol or isopropanol) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the compounds and salts according to the invention can be obtained e.g. by asymmetric synthesis, by using chiral starting compounds in synthesis and by splitting up enantiomeric and diasteriomeric mixtures obtained in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated e.g. by forming diastereomers with a chiral auxiliary agent, resolving the diastereomers obtained and removing the chiral auxiliary agent. As chiral auxiliary agents, for example, chiral acids can be used to separate enantiomeric bases such as e.g. mandelic acid and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is the enzymatic separation.

As will be appreciated by persons skilled in the art, the invention is not limited to the particular embodiments described herein, but covers all modifications of said embodiments that are within the spirit and scope of the invention as defined by the appended claims. The following examples illustrate the invention in greater detail, without restricting it. Further compounds according to the invention, of which the preparation is not explicitly described, can be prepared in an analogous way.

The compounds, which are mentioned in the examples and the salts thereof represent preferred embodiments of the invention as well as a claim covering all subcombinations of the residues of the compound of formula (I) as disclosed by the specific examples.

The term "according to" within the experimental section is used in the sense that the procedure referred to is to be used "analogously to".

EXAMPLES

The following abbreviations are used: In the examples, m.p. stands for melting point, h or hrs for hour(s), min for minutes, conc. for concentrated, calc. for calculated, fnd. for found, EF for elemental formula, MS for mass spectrometry, M for molecular ion in mass spectrometry, TLC: thin layer chromatography, HPLC for high performance liquid chromatography, $^1$H-NMR for $^1$H nuclear magnetic resonance spectroscopy (chemical shifts are reported as ppm against tetramethylsilane as internal standard, coupling constants J are reported in Hz), w/w for weight by weight, RT for room temperature (20-25° C.), DCM for dichloromethane, THF for tetrahydrofurane, DMSO for dimethylsulfoxide, DBU for 1,8-diazabicyclo[5.4.0]undec-7-ene, EtOAc for ethyl acetate, DIBAL for diisobutylaluminiumhydrid, DCM for dichloromethane, ACN for acetonitril and other abbreviations have their meanings customary per se to the skilled person.

Intermediate A

2-[3-(piperidin-4-yl)-1H-1,2,4-triazol-5-yl]pyridine dihydrochloride (procedure described in US4011218 or WO2005100344)

Step-I: pyridine-2-carbohydrazonamide

A solution of pyridine-2-carbonitrile 20 g (192 mM), hydrazine hydrate (3 eq.) in ethanol (50 ml) is stirred at room temperature for 18 hrs. Reaction mass is then diluted with water, extracted with ethyl acetate, dried over anhydrous sodium sulphate and concentrated under vacuum to yield desired compound.

MS (M+1): 137.28
$^1$H NMR (300 MHZ, CDCl$_3$): δ8.53 (d, 1H, J=8 & 2.3 Hz), 8.02 (d, 1H, J=7.8 & 2.1 Hz), 7.72 (t, 1H, J=8.2 & 2 Hz), 7.29 (t, 1H, J=8.4 & 2.1 Hz), 5.42 (bs, 2H), 4.60 (bs, 2H).

Step-II: tert-butyl 4-({(2Z)-2-[amino(pyridin-2-yl)methylidene]hydrazinyl}carbonyl)piperidine-1-carboxylate To as solution of 1-(tert-butoxycarbonyl) piperidine-4-carboxylic acid 37 g (167 mM) in dichloromethane (300 ml) is added carbonyl diimidazole (1 eq.) in small portion over a period of 30 min. pyridine-2-carbohydrazonamide is then added to reaction mixture and stirred at room temperature for 3 hrs. Dichloromethane is evaporated and reaction mass is then stirred in water for 30 min. solid precipitated is filtered and dried to afford the desired compound.

MS (M+1): 348.07
$^1$H NMR (300 MHZ, CDCl3): δ10.75 (s, 1H), 8.56 (d, 1H, J=4.5 Hz), 8.10 (d, 1H, J=8.3 Hz), 7.75 (dt, 1H, J=8.2 & 1.3 Hz), 7.34 (dt, 1H, J=7.9 & 1.5 Hz), 4.18 (bs, 2H), 3.46 (s, 1H), 2.88 (t, 2H), 1.91 (m, 2H), 1.72 (m, 4H), 1.47 (s, 9H).

Step-III: tert-butyl 4-[5-(pyridin-2-yl)-1H-1,2,4-triazol-3-yl]piperidine-1-carboxylate Tert-butyl 4-({(2Z)-2-[amino(pyridin-2-yl) methylidene]hydrazinyl}carbonyl) piperidine-1-carboxylate 45 g (129 mM) obtained in step II is melted at 220° C. under nitrogen atmosphere for 1 hr. Reaction is then cooled to 150° C. and added ethanol till solid get dissolved. Ethanol is then evapourated to get desired compound.

MS (M+1): 330.5
$^1$H NMR (300 MHZ, DMSO): δ 9.11 (s, 1H), 8.74 (dd, 1H, J=4.8 & 1.3 Hz), 8.17 (dt, 2H, J=8.2 & 2.1 Hz), 7.66 (dt, 1H, J=8.0 & 1.3 Hz), 3.34 (m, 2H), 3.18 (m, 1H), 3.06 (m, 2H), 2.20 (m, 2H), 1.99 (m, 2H), 1.28 (s, 9H).

Step-IV: 2-[3-(piperidin-4-yl)-1H-1,2,4-triazol-5-yl]pyridine dihydrochloride

To a solution of tert-butyl 4-[5-(pyridin-2-yl)-1H-1,2,4-triazol-3-yl]piperidine-1-carboxylate 39 g (111 mM) in methanol 50 is added 100 ml solution of HCl in dioxane and stirred at room temperature for 3 hrs. Solid precipitated is then filtered and washed with cold acetonitrile to obtained 2-[3-(piperidin-4-yl)-1H-1,2,4-triazol-5-yl]pyridine dihydrochloride as white solid.

$^1$H NMR (300 MHZ, DMSO): δ 9.11 (s, 1H), 8.97 (s, 1H), 8.74 (dd, 1H, J=4.8 & 1.3 Hz), 8.17 (dt, 2H, J=8.2 & 2.1 Hz), 7.66 (dt, 1H, J=8.0 & 1.3 Hz), 3.34 (m, 2H), 3.18 (m, 1H), 3.06 (m, 2H), 2.20 (m, 2H), 1.99 (m, 2H)

Intermediate B

4-[3-(piperidin-4-yl)-1H-1,2,4-triazol-5-yl]pyridine

Prepared according to intermediate A.

Intermediate C 2-methyl-6-[3-(piperidin-4-yl)-1H-1,2,4-triazol-5-yl]pyridine

Prepared according to intermediate A.

Intermediate D 5-methyl-2-[3-(piperidin-4-yl)-1H-1,2,4-triazol-5-yl]pyridine

Prepared according to intermediate A.

Intermediate E 5-chloro-2-[3-(piperidin-4-yl)-1H-1,2,4-triazol-5-yl]pyridine

Prepared according to intermediate A.

Intermediate F

2-[3-(piperidin-4-yl)-1H-1,2,4-triazol-5-yl]pyrimidine

Prepared according to intermediate A.

Intermediate G

4-[5-(1,3-thiazol-2-yl)-1H-1,2,4-triazol-3-yl]piperidine

Prepared according to intermediate A.

Intermediate H

4-[5-(furan-2-yl)-1H-1,2,4-triazol-3-yl]piperidine

Prepared according to intermediate A.

Intermediate I

4-[5-(thiophen-2-yl)-1H-1,2,4-triazol-3-yl]piperidine

Prepared according to intermediate A.

Intermediate J

4-[5-(1H-pyrrol-2-yl)-1H-1,2,4-triazol-3-yl]piperidine

Step-I: 1H-pyrrole-2-carbohydrazonamide

A solution of 1H-pyrrole-2-carbonitrile 10 g (108 mM) and sodium methoxide (1 eq) in ethanol (20 ml) and stirred for 10 min. Hydrazine hydrate (3 eq.) is then added and resulting reaction mixture is stirred at room temperature for 18 hrs. Reaction mass is then diluted with water, extracted with ethyl acetate, dried over anhydrous sodium sulphate and concentrated under vacuum to yield desired compound.

Step II, III, IV are similar to intermediate A.

Intermediate K

2-[3-(piperidin-4-yl)-1H-pyrazol-5-yl]pyridine

Prepared according to intermediate A.

Intermediate L

2-[3-(piperidin-4-yl)-1,2,4-oxadiazol-5-yl]pyridine

Intermediate L is prepared according to intermediate A.

Intermediate M 4-(5-phenyl-1H-1,2,4-triazol-3-yl)piperidine

Intermediate M is prepared according to intermediate J.

Example 1

3-phenyl-2-(4-{[4-(5-pyridin-2-yl-1,2,4-triazol-3-yl)piperidin-1-yl]methyl}phenyl)imidazo[1,2-a]pyrimidine Step 1: 1-[4-(dimethoxymethyl)phenyl]-2-phenylethanol A mixture of Mg turnings 2.4 g (0.1 mol) and 2 ml 1-bromo-4-(dimethoxymethyl)benze (0.012 mol) in THF (10 ml) is heated under nitrogen atmosphere until the reaction starts. Subsequently additional 1-bromo-4-(dimethoxymethyl)benze 14.71 ml (0.088 mol) dissolved in 30 ml THF is added slowly and the reaction refluxed for 1 h mixture to complete formation of the Gringnard reagent. A solution of 11.70 ml phenylacetaldehyde (0.1 mol) in 100 ml THF is added at to 0° C. and the reaction refluxed for 2 h upon completion of the addition. The mixture is worked up by pouring into saturated aqueous $NH_4Cl$ and extraction with ethyl acetate. The combined organic layers are washed with brine, dried over MgSO4 and the solvent is evaporated under reduced pressure. The brown-black oily product is used for the next step without purification.

Step 2: 1-[4-(dimethoxymethyl)phenyl]-2-phenylethanone 29.16 g (0.183 mol) sulfur trioxide pyridine complex is added in portions to a solution of 33 g 1-[4-(dimethoxymethyl)phenyl]-2-phenylethanol in dichloromethane (540 ml), DMSO (140 ml) and triethylamine (25.5 ml) at 10° C. The mixture is slowly warmed to room temperature and stirred for 2 h. Water is added and the organic phase is separated, washed with 1 mol/l HCl, 3 times with 5% w/w sodium thiosulfate solution and saturated NaCl. The combined organic phases are dried over sodium sulfate and the solvents is evaporated. The residue is purified on a silica gel column chromatography (n-Hexan/EtOAc).

MS (M+1): 271

Characteristic 1H NMR (300 MHz, dDMSO) signals: 8.1 ppm (d, 2H); 7.6 ppm (d, 2H); 5.4 ppm (s, 1H), 4.3 (s, 2H)

Step 3: 4-[bromo(phenyl)acetyl]benzaldehyde

A solution of 3.0 g 1-[4-(dimethoxymethyl)phenyl]-2-phenylethanone (0.011 mol) in 60 ml ethyl acetate and 60 ml chloroform is heated to reflux. Powdered cupric bromide 4.96 g (0.022 mol) is added over 2 h period in small portions under nitrogen atmosphere. Refluxing is continued for 1 h until the green color and dark cupric bromide disappears, the reaction is then mixture cooled to room temperature and filtered though celite. The solvents is evaporated and the residue purified on silica gel. (n-Hexan/EtOAc).

MS (M+-Br): 223

Characteristic 1H NMR (300 MHz, dDMSO) signals: 10.0 ppm (s, 1H); 8.3 ppm (d, 2H); 8.0 ppm (d, 2H); 7.2 ppm (s, 1H)

Step 4: 4-(3-phenylimidazo[1,2-a]pyrimidin-2-yl)benzaldehyde 4.6 g 4-[bromo(phenyl)acetyl]benzaldehyde and 1.64 g pyrimidin-2-amine are stirred in 140 ml DMF at 90° C. for 4 h. The DMF is evaporated and the residue suspended in ethylacetate over night, collected by filtration.

MS (M+1): 300

Characteristic 1H NMR (400 MHz, dDMSO) signals: 10 ppm (s, 1H), 7.0 ppm (1H)

Step 5: 3-phenyl-2-(4-{[4-(5-pyridin-2-yl-1H-1,2,4-triazol-3-yl)piperidin-1-yl]methyl}phenyl)imidazo[1,2-a]pyrimidine 0.14 ml triethylamine is added to a solution of 156 mg 4-(3-phenylimidazo[1,2-a]pyrimidin-2-yl)benzaldehyde in 10 ml methanol. To this solution a solution of 140 mg 2-(5-Piperidin-1,2,4]triazol-3-yl)-pyridine*2HCl (Intermediate A prepared from tert-butyl 4-(hydrazinocarbonyl)piperidine-1-carboxylate and pyridine-2-carbonitrile according to a procedure described in U.S. Pat. No. 4,011,218 or WO2005100344) is added, followed by 0.07 ml glacial acetic acid and 198 mg $NaBH(OAc)_3$. The resulting mixture is stirred at room temperature. Three additional portions of 198 mg $NaBH(OAc)_3$ are added after 2, 4 and 20 hours. The solvents is removed by evaporation after 24 h and the residue purified by chromatography on silica gel (dichlormethan/methanol).

MS (M+1): 513
Characteristic 1H NMR (400 MHz, dDMSO) signals: 8.6 ppm (1H); 7 ppm (1H); 3.5 ppm (s, 2H)

Example 2

3-phenyl-2-(4-{[4-(5-pyridin-2-yl-1H-1,2,4-triazol-3-yl)piperidin-1-yl]methyl}phenyl)imidazo[1,2-a]pyridine Example 2 is prepared in a manner according to example 1 by using pyridin-2-amine in step 4.
MS (M+1): 512
Characteristic 1H NMR (400 MHz, dDMSO) signals: 8.7 ppm (1H); 6.9 ppm (1H); 3.5 ppm (s, 2H)

Example 3

7-phenyl-6-(4-{[4-(5-pyridin-2-yl-1H-1,2,4-triazol-3-yl)piperidin-1-yl]methyl}phenyl)imidazo[1,2-b][1,2,4]triazine Example 3 is prepared in a manner according to example 1 by using 1,2,4-triazin-3-amine in step 4.
MS (M+1): 514
Characteristic 1H NMR (400 MHz, dDMSO) signals: 8.0 ppm (1H); 7.9 ppm (1H); 3.5 ppm (s, 2H)

Example 4

3-phenyl-2-(4-{[4-(3-pyrazin-2-yl-1,2,4-oxadiazol-5-yl)piperidin-1-yl]methyl}phenyl)imidazo[1,2-a]pyrimidine This example is prepared in a manner similar to 1 by using commercially available 2-(5-piperidin-4-yl-1,2,4-oxadiazol-3-yl)pyrazine in the last step.
Analytical Data
MS (M+1): 515
Characteristic 1H NMR (400 Hz, dDMSO) signals: 9.2 ppm (s, 1H); 7.1 ppm (dd, 1H); 3.5 ppm (s, 2H).

Example 5

3-phenyl-2-(4-{[4-(5-pyridin-2-yl-1,2,4-triazol-3-yl)piperidin-1-yl]methyl}phenyl)imidazo[1,2-a]pyridine-8-carbonitrile This example is prepared in a manner according to example 12 by using 2-aminonicotinonitrile in the first step.
MS (M+1): 537.23
$^1$H NMR (CD$_3$OD): δ 8.675 (dd, J=7.2 Hz, 1.2 Hz, 1H), 8.073 (d, J=7.8 Hz, 1H), 7.945-7.87 (m, 2H), 7.65 (d, J=8.1 Hz, 2H), 7.60-7.56 (m, 2H), 7.49-7.46 (m, 3H), 7.444-7.419 (m, 3H), 7.345 (d, J=8.4 Hz, 2H), 7.010 (t, 1H), 3.75 (s, 2H), 3.16-3.12 (m, 2H), 3.01-2.91 (m, 1H), 2.48-2.41 (m, 2H), 2.15-1.96 (m, 3H).

Example 6

6-bromo-3-phenyl-2-(4-{[4-(5-pyridin-2-yl-1,2,4-triazol-3-yl)piperidin-1-yl]methyl}phenyl)imidazo[1,2-a]pyridine Step 1: 4-(6-bromo-3-phenylimidazo[1,2-a]pyridin-2-yl)benzaldehyde 3.3 mMol (2-Bromo-2-phenyl-ethanoyl)-benzaldehyde and 1.2 equivalents of 5-Bromo-pyridin-2-ylamine are dissolved in 10 ml DMF. The reaction mixture is heated at 100° C. for 18 hours. The reaction mixture is cooled and water is added. It is then extracted with ethyl acetate. The organic layer is dried and concentrated. The crude is purified by column chromatography to yield the desired compound.
MS (M+1): 377.27, 379.27.
1H NMR (CDCl3): δ 9.950 (s, 1H), 8.1 (dd, J=1.8 Hz, 0.9 Hz, 1H), 7.86-7.76 (m, 4H), 7.72 (dd, J=9.3 Hz, 0.6 Hz, 1H), 7.6-7.54 (m, 5H), 7.5 (dd, J=9.3 Hz, 1.8 Hz, 1H).

Step 2: [4-(6-bromo-3-phenylimidazo[1,2-a]pyridin-2-yl)phenyl]methanol

To the stirred solution 4-(6-bromo-3-phenylimidazo[1,2-a]pyridin-2-yl)benzaldehyde (0.795 mM) in 15 mL of methanol is added NaBH$_4$ (1.5 eq) at 0° C. and the reaction is allowed to stir at room temperature for 1 hr. The reaction is concentrated and quenched with water. The precipitated solid is filtered and dried to yield the desired product.
MS (M+1): 379.27, 381.27.
$^1$H NMR (DMSO-d$_6$): δ 8.1 (dd, J=1.8 Hz, 0.6 Hz, 1H). 7.7-7.525 (m, 8H), 7.5 (dd, J=8.4 Hz, 1.8 Hz, 1H), 7.2 (d, J=8.4 Hz, 2H), 5.4 (bs, 1H), 4.5 (s, 2H).

Step 3: 6-bromo-3-phenyl-2-(4-{[4-(5-pyridin-2-yl-1,2,4-triazol-3-yl)piperidin-1-yl]methyl}phenyl)imidazo[1,2-a]pyridine To the stirred solution of 0.52 mM of [4-(6-bromo-3-phenylimidazo[1,2-a]pyridin-2-yl)phenyl]methanol in 15 mL of dichlormethane is added methanesulfonyl chloride (1.1 eq) at 0° C. followed by triethylamine (1.5 eq). The reaction mixture is allowed to stir at room temperature for 3 h. The reaction is quenched with water and extracted with DCM. The organic layer is dried and concentrated. It is then taken up in the next reaction without further purification. The crude is dissolved in 5 mL of DMF. To this solution 2-(5-Piperidin-[1,2,4]triazol-3-yl)-pyridine*2HCl (1 eq), triethylamine (4 eq) are added. The reaction mixture is heated at 80° C. for 3 h. The reaction mixture is quenched with water and extracted with ethyl acetate. The organic layer is dried and concentrated. The crude obtained is triturated with pentane to obtain the desired compound.
MS (M+1): 590.13, 592.07.
$^1$H NMR (DMSO-d6): δ 14.2-14.0 (bs, 1H), 8.7 (d, J=4.2 Hz 1H), 8.1-7.9 (m, 3H), 7.7-7.5 (m, 8H), 7.4 (dd, J=9.3 Hz, 1.8 Hz, 2H), 7.2 (d, J=8.4 Hz, 2H), 3.5 (s, 2H), 2.8 (d, 2H) 2.8-2.7 (m, 1H), 2.1 (t, 2H), 2.0 (t, 2H), 1.8 (t, 2H).

Example 7

6-chloro-3-phenyl-2-(4-{[4-(5-pyridin-2-yl-4H-1,2,4-triazol-3-yl)piperidin-1-yl]methyl}phenyl)imidazo[1,2-a]pyridine This compound is prepared according to example 6 by using 5-chloropyridin-2-amine in step1.
MS (M+1): 546.20, 548.20.
$^1$H NMR (CDCl$_3$): δ 8.7 (s, 1H). 8.2 (d, J=7.5 Hz, 1H), 8.0 (d, J=1.2 Hz, 1H), 7.8 (t, J=7.5 Hz, 1H), 7.6-7.5 (m, 6H), 7.5 (dd, J=7.8 Hz, 2.1 Hz, 2H), 7.2 (d, J=8.1 Hz, 2H), 7.3 (s, 1H), 7.2 (dd, J=9.3 Hz, 1.8 Hz, 1H), 3.5 (s, 2H), 3.0-2.8 (m, 3H), 2.1-1.9 (m, 6H)

Example 8

8-methyl-3-phenyl-2-(4-{[4-(5-pyridin-2-yl-1,2,4-triazol-3-yl)piperidin-1-yl]methyl}phenyl)imidazo[1,2-a]pyridine This compound is prepared according to example 6 by using 3-methylpyridin-2-amine in step1.

MS (M+1): 526.27.

$^1$H NMR (CDCl$_3$): δ 8.7 (d, J=3.3 Hz, 1H), 8.2 (d, J=7.8 Hz, 1H), 7.9-7.7 (m, 2H), 2.2-1.9 (m, 7H), 7.6 (d, J=8.1 Hz, 1H), 7.5-7.5 (m, 5H), 7.3 (t, J=5.7 Hz, 1H), 7.2 (d, J=8.1 Hz, 3H), 7.0 (d, J=6.9 Hz, 1H), 6.7 (t, J=6.9 Hz, 1H), 3.5 (s, 2H), 3.0-2.8 (m, 2H), 2.7 (s, 3H)

Example 9

3-(4-fluorophenyl)-2-(4-{[4-(5-pyridin-2-yl-1,2,4-triazol-3-yl)piperidin-1-yl]methyl}phenyl)imidazo[1,2-a]pyridine Step1: 4-[3-(4-fluorophenyl)imidazo[1,2-a]pyridin-2-yl]benzaldehyde 0.46 g (1.5 mM) 4-(3-bromoimidazo[1,2-a]pyridin-2-yl)benzaldehyde (prepared as described by Sundberg et al.; J. Heterocyclic Chem., 25, 129, 1988) is dissolved in 5 mL of toluene. To this mixture is added 4-fluorphenyl boronic acid (1.5 eq) followed by tetrakis triphenylphosphine palladium (0) 10% by wt, K$_2$CO$_3$ (3 eq) and ethanol water mixture (4 mL). The reaction mixture is heated at 90° C. for 4-6 h. The reaction is cooled to room temperature and 20 mL of water is added and the reaction mixture is extracted with ethyl acetate. The organic layer is dried and concentrated. The crude is purified by flash column chromatography to obtain the desired compound.

MS (M+1): 317.33.

$^1$H NMR (DMSO-d$_6$): δ 9.9 (s, 1H), 8.0 (d, J=6.9 Hz, 1H), 7.85 (d, J=6.6 Hz, 2H), 7.8 (d, J=8.4 Hz, 2H), 7.45 (d, J=9.3 Hz, 1H), 7.6 (m, 2H), 7.45 (m, 2H), 7.35 (m, 1H), 6.9 (dt, J=6.9 Hz, 1.2 Hz, 1H).

Step 2: 3-(4-fluorophenyl)-2-(4-{[4-(5-pyridin-2-yl-1,2,4-triazol-3-yl)piperidin-1-yl]methyl}phenyl)imidazo[1,2-a]pyridine To a solution of 0.1 g (0.31 mM) 4-[3-(4-fluorophenyl)imidazo[1,2-a]pyridin-2-yl]benzaldehyde in 5 mL of THF is added triethylamine (2 eq). The reaction mixture is stirred for 5 minutes. To this solution is added 2-(5-Piperidin-[1,2,4]triazol-3-yl)pyridine*2HCl (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 530.27.

$^1$H NMR(CD$_3$OD): δ 8.7 (d, 1H), 8.1 (m, 2H), 7.9 (dt, J=1.8 Hz, 7.8 Hz, 1H), 7.6-7.7 (m, 3H), 7.2-7.5 (m, 8H), 6.9 (dt, J=6.9 Hz, 1.2 Hz, 1H), 3.9 (s, 2H), 3.0 (m, 1H), 2.7 (t, 2H), 2.1 (m, 4H), 2.0 (m, 2H).

Example 10

5-phenyl-6-(4-{[4-(5-pyridin-2-yl-1,2,4-triazol-3-yl)piperidin-1-yl]methyl}phenyl)imidazo[2,1-b][1,3]thiazole Step1: methyl 4-(phenylacetyl)benzoate 33 g methyl-4-(1-hydroxy-2-phenylethyl)benzoate (prepared as described by Berk et al.; J. Org. Chem. 1988, 53, 5791) is dissolved in 200 mL of dichloromethane. The solution is cooled to 0-10° C. To this is added DMSO (10 eq) and triethylamine (1.5 eq) followed by addition of 1.5 eq of pyridine-sulphur trioxide-complex. The reaction is stirred overnight at RT 200 ml of water is added. Then ethyl acetate is added and the organic layer is separated, dried, and concentrated to obtain the crude compound. It is purified by column chromatography to obtain the desired compound.

$^1$H NMR (DMSO-d$_6$) δ 8.15 (d, J=8.4 Hz, 2H), 8.06 (d, J=8.4 Hz, 2H), 7.40-7.19 (m, 5H), 4.44 (s, 2H), 3.87 (s, 3H).

Step 2: methyl 4-[bromo(phenyl)acetyl]benzoate methyl 4-(phenylacetyl)benzoate (3.8 g, 14.9 mM) is dissolved in 300 mL of ethyl acetate/chloroform mixture. The reaction mixture is refluxed and cupric bromide (2 eq) is added in portions over a period of 2 h while constantly purging with nitrogen. The reaction mixture is further refluxed for 4 h. The reaction mixture is cooled, filtered and evaporated. The crude product is purified by column chromatography.

$^1$H NMR (DMSO-d$_6$) δ 8.18 (d, J=8.1 Hz, 2H), 8.05 (d, J=7.5 Hz, 2H), 7.6-7.3 (m, 5H), 7.21 (s, 1H), 3.87 (s, 3H).

Step 3: methyl 4-(5-phenylimidazo[2,1-b][1,3]thiazol-6-yl)benzoate 0.7 g (2.1 mM) of methyl 4-[bromo(phenyl)acetyl]benzoate and 2-aminothiazole (2.5 eq) are stirred in 20 ml DMF at 90° C. for 6 h. The DMF is evaporated and the crude product is purified by column chromatography.

MS (M+1): 335.27.

$^1$H NMR (DMSO-d$_6$): δ 7.9 (d, J=8.4 Hz, 2H), 7.7 (d, J=4.5 Hz, 1H), 7.6 (d, J=8.7 Hz, 2H), 7.4-7.6 (m, 5H), 7.3 (d, J=4.5 Hz, 1H), 3.8 (s, 3H).

Step 4: [4-(5-phenylimidazo[2,1-b][1,3]thiazol-6-yl)phenyl]methanol 0.12 g (0.36 mM) of methyl 4-(5-phenylimidazo[2,1-b][1,3]thiazol-6-yl)benzoate is dissolved in 8 mL of dry THF. To this is added lithium aluminum hydride (5 eq) at 0° C. The reaction mixture is brought to RT and stirred for 2 h. It is then quenched with sat. solution of sodium sulphate and filtered. The filtrate is evaporated and extracted in ethyl acetate. The organic layer is dried and concentrated to obtain the desired compound.

MS (M+1): 307.27.

$^1$H NMR (DMSO-d$_6$) δ 7.7 (d, J=4.5 Hz, 1H), 7.5-7.4 (m, 7H), 7.3 (d, J=4.5 Hz, 1H), 7.2 (d, J=8.1 Hz, 2H), 5.2 (t, J=5.7 Hz, 1H), 4.5 (d, J=5.7 Hz, 2H).

Step 5: 5-phenyl-6-(4-{[4-(5-pyridin-2-yl-1,2,4-triazol-3-yl)piperidin-1-yl]methyl}phenyl)imidazo[2,1-b][1,3]thiazole To the stirred solution of 0.12 g (0.39 mM) of [4-(5-phenylimidazo[2,1-b][1,3]thiazol-6-yl)phenyl]methanol in 5 mL of dichlormethane is added methansulfonyl chloride (1.5 eq) at 0° C. followed by triethylamine (2.5 eq). The reaction mixture is allowed to stir at room temperature for 3 h. The reaction is quenched with water and extracted with DCM. The organic layer is dried and concentrated. It is then taken up in the next reaction without further purification. The crude product is dissolved in 4 mL of DMF. To this is added 2-(5-Piperidin-[1,2,4]triazol-3-yl)pyridine*2HCl (1.2 eq), NaHCO$_3$ (4 eq). The reaction mixture is stirred at RT for 12 h and then heated at 80° C. for 3 h. The reaction mixture is quenched with water and extracted with ethyl acetate. The organic layer is dried and concentrated. The crude obtained is converted to its HCl salt by addition of ethereal HCl. The solid obtained is washed with acetone/methanol to obtain the desired compound.

MS (M+1): 518.2.

$^1$H NMR (D$_2$O): δ 8.7 (d, J=5.7 Hz, 1H), 8.5 (t, J=8.1 Hz, 1H), 8.4 (d, J=7.8 Hz, 1H), 8.0-7.9 (m, 1H), 7.8 (d, J=4.5 Hz, 1H), 4.3 (s, 2H), 3.6 (br d, J=12 Hz, 2H), 7.6-7.40 (m, 10H), 3.4-3.2 (m, 1H), 3.2-3.1 (m, 2H), 2.1-1.9 (m, 2H), 2.3 (br d, J=12.6, 2H).

Example 11

5-phenyl-6-(4-{[4-(5-pyridin-2-yl-1,2,4-triazol-3-yl)piperidin-1-yl]methyl}phenyl)imidazo[2,1-b][1,3,4]thiadiazole Step 1: methyl 4-(5-phenylimidazo[2,1-b][1,3,4]thiadiazol-6-yl)benzoate 0.7 g (2.1 mM) methyl 4-[bromo(phenyl)acetyl]benzoate (prepared as described under example 10) and 2-aminothiadiazole (2 eq) are stirred in 15 ml DMF at 90° C. for 6 h. The DMF is evaporated and the residue suspended in ethylacetate over night. The desired product is collected by filtration.

MS (M+1): 336.20.

$^1$H NMR (DMSO-d$_6$): δ 9.2 (s, 1H), 7.91 (d, 2H, J=7.2 Hz), 7.7 (d, 2H, J=6.9 Hz), 7.5-7.4 (m, 5H), 3.8 (s, 3H).

Step 2: [4-(5-phenylimidazo[2,1-b][1,3,4]thiadiazol-6-yl)phenyl]methanol methyl 4-(5-phenylimidazo[2,1-b][1,3,4]thiadiazol-6-yl)benzoate (0.25 g, 0.77 mM) is dissolved in 25 mL DCM. To this is added DIBAL (5 eq) at RT. The reaction mixture is stirred for 20 min. The reaction mixture is diluted with DCM and the organic layer is washed with water. The organic layer is dried and concentrated to obtain the desired compound as a white solid.

MS (M+1): 308.20.

$^1$HNMR(CD$_3$OD): δ 9.02 (s, 1H), 7.58-7.50 (m, 4H), 7.43-7.38 (m, 3H), 7.32 (d, 2H, J=9 Hz), 4.6 (s, 2H).

Step 3: 5-phenyl-6-(4-{[4-(5-pyridin-2-yl-1,2,4-triazol-3-yl)piperidin-1-yl]methyl}phenyl)imidazo[2,1-b][1,3,4]thiadiazole To the stirred solution of 0.21 g (0.684 mM) of [4-(5-phenylimidazo[2,1-b][1,3,4]thiadiazol-6-yl)phenyl]methanol in 15 mL of dichlormethane is added methansulfonyl chloride (1.5 eq) at 0° C. followed by triethylamine (2.0 eq). The reaction mixture is allowed to stir at room temperature for 3 h. The reaction is concentrated. It is then taken up in the next reaction without further purification. The crude product is dissolved in 10 mL of DMF. To this is added 2-(5-Piperidin-[1,2,4]triazol-3-yl)-pyridine*2HCl (2.5 eq), triethylamine (3 eq). The reaction mixture is heated at 80° C. for 8 h. The reaction mixture is quenched with water and extracted with ethyl acetate. The organic layer is dried and concentrated. The crude product is purified by cc to obtain the desired compound.

MS (M+1): 519.27.

$^1$HNMR(CDCl$_3$): δ 8.67 (d, 1H, J=4.2 Hz), 8.5 (s, 1H), 8.1 (d, 1H, J=7.8 Hz), 7.8 (dt, 1H, J=7.8, 8.1 Hz), 7.66-7.62 (m, 4H), 7.4-7.2 (m, 6H), 3.59 (s, 2H), 3.0 (d, 2H), 2.9 (t, 1H), 2.1-1.9 (m, 6H).

Example 12

6-bromo-3-phenyl-2-(4-{[4-(5-pyridin-2-yl-1,2,4-triazol-3-yl)piperidin-1-yl]methyl}phenyl)imidazo[1,2-a]pyrimidine Step 1: 4-(6-bromo-3-phenylimidazo[1,2-a]pyrimidin-2-yl)benzaldehyde 0.15 g (0.5 mM) of 4-[bromo(phenyl)acetyl]benzaldehyde and 2.0 equivalents of 5-bromopyrimidin-2-amine are dissolved in 6 ml DMF. The reaction mixture is heated at 90° C. overnight. The reaction mixture is cooled and water is added. It is then extracted with ethyl acetate. The organic layer is dried and concentrated. The crude product is purified by column chromatography to obtain the desired compound.

MS (M+1): 378.27, 380.27.

$^1$H NMR (DMSO-d$_6$): δ 10.0 (s, 1H), 8.7 (d, 1H, J=2.4 Hz), 8.6 (d, 1H, J=2.4 Hz), 7.9 (d, 2H, J=8.7 Hz), 7.8 (d, 2H, J=8.4 Hz), 7.5-7.6 (m, 5H).

Step 2: 6-bromo-3-phenyl-2-(4-{[4-(5-pyridin-2-yl-1,2,4-triazol-3-yl)piperidin-1-yl]methyl}phenyl)imidazo[1,2-a]pyrimidine To a solution of 0.044 g (0.116 mM) 4-(6-bromo-3-phenylimidazo[1,2-a]pyrimidin-2-yl)benzaldehyde in 3 mL of THF is added triethylamine (2 eq). The reaction mixture is stirred for 5 minutes. To this solution is added 2-(5-Piperidin-[1,2,4]triazol-3-yl)-pyridine*2HCl (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 591.27, 593.13.

$^1$H NMR(CDCl$_3$): δ 8.63 (d, 1H, J=4.8 Hz), 8.61 (d, 1H, J=2.4 Hz), 8.57 (d, 1H, J=2.4 Hz), 8.1 (d, 1H, J=7.8 Hz), 7.9 (t, 1H, J=7.5 Hz, 1.9 Hz), 7.59-7.61 (m, 5H), 7.49-7.52 (m, 2H), 7.4 (t, 1H), 7.3 (d, 2H, J=8.4 Hz), 3.7 (s, 2H), 3.1 (d, 2H), 2.9 (t, 1H), 2.4 (t, 2H), 2.1 (d, 2H), 2.0 (t, 2H).

Example 13

8-methoxy-3-phenyl-2-(4-{[4-(5-pyridin-2-yl-1,2,4-triazol-3-yl)piperidin-1-yl]methyl}phenyl)imidazo[1,2-a]pyridine Example 13 is prepared according to example 12.

MS (M+1): 542.20.

$^1$H NMR(CD$_3$OD): δ 8.64 (d, 1H, J=4.2 Hz), 8.06 (d, 1H, J=8.1 Hz), 7.91 (dt, 1H, J=7.8, 7.5 Hz), 7.5-7.7 (m, 6H), 7.42-7.44 (m, 3H), 7.33 (d, 2H, J=8.1 Hz), 6.82 (t, 1H), 6.75

(d, 1H, J=7.5 Hz), 4.06 (s, 3H), 3.83 (s, 2H), 3.1 (q, 2H), 3.03 (m, 1H), 2.57 (t, 2H), 2.12 (d, 2H), 2.02 (t, 2H).

Example 14

3-(3-fluorophenyl)-2-(4-{[4-(5-pyridin-2-yl-1,2,4-triazol-3-yl)piperidin-1-yl]methyl}phenyl)imidazo[1,2-a]pyridine Example 14 is prepared according to example 9.
MS (M+1): 530.20.
$^1$H NMR (DMSO-$d_6$): δ 8.7 (s, 1H), 8.07 (d, J=6.9 Hz, 1H), 8.0 (d, J=7.2 Hz, 1H), 8.0 (m, 1H) 7.7-7.6 (m, 2H), 7.5 (d, J=8.1 Hz, 2H), 7.4-7.2 (m, 7H), 6.9 (t, 1H), 3.5 (s, 2H), 2.9 (d, 2H), 2.6 (m, 1H), 2.1 (t, 2H), 1.9 (d, 2H), 1.8 (t, 2H).

Example 15

3-(4-methoxyphenyl)-2-(4-{[4-(5-pyridin-2-yl-1,2,4-triazol-3-yl)piperidin-1-yl]methyl}phenyl)imidazo[1,2-a]pyridine Example 15 is prepared according to example 9 by using 4-methoxyphenyl boronic acid in step1.
MS (M+1): 542.27.
$^1$H NMR(CD$_3$OD): δ 8.7 (d, 1H), 8.1 (m, 2H), 7.9 (dt, J=1.8 Hz, 7.8 Hz, 1H), 7.6-7.7 (m, 3H), 7.2-7.5 (m, 8H), 6.9 (dt, J=6.9 Hz, 1.2 Hz, 1H), 4.1 (s, 2H), 3.9 (s, 3H), 3 (m, 1H), 2.7 (t, 2H), 2.1 (m, 4H), 2.0 (m, 2H).

Example 16

3-pyridin-4-yl-2-(4-{[4-(5-pyridin-2-yl-1,2,4-triazol-3-yl)piperidin-1-yl]methyl}phenyl)imidazo[1,2-a]pyridine Step1: 4-(3-pyridin-4-ylimidazo[1,2-a]pyridin-2-yl)benzaldehyde 0.2 g (0.9 mM) 4-imidazo[1,2-a]pyridin-2-ylbenzaldehyde (prepared as described by Sundberg et al.; J. Heterocyclic Chem., 25, 129, 1988) is dissolved in 5 mL of Dioxane. To this is added CsCO$_3$ (1.1 eq), palladium acetate (8 mol %), triphenyl phosphine (16 mol %), triethylamine (2 eq) and 4-bromo-pyridine (1.4 eq). The reaction mixture is heated (microwave) for 45 min at 100° C. The reaction mixture is cooled to RT, diluted with DCM. The organic layer is washed with water, dried and concentrated. The crude product purified by column chromatography to obtain the desired compound.
MS (M+1): 300.33.
$^1$H NMR (DMSO-$d_6$): δ 10 (s, 1H), 8.8 (d, J=4.2 Hz, 2H), 8.3 (d, J=6.9 Hz, 1H), 7.9 (d, J=8.4 Hz, 2H), 7.7 (d, J=8.1 Hz, 2H), 7.6 (d, J=5.7 Hz, 2H), 7.73 (s, 1H), 7.4 (m, 1H), 7 (dt, J=6.9 Hz, 1.2 Hz, 1H).

Step 2: 3-pyridin-4-yl-2-(4-{[4-(5-pyridin-2-yl-1,2,4-triazol-3-yl)piperidin-1-yl]methyl}phenyl)imidazo[1,2-a]pyridine To a solution of 0.05 g (0.16 mM) 4-(3-pyridin-4-ylimidazo[1,2-a]pyridin-2-yl)benzaldehyde in 5 mL of THF is added triethylamine (2 eq). The reaction mixture is stirred for 5 minutes. To this solution is added 2-(5-Piperidin-[1,2,4] triazol-3-yl)-pyridine*2HCl (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 513.33.
$^1$H NMR(CD$_3$OD): δ 8.7 (d, J=1.5 Hz, 2H), 8.65 (d, J=4.8 Hz, 1H), 8.1 (d, J=6.9 Hz, 1H), 8.1 (d, J=7.8 Hz, 1H), 7.93 (dd, J=1.8 Hz, J=7.8 Hz, 1H), 7.9 (s, 1H), 7.7 (d, J=9 Hz, 1H), 7.3-7.7 (m, 8H), 7.0 (dt, J=6.9 Hz, 1.2 Hz, 1H), 3.9 (s, 2H), 3 (m, 1H), 2.7 (t, 2H), 2.1 (m, 4H), 2 (m, 2H).

Example 17

2-(4-{[4-(5-pyridin-2-yl-1,2,4-triazol-3-yl)piperidin-1-yl]methyl}phenyl)-3-(2-thienyl)imidazo[1,2-a]pyridine Example 17 is prepared according to example 9 by using 2-thienylboronic acid in step.
MS (M+1): 518.20.
$^1$H NMR(CD$_3$OD): δ 8.65 (d, J=4.2 Hz, 1H), 8.1 (t, J=6.9 Hz, 2H), 7.9 (m, 1H), 7.8 (dd J=2.1 Hz, 4.5 Hz, 1H), 7.7 (d, J=8.1 Hz, 2H), 7.6 (d, J=9.3 Hz, 1H), 7.4 (m, 4H), 7.3 (m, 2H), 7 (dt, J=6.9 Hz, 1.2 Hz, 1H), 3.9 (s, 2H), 3 (m, 1H), 2.7 (t, 2H), 2.1 (m, 4H), 2 (m, 2H).

Example 18

3-(4-fluorophenyl)-2-(4-{[4-(5-pyridin-2-yl-1,2,4-triazol-3-yl)piperidin-1-yl]methyl}phenyl)imidazo[1,2-a]pyrimidine Step1: 1-[4-(1,3-dioxolan-2-yl)phenyl]ethanone To the stirred solution of methyl magnesium chloride in ether is added 4-(1,3-dioxolan-2-yl)benzonitrile (15 g, 85.6 mM, 0.2 eq) in dry ether over a period of 15 min. The reaction mixture is stirred over night. Reaction mixture is cooled to 0° C. and slowly quenched with sat. solution of ammonium chloride. Ether is added and the separated organic layer is dried and concentrated. The crude product is purified by column chromatography to obtain the desired compound as a white solid. $^1$H NMR (CDCl$_3$): δ 2.622 (s, 3H), 4.165-4.04 (m, 4H), 5.875 (s, 1H), 7.588 (d, J=8.1 Hz, 2H), 7.987 (d, J=8.4 Hz, 2H).

Step 2: 4-(bromoacetyl)benzaldehyde 5.5 g (28.6 mM) of 1-[4-(1,3-dioxolan-2-yl)phenyl]ethanone is dissolved in acetone water mixture (200 mL). Catalytic amount of 4-methylbenzenesulfonic acid is added and the reaction mixture is refluxed for 4 h. The organic solvent is evaporated and the crude is extracted in ethylacetate. The organic layer is dried, concentrated to obtain the crude product, which is dissolved in a mixture of ethyl acetate and chloroform (100 mL). The reaction mixture is refluxed. To this is added cupric bromide (2 eq) in portions while purging N$_2$ gas. The reaction mixture is refluxed for 8 h. It is then filtered, concentrated and the crude is purified by cc to obtain the desired compound.
$^1$H NMR (DMSO-$d_6$): δ 10.12 (s, 1H), 8.18 (d, J=8.1 Hz, 2H), 8.06 (d, J=6.6 Hz, 2H), 5.09 (s, 2H).

Step 3: 4-imidazo[1,2-a]pyrimidin-2-ylbenzaldehyde 4-(bromoacetyl)benzaldehyde is dissolved in acetone. To it is added pyrimidin-2-amine (1 eq). The reaction mixture is stirred overnight. The precipitated solid is filtered off and dried to obtain the desired compound as a white solid.

MS (M+1): 224.13.

$^1$H NMR (DMSO-d$_6$): δ 10 (s, 1H), 9 (dd, J=6.6 Hz, 1.5 Hz, 1H), 8.57 (dd, J=2.1 Hz, 4.2 Hz, 1H), 8.5 (s, 1H), 8.3 (d, J=8.4 Hz, 2H), 8.0 (d, J=8.4 Hz, 2H), 7.1 (dd, J=6.6 Hz, 3.9 Hz, 1H).

Step 4: 4-(3-bromoimidazo[1,2-a]pyrimidin-2-yl) benzaldehyde

This compound 13 is prepared according to the procedure reported by Sundberg et al. (J. Heterocyclic Chem., 25, 129, 1988).

Step 5: 4-[3-(4-fluorophenyl)imidazo[1,2-a]pyrimidin-2-yl]benzaldehyde 0.225 g (0.74 mM) 4-(3-bromoimidazo[1,2-a]pyrimidin-2-yl)benzaldehyde is dissolved in 5 mL of toluene. To this mixture is added 4-fluorphenyl boronic acid (1.5 eq) followed by tetrakis triphenylphosphine palladium (0) 10% by wt, K$_2$CO$_3$ (3 eq) and ethanol water mixture (4 mL). The reaction mixture is heated at 90° C. for 4-6 h. The reaction is cooled to room temperature and 20 mL of water is added and the reaction mixture is extracted with ethyl acetate. The organic layer is dried and concentrated. The crude is purified by flash column chromatography to yield the desired compound.

MS (M+1): 318.33.

$^1$H NMR (DMSO-d$_6$): δ 10.07 (s, 1H), 8.89 (dd, J=2.1 Hz, 6.9 Hz, 1H), 8.68 (dd, J=1.8 Hz, 4.2 Hz, 1H), 8.36 (d, J=8.1 Hz, 2H), 8.08 (d, J=8.4 Hz, 2H), 7.26 (dd, J=4.2 Hz, 6.9 Hz, 1H).

Step 6: 3-(4-fluorophenyl)-2-(4-{[4-(5-pyridin-2-yl-1,2,4-triazol-3-yl)piperidin-1-yl]methyl}phenyl) imidazo[1,2-a]pyrimidine To a solution of 0.23 g (0.72 mM) 4-[3-(4-fluorophenyl) imidazo[1,2-a]pyrimidin-2-yl]benzaldehyde in 5 mL of THF is added triethylamine (2 eq). The reaction mixture is stirred for 5 minutes. To this solution is added 2-(5-Piperidin-[1,2,4]triazol-3-yl)pyridine*2HCl (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 531.27.

$^1$H NMR(CD$_3$OD): δ 8.7 (m, 2H), 8.5 (d, 1H), 8.1 (d, 1H), 7.9 (dt, J=1.8 Hz, 7.8 Hz, 1H), 7.7-7.6 (m, 3H), 7.2-7.5 (m, 8H), 6.9 (dt, J=6.9 Hz, 1.2 Hz, 1H), 3.9 (s, 2H), 3 (m, 1H), 2.7 (t, 2H), 2.1 (m, 4H), 2.0 (m, 2H).

Example 19

7-methyl-3-phenyl-2-(4-{[4-(5-pyridin-2-yl-1,2,4-triazol-3-yl)piperidin-1-yl]methyl}phenyl)imidazo[1,2-a]pyrimidine This example is prepared according to compound 12 by using 4-methylpyrimidin-2-amine in step1.

MS (M+1): 527.13.

$^1$H NMR(CD$_3$OD): δ 8.7 (s, 1H), 8.35 (d, J=6.9 Hz, 1H), 8.1 (d, J=8.1 Hz, 1H), 7.6-7.5 (m, 6H), 7.5-7.4 (m, 3H), 7.3 (d, J=7.8 Hz, 2H), 6.9 (d, J=6.9 Hz, 1H), 3.7 (s, 2H), 3.1 (m, 2H), 2.9 (m, 1H), 2.6 (s, 3H), 2.3 (m, 2H), 2.1-1.9 (m, 4H).

Example 20

3-(4-methoxyphenyl)-2-(4-{[4-(5-pyridin-2-yl-1,2,4-triazol-3-yl)piperidin-1-yl]methyl}phenyl)imidazo[1,2-a]pyrimidine This example is prepared in a manner according to example 18 by using 4-methoxyphenyl boronic acid in step5.

MS (M+1): 543.27.

$^1$H NMR(CD$_3$OD): δ 8.65 (d, J=4.2 Hz, 1H), 8.61 (dd, J=2.1 Hz, 4.2 Hz, 1H), 8.4 (dd, J=1.9 Hz, 6.9 Hz, 1H), 8.05 (d, J=7.8 Hz, 1H), 7.92 (t, 1H), 7.73 (d, J=8.1 Hz, 2H).

Example 21

6-chloro-3-phenyl-2-(4-{[4-(5-pyridin-2-yl-1,2,4-triazol-3-yl)piperidin-1-yl]methyl}phenyl)imidazo[1,2-a]pyrimidine This example is prepared in a manner according to example 12 by using 5-chloropyrimidin-2-amine in step1.

MS (M+1): 547.20, 549.20.

$^1$H NMR (CD$_3$OD): δ 8.65 (d, J=3.6 Hz, 1H), 8.60 (d, J=2.4 Hz, 1H), 8.54 (d, J=2.4 Hz, 1H), 8.06 (d, J=7.8 Hz 1H), 7.97-7.89 (m, 1H), 7.70 (d, J=8.4 Hz, 2H) 7.65-7.57 (m, 3H), 7.55-7.42 (m, 5H), 4.20 (s, 2H), 3.46 (brd, J=10.2 Hz, 2H), 3.4-3.35 (m, 1H), 3.1-2.95 (m, 2H), 2.28 (brd, 2H), 2.2-2.0 (m, 2H).

Example 22

6-fluoro-3-phenyl-2-(4-{[4-(5-pyridin-2-yl-1,2,4-triazol-3-yl)piperidin-1-yl]methyl}phenyl)imidazo[1,2-a]pyridine This example is prepared in a manner according to example 12 by using 5-fluoropyridin-2-amine in the first step.

MS (M+1): 530.27.

$^1$H NMR (CD$_3$OD): δ 8.65 (brd, J=4.2 Hz, 1H), 8.10-8.02 (m, 2H), 7.96-7.88 (m, 1H), 7.71-7.55 (m, 5H), 7.49-7.40 (m, 5H), 7.40-7.32 (m, 1H), 7.24-7.12 (m, 1H) 4.08 (s, 2H), 3.44-3.32 (m, 2H), 3.15-3.05 (m, 1H), 3.00-2.8 (m, 2H), 2.30-2.19 (m, 2H), 2.19-2.00 (m, 2H).

Example 23

6-iodo-3-phenyl-2-(4-{[4-(5-pyridin-2-yl-1,2,4-triazol-3-yl)piperidin-1-yl]methyl}phenyl)imidazo[1,2-a]pyrimidine This example is prepared in a manner according to example 12 by using 5-iodopyrimidin-2-amine in the first step.

MS (M+1): 639.13.

$^1$H NMR (CD$_3$OD): δ 8.67 (d, J=2.4 Hz, 1H), 8.64 (d, J=4.5 Hz, 1H), 8.58 (d, J=2.1 Hz, 1H), 8.07 (d, J=7.8 Hz, 1H), 7.91 (dt, J=1.8, 7.5 Hz, 1H), 7.68-7.57 (m, 5H), 7.51-7.47 (m, 2H), 7.44 (t, 1H), 7.34 (d, J=8.1 Hz, 2H), 3.8 (s, 2H), 3.11 (d, 2H), 2.90 (m, 1H), 2.42 (t, 2H), 2.15 (d, 2H), 1.96 (t, 2H).

Example 24

7-methoxy-3-phenyl-2-(4-{[4-(5-pyridin-2-yl-1,2,4-triazol-3-yl)piperidin-1-yl]methyl}phenyl)imidazo[1,2-a]pyrimidine This example is prepared in a manner according to example 12 by using 4-methoxy-2-amine in the first step. MS (M+1): 543.13.

$^1$H NMR (CD$_3$OD): δ 8.64 (d, J=4.5 Hz, 1H), 8.21 (d, J=7.2 Hz, 1H), 8.07 (d, J=8.1 Hz, 1H), 7.89 (dt, J=2.1, 7.8 Hz, 1H), 7.59-7.52 (m, 5H), 7.49-7.44 (m, 3H), 7.28 (d, J=8.4 Hz, 2H), 6.54 (d, J=7.2 Hz, 1H), 4.07 (s, 3H), 3.73 (s, 2H), 3.12 (d, 2H), 2.92 (m, 1H), 2.44 (t, 2H), 2.14 (d, 2H), 2.0 (t, 2H).

Example 25

8-bromo-3-phenyl-2-(4-{[4-(5-pyridin-2-yl-1,2,4-triazol-3-yl)piperidin-1-yl]methyl}phenyl)imidazo[1,2-a]pyridine This example is prepared in a manner according to example 12 by using 3-bromopyridin-2-amine in the first step.

MS (M+1): 590.07, 592.07.

$^1$H NMR (CD$_3$OD): δ 8.64 (d, J=4.5 Hz, 1H), 8.07 (d, J=6.6 Hz, 2H), 7.92 (dt, J=1.8 Hz, 7.8 Hz, 1H), 7.65-7.54 (m, 6H), 7.48-7.42 (m, 3H), 7.34 (d, J=8.1 Hz, 2H), 6.81 (t, 1H), 3.84 (s, 2H), 3.20 (d, 2H), 2.98 (m, 1H), 2.57 (t, 2H), 2.14 (d, 2H), 2.06 (t, 2H).

Example 26

8-chloro-3-phenyl-2-(4-{[4-(5-pyridin-2-yl-1,2,4-triazol-3-yl)piperidin-1-yl]methyl}phenyl)imidazo[1,2-a]pyrazine This example is prepared in a manner according to example 12 by using 3-chloropyrazin-2-amine in the first step.

MS (M+1): 547.20, 549.20.

$^1$H NMR (CD$_3$OD): δ 8.64 (d, J=4.8 Hz, 1H), 8.08 (t, 1H), 8.06 (s, 1H), 7.92 (dt, J=1.8, 7.8 Hz, 1H), 7.68 (t, 3H), 7.62-7.59 (m, 3H), 7.56-7.46 (m, 2H), 7.44-7.57 (m, 3H), 3.83 (s, 2H), 3.18 (d, 2H), 2.98 (m, 1H), 2.58 (t, 2H), 2.16 (d, 2H), 2.01 (t, 2H).

Example 27

8-methoxy-3-phenyl-2-(4-{[4-(5-pyridin-2-yl-1,2,4-triazol-3-yl)piperidin-1-yl]methyl}phenyl)imidazo[1,2-a]pyrazine This example is prepared in a manner according to example 12 by using 3-methoxypyrazin-2-amine in the first step.

MS (M+1): 543.07.

$^1$H NMR (CD$_3$OD): δ 8.26 (d, J=3.9 Hz, 1H), 8.06 (d, J=7.8 Hz, 1H), 7.90 (t, 1H), 7.65 (d, J=4.8 Hz, 1H), 7.55-7.53 (m, 5H), 7.45-7.38 (m, 4H), 7.29 (d, J=8.1 Hz, 2H), 4.16 (s, 3H), 3.59 (s, 2H), 3.0 (s, 2H), 2.85 (m, 1H), 2.28 (t, 2H), 2.08 (d, 2H), 1.90 (d, 2H).

Example 28

3-phenyl-2-(4-{[4-(5-pyridin-2-yl-1,2,4-triazol-3-yl)piperidin-1-yl]methyl}phenyl)-7-(trifluoromethyl)imidazo[1,2-a]pyrimidine This example is prepared in a manner according to example 12 by using 4-(trifluoromethyl)pyrimidin-2-amine in the first step.

MS (M+1): 581.13.

$^1$H NMR (CD$_3$OD): δ 8.73 (d, J=7.2 Hz, 1H), 8.65 (br d, J=3.6 Hz, 1H), 8.12-8.05 (m, 1H), 7.97-7.89 (m, 2H), 7.73-7.53 (m, 5H), 7.49-7.38 (m, 4H), 7.37-7.30 (m, 1H) 3.86 (s, 2H), 3.2-2.9 (m, 3H), 2.7-2.5 (m, 2H), 2.2-1.95 (m, 4H).

Example 29

3-phenyl-2-(4-{[4-(5-pyridin-2-yl-1,2,4-triazol-3-yl)piperidin-1-yl]methyl}phenyl)imidazo[1,2-a]pyridine-7-carbonitrile This example is prepared in a manner according to example 12 by using 2-aminoisonicotinonitrile in the first step.

MS (M+1): 537.23

$^1$H NMR (CDCl$_3$): δ 8.675 (d, J=6.5 Hz, 1H), 8.177 (d, J=8.1 Hz, 1H), 8.16 (s, 1H), 8.019 (d, J=7.2 Hz, 1H) 7.858 (t, J=7.2 Hz, 1H) 7.664 (d, J=8.1 Hz, 2H) 7.608-7.457 (m, 5H) 7.36 (d, 8.1 Hz, 2 H) 7.285 (m, 3H), 6.907 (dd, J=7.2 Hz, 1.5 Hz, 1H), 3.714 (s, 2H), 3.185-2.155 (m, 9H).

3-phenyl-2-[4-({4-[5-(pyridin-2-yl)-4H-1,2,4-triazol-3-yl]piperidin-1-yl}methyl)phenyl]imidazo[1,2-a]pyridine-7-carbonitrile (2E)-but-2-enedioate To 3.0 g 3-phenyl-2-(4-{[4-(5-pyridin-2-yl-1,2,4-triazol-3-yl)piperidin-1-yl]methyl}phenyl)imidazo[1,2-a]pyridine-7-carbonitrile (prepared as described under example 29) in 50 ml acetone is added a solution of 0.714 g fumaric acid in. The reaction mixture is stirred at ambient temperature for 3 d. The desired compound is collected by filtration and dried.

Characteristic 1H NMR (dDMSO, 300 MHz) Signals: 8.66 (d, 1H); 8.43 (s, 1H), 8.13 (d, 1H), 8.01 (d, 1H), 7.93 (t, 1H), 7.61 (m, 5H), 7.41 (t, 1H), 7.33 (d, 2H), 7.16 (d, 1H), 6.6 (2H)

Example 30

3-phenyl-2-(4-{[4-(3-pyridin-2-yl-pyrazol-5-yl)piperidin-1-yl]methyl}phenyl)imidazo[1,2-a]pyrimidine This example is prepared in a manner similar to 1 by using 2-(5-piperidin-4-yl-pyrazol-3-yl)pyridine in the last step which was prepared as described in Bioorg. Med. Chem. Lett.; EN; 12; 3; 2002; 383-386.

Analytical Data

MS (M+1): 510

Characteristic 1H NMR (400 Hz, dDMSO) signals: 8.4 ppm (d, 1H); 7.1 ppm (dd, 1H);

Example 31

6-chloro-3-phenyl-2-(4-{[4-(5-pyridin-2-yl-1,2,4-triazol-3-yl)piperidin-1-yl]methyl}phenyl)imidazo[1,2-b]pyridazine This example is prepared in a manner according to example 12 by using 6-chloropyridazin-3-amine in the first step.

MS (M+1): 547.13.

¹H NMR (300 MHz, DMSO-d₆): δ 8.65 (d, 1H), 8.278 (d, J=9.6 Hz, 1H), 8.014 (d, J=7.8 Hz, 1H), 7.92 (s, 1H), 7.59-7.51 (m, 7H), 7.41 (d, J=9.3 Hz, 3H), 7.3 (d, J=7.5 Hz, 2H), 3.49 (s, 1H), 2.86-2.73 (m, 3H), 2.07 (s, 2H) 1.97-1.76 (m, 5H).

Example 32

6-methoxy-3-phenyl-2-(4-{[4-(5-pyridin-2-yl-1,2,4-triazol-3-yl)piperidin-1-yl]methyl}phenyl)imidazo[1,2-b]pyridazine To a suspension of example 31 (0.2 g, 0.366 mM) in 15 mL of methanol is added NaOCH3 (10 eq.) and the reaction mixture is refluxed for 6 h. The reaction mixture is concentrated and quenched with water. The resulting solid is filtered and dried to obtain the desired compound.

MS (M+1): 543.13.

¹H NMR (300 MHz, CD3OD) δ 8.65 (d, J=4.2 Hz, 1H), 8.1 (d, J=8.1 Hz, 1H), 7.94-7.9 (m, 2H), 7.6-7.5 (m, 4H), 7.5-7.4 (m, 4H), 7.32 (d, J=8.1 Hz, 2H), 6.9 (d, J=9.6 Hz, 1H), 3.9 (s, 3H), 3.6 (s, 2H), 3.04-3.0 (m, 2H) 2.88-2.87 (m, 1H), 2.25-2.18 (m, 2H), 2.07-1.88 (m, 4H).

Example 33

3-phenyl-2-(4-{[4-(5-pyridin-2-yl-1,2,4-triazol-3-yl)piperidin-1-yl]methyl}phenyl)imidazo[1,2-a]pyridine-8-carboximidamide To a solution of hydroxylamine hydrochloride (10 eq) in 5 mL of anhyd. DMSO, is added, KtBuO (10 eq) at 5° C. in portions. To this is added example 5 (0.15 g, 0.28 mM). The reaction is stirred overnight. The reaction mixture is quenched with water and the resulting ppt is filtered to obtain 170 mg of crude hydroxyamidine. This is dissolved in 3 mL of acetic acid and acetic anhydride is added (0.1 mL). The reaction mixture is stirred overnight at RT. The reaction mixture is concentrated and triturated with ether to obtain acetylated hydroxyamidine. This crude is dissolved in methanol and to this is added Pd/C 10%, and the reaction mixture is stirred under hydrogen atmosphere for 2 h. After the workup, the crude is purified by prep HPLC to obtain the desired compound.

MS (M+1): 554.2.

¹H NMR (300 MHz, CD3OD) δ: 8.75 (d, J=3.3 Hz, 1H), 8.50 (s, 1H), 8.37 (d, J=6.9 Hz, 1H), 8.22 (d, J=6.6 Hz, 1H), 8.076 (d, J=7.8 Hz, 1H), 7.95-7.89 (m, 2H), 7.71-7.50 (m, 5H), 7.44 (t, 1H), 7.35 (d, J=7.8 Hz, 2H), 7.14 (t, 1H) 4.87 (s, 2H), 3.24-3.23 (d, 2H), 3.13-3.1 (d, 2H), 2.9 (m, 1H), 2.13-1.96 (m, 2H).

Example 34

2-(4-{[4-(5-pyridin-2-yl-1,2,4-triazol-3-yl)piperidin-1-yl]methyl}phenyl)-3-(3-thienyl)imidazo[1,2-a]pyrimidine This example is prepared according to example 18 by using 3-thienyl boronic acid in step5.

MS (M+1): 519.13.

¹H NMR(CD₃OD): δ 8.7 (d, J=4.8 Hz, 1H), 8.6 (m, 1H), 8.5 (dd, J=1.8, 6.9 Hz, 1H), 8.1 (d, J=8.1 Hz, 1H), 7.9 (m, 1H), 7.7 (m, 4H), 7.5 (m, 1H), 7.4 (d, J=8.1 Hz, 1H), 7.2 (dd, J=1.5, 5.1 Hz, 1H), 7 (m, 1H), 3.8 (s, 2H), 3.2 (m, 2H), 3 (m, 1H), 2.5 (m, 2H), 2.2 (m, 2H), 2 (m, 2H).

Example 35

2-(4-{[4-(5-pyridin-2-yl-1,2,4-triazol-3-yl)piperidin-1-yl]methyl}phenyl)-3-(2-thienyl)imidazo[1,2-a]pyrimidine This example is prepared according to example 18 by using 2-thienyl boronic acid in step5.

MS (M+1): 519.13.

¹H NMR(CD₃OD): δ 8.7 (dd, J=4.2, 2.1 Hz, 2H), 8.5 (dd, J=1.8, 6.6 Hz, 1H), 8.1 (d, J=8.1, 1H), 7.95 (m, 1H), 7.8 (m, 3H), 7.5 (m, 3H), 7.4 (m, 2H), 7.1 (m, 1H), 4.1 (s, 2H), 3.4 (m, 2H), 3.1 (m, 2H), 2.9 (m, 1H), 2.3 (m, 2H), 2.1 (m, 2H).

Example 36

3-pyridin-4-yl-2-(4-{[4-(5-pyridin-2-yl-1,2,4-triazol-3-yl)piperidin-1-yl]methyl}phenyl)imidazo[1,2-a]pyrimidine This example is prepared in a manner according to example 18 (first 3 steps). The final 2 steps are conducted in a manner according to step 1 & 2 from example 16.

MS (M+1): 514.2.

¹H NMR (CD₃OD): δ 8.8-8.6 (m, 5H), 8.1 (d, J=7.8 Hz, 1H), 7.9 (m, 1H), 7.7 (d, J=8.1 Hz, 2H), 7.6 (m, 4H), 7.4 (m, 1H), 7.2 (m, 1H), 4.25 (s, 2H), 3.6 (m, 2H), 3.2 (m, 2H), 3.1 (m, 1H), 2.3 (m, 2H), 2.2 (m, 2H).

Example 37

3-phenyl-2-(4-{[4-(5-pyridin-2-yl-1,2,4-triazol-3-yl)piperidin-1-yl]methyl}phenyl)imidazo[1,2-a]pyrazine To a solution of example 26 (0.1 g, 0.18 mM) in 10 mL of methanol is added 40 mg Pd/C (10%). The reaction mixture is stirred at RT under hydrogen atmosphere overnight. The reaction mixture is filtered through celite and concentrated. It is then purified by column chromatography and washed with water to obtain the desired compound.

MS (M+1): 513.20.

¹H NMR (CD₃OD): δ 9.05 (d, J=1.5 Hz, 1H), 8.64 (d, J=3.9 Hz, 1H), 8.14 (dd, J=4.8 Hz, 1.5 Hz, 1H), 8.07 (d, J=7.8 Hz, 1H), 7.94-7.87 (m, 2H), 7.68 (d, J=8.4 Hz, 2H), 7.63-7.56 (m, 3H), 7.52-7.46 (m, 3H), 7.38 (d, J=8.1 Hz, 2H), 3.81 (s, 2H), 3.19 (d, 2H), 2.98 (m, 1H), 2.51 (t, 2H), 2.21-1.92 (m, 4H).

Example 38

3-phenyl-2-(4-{[4-(5-pyridin-2-yl-1,2,4-triazol-3-yl)piperidin-1-yl]methyl}phenyl)imidazo[1,2-a]pyridine-7-carboxamide Example 29 (0.1 g, 0.018 mM) is dissolved in 3 mL of conc. H₂SO₄. It is stirred overnight and quenched with water and basified with 20% w/w NaOH solution. The precipitated out solid is filtered and dried. It is then purified by column chromatography to obtain the desired compound.

MS (M+1): 555.13.

¹H NMR (CDCl₃): δ 8.64 (d, J=4.5 Hz, 1H), 8.18 (s, 1H), 8.13 (d, J=7.2 Hz, 1H), 8.08 (d, J=7.8 Hz, 1H) 7.94 (dd, J=7.8 Hz, 1.8 Hz, 2H) 7.64-7.54 (m, 5H) 7.50-7.42 (m, 3H) 7.38-7.36 (m, 3 H) 7.33 (s, 2H), 3.30 (bs, 2H), 3.18 (d, 2H), 2.95 (m, 1H), 2.40 (m, 2H), 2.15-1.93 (m, 4H)

Example 39

2-(4-{[4-(5-pyridin-2-yl-1,2,4-triazol-3-yl)piperidin-1-yl]methyl}phenyl)-3-(1,3-thiazol-2-yl)imidazo[1,2-a]pyrimidine This example is prepared in a manner according to example 18 except step 5 where Stille coupling employing 2-(tributylstannyl)-1,3-thiazole is carried out instead of Suzuki coupling. Step 6 is according to example 18.

Step 5: 4-[3-(1,3-thiazol-2-yl)imidazo[1,2-a]pyrimidin-2-yl]benzaldehyde 0.5 g (1.65 mM) 4-(3-bromoimidazo[1,2-a]pyrimidin-2-yl)benzaldehyde is dissolved in 15 mL of 1,4-Dioxane. To this solution is added tetrakis triphenylphosphine palladium (200 mg) 40%. The reaction mixture is heated at 100° C. for 10 min. and 2-(tributylstannyl)-1,3-thiazole is added (681 mg, 1.81 mM). The reaction is heated (oil bath or microwave) at same temp for 5 h. The reaction is cooled to room temperature and 50 mL of water is added and the reaction mixture is extracted with ethyl acetate. The organic layer is dried and concentrated. The crude is purified by flash column chromatography to yield the desired product.
MS (M+1): 307.20.
$^1$H NMR (DMSO-d$_6$): δ 10.16 (s, 1H), 9.72 (dd, J=1.8, 6.9 Hz, 1H), 8.7 (dd, J=1.8, 4.2 Hz, 1H), 8.08 (d, J=3.3 Hz, 1H), 8.06 (d, J=8.1 Hz, 2H), 7.94 (d, J=8.1 Hz, 2H), 7.81 (d, J=3.3 Hz, 1H), 7.35 (m, 1H).

Step 6: 2-(4-{[4-(5-pyridin-2-yl-1,2,4-triazol-3-yl)piperidin-1-yl]methyl}phenyl)-3-(1,3-thiazol-2-yl)imidazo[1,2-a]pyrimidine MS (M+1): 520.13
$^1$H NMR (CD$_3$OD): δ 9.93 (d, J=5.1 Hz, 1H), 8.72 (dd, J=4.2, 2.1 Hz, 1H), 8.63 (d, J=4.2, 1 H), 8.092 (d, J=8.1, 1 H), 7.98 (d, J=3.3 Hz, 1H), 7.92 (t, 1H), 7.71 (d, J=8.1, 2H), 7.58 (d, J=8.1 Hz, 2H), 7.54 (d, J=3.3, 1H), 7.44 (t, 1H), 7.26 (dd, J=4.5, 7.2 Hz, 1H) 3.92 (s, 2H), 3.21 (m, 2H), 3.18 (m, 1H), 2.55 (m, 2H), 2.15 (m, 2H), 2.14 (m, 2H).

Example 40

3-phenyl-2-(4-{[4-(5-pyridin-2-yl-1,2,4-triazol-3-yl)piperidin-1-yl]methyl}phenyl)imidazo[1,2-a]pyridine-8-carboxamide This example is prepared from example 5 in a manner according to example 38.
MS (M+1): 555.13.
$^1$H NMR (CD$_3$OD): δ 8.63 (d, J=5 Hz, 1H), 8.19-8.13 (m, 2H), 8.07 (d, J=7.8 Hz, 1H), 7.93-7.87 (m, 1H), 7.65 (d, J=8.4 Hz, 2H), 7.62-7.56 (m, 3H), 7.51-7.48 (m, 2H), 7.44-7.40 (m, 1H), 7.29 (d, J=8.4 Hz, 2H), 7.01 (t, 1H) 3.56 (s, 2H) 3.05-2.98 (br d, 1H), 2.91-2.78 (m, 1H), 2.23-2.11 (m, 2H), 2.070-1.950 (m, 3H), 1.950-1.911 (m, 2H).

Example 41

3-(2-fluorophenyl)-2-(4-{[4-(5-pyridin-2-yl-1,2,4-triazol-3-yl)piperidin-1-yl]methyl}phenyl)imidazo[1,2-a]pyrimidine This example is prepared according to example 9 using 2-fluorophenyl boronic acid in step 1.

MS (M+1): 531.13.
$^1$H NMR(CD$_3$OD): δ 8.64 (dd, J=4.2, 1.2 Hz, 2H), 8.39 (dd, J=6.9, 2.1 Hz, 1H), 8.01 (d, J=7.8 Hz, 1H), 7.93 (dt, J=7.8, 1.8 Hz, 1H), 7.6-7.7 (m, 3H), 7.2-7.5 (m, 6H), 7.02 (dd, J=6.9, 1.2 Hz, 1H), 3.65 (s, 2H), 3.18 (d, 2H), 2.9 (m, 1H), 2.06 (t, 2H), 1.9 (d, 2H), 1.8 (d, 2H)

Example 42

6-(4-{[4-(5-pyridin-2-yl-1,2,4-triazol-3-yl)piperidin-1-yl]methyl}phenyl)-5-(1,3-thiazol-2-yl)imidazo[2,1-b][1,3]thiazole Step 1: 4-Imidazo[2,1-b]thiazol-6-yl-benzaldehyde 0.7 g (2.1 mM) 4-(2-Bromo-acetyl)-benzaldehyde and 2-aminothiazole (2 eq) are stirred in 15 ml DMF at 90° C. for 6 h. The DMF is evaporated and the residue suspended in ethyl acetate over night. The desired product is collected by filtration.
MS (M+1): 229.13
1H NMR (DMSO-d6): d 10.0 (s, 1H), 8.51 (s, 1H), 8.06 (d, J=8.2 Hz, 2H), 8.04 (d, J=4.5 Hz, 1H), 7.9 (d, J=8.4 Hz, 2H), 7.40 (d, 1J=4.5 Hz, 1H).

Step 2: 4-(5-Bromo-imidazo[2,1-b]thiazol-6-yl)-benzaldehyde

4-Imidazo[2,1-b]thiazol-6-yl-benzaldehyde (3.8 g, 14.9 mM) is dissolved in 30 mL acetic acid. A solution of bromine (1.1 eq) in acetic acid (15 mL) is added to the reaction mixture. The reaction mixture is stirred for 3 h at room temperature. The solid obtained is collected by filtration and re-dissolved in water (100 ml) and the solution neutralized by aqueous ammonia. The solid obtained is collected by filtration and dried.
MS (M+1): 307.13, 309.1
1H NMR (DMSO-d6): d 10.03 (s, 1H), 8.2 (d, J=8.4 Hz, 2H), 8.0 (d, J=8.4 Hz, 2H), 7.95 (d, J=4.5 Hz, 1H), 7.48 (d, J=4.5 Hz, 1H).

Step 3: (5-Thiazol-2-yl-imidazo[2,1-b]thiazol-6-yl)-benzaldehyde 4-(5-Bromo-imidazo[2,1-b]thiazol-6-yl)-benzaldehyde 0.09 g (0.37 mM) is dissolved in 5 mL of 1,4 dioxane and 0.5 eq of Pd(PPh3)4 is added followed by the addition of 2-(tributylstannyl)-1,3-thiazole (1.1 eq) and the reaction mixture is heated to reflux for 24 h. The reaction mixture is cooled down to room temperature and diluted with 10 mL of methylene chloride and 15 mL of water. The separated organic layer is washed with water and dried over Na2SO4. The crude reaction mixture is used for next step.
MS (M+1): 312.1

Step 4: 6-(4-{[4-(5-pyridin-2-yl-1,2,4-triazol-3-yl)piperidin-1-yl]methyl}phenyl)-5-(1,3-thiazol-2-yl)imidazo[2,1-b][1,3]thiazole To a solution of 0.1 g (0.31 mM) 4-(5-Thiazol-2-yl-imidazo[2,1-b]thiazol-6-yl)benzaldehyde in 5 mL of THF is added triethylamine (2 eq). The reaction mixture is stirred for 5 minutes. To this solution is added 2-(5-Piperidin-[1,2,4]triazol-3-yl)pyridine*2HCl (1.5 eq) followed by acetic acid (2.5 eq). The reaction mixture is stirred for 10 minutes. To this mixture is added NaBH(OAc)3 (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column to obtain the desired compound.

Mass (M+1): 525.13

1H NMR(CD3OD): d 8.64 (s, 1H), 8.55 (d, J=4.5 Hz, 1H), 8.08 (d, J=9.6 Hz, 1H), 9.92 (t, J=9.3, 9.2 Hz, 1H), 7.84 (d, J=3.3 Hz, 1H), 7.66 (d, J=6.6 Hz, 2H), 7.53 (d, J=7.8 Hz, 2H), 7.4 (d, J=3.3 Hz, 2H), 7.30 (d, J=4.5 Hz, 1H), 3.8 (s, 2H), 3.2 (d, 2H), 3.0 (m, 1H), 2.5 (t, 2H), 2.14 (d, 2H), 2.00 (d, 2H).

Example 43

5-(1,3-oxazol-2-yl)-6-(4-{[4-(5-pyridin-2-yl-4H-1,2,4-triazol-3-yl)piperidin-1-yl]methyl}phenyl)imidazo[2,1-b][1,3]thiazole This example is prepared according to example 42 by using 2-(tributylstannyl)-1,3-oxazole in step 3.

MS (M+1): 509.13.

$^1$H NMR (CD$_3$OD): δ 8.62 (d, J=4.5 Hz, 1H), 8.41 (d, J=4.5 Hz, 1H), 8.07 (d, J=7.8 Hz, 1H), 7.9 (m, 2H), 7.81 (d, 2H, J=8.1 Hz), 7.49-7.41 (m, 3H), 7.34 (d, J=4.2 Hz, 2H), 3.7 (s, 2H), 3.19 (d, 2H), 3.0 (m, 1H), 2.4 (t, 2H), 2.1 (d, 2H), 2.0 (d, 2H).

Example 44

6,8-Difluoro-3-phenyl-2-{4-[4-(5-pyridin-2-yl-4H-[1,2,4]triazol-3-yl)-piperidin-1-ylmethyl]-phenyl}-imidazo[1,2-a]pyridine Example 44 is prepared according to example 12

MS (M+1): 548.20

1H NMR (300 MHz, CD3OD): δ 8.64 (dd, J=4.2, 1.2 Hz, 2H), 8.39 (dd, J=6.9, 2.1 Hz, 1H), 8.01 (d, J=7.8 Hz, 1H), 7.93 (dt, J=7.8, 1.8 Hz, 1H), 7.6-7.7 (m, 3H), 7.2-7.5 (m, 6H), 7.02 (dd, J=6.9, 1.2 Hz, 1H), 3.65 (s, 2H), 3.18 (d, 2H), 2.9 (m, 1H), 2.06 (t, 2H), 1.9 (d, 2H), 1.8 (d, 2H)

Example 45

2-methyl-5-phenyl-6-[4-({4-[5-(pyridin-2-yl)-4H-1,2,4-triazol-3-yl]piperidin-1-yl}methyl)phenyl]imidazo[2,1-b][1,3,4]thiadiazole Example 45 is prepared according to example 12

MS (M+1): 533.13

1H NMR (300 MHz, CDCl3) δ 8.67 (d, J=3 Hz, 1H), 8.17 (d, J=6 Hz, 1H), 7.9-7.2 (m, 12H), 3.6 (s, 2H), 3.1-2.8 (m, 3H), 2.71 (s, 3H), 2.4-1.9 (m, 6H).

Example 46

2-methyl-5-phenyl-6-[4-({4-[5-(pyridin-2-yl)-4H-1,2,4-triazol-3-yl]piperidin-1-yl}methyl)phenyl]imidazo[2,1-b][1,3]thiazole Example 46 is prepared according to example 12

MS (M+1): 532.13

$^1$H NMR (300 MHz, CDCl$_3$) δ 8.651 (d, 1H), 8.089 (d, J=7.8, Hz 1H), 7.954 (t, J=1.5 Hz 1H), 7.523-7.456 (m, 7H), 7.377-7.217 (m, 4H), 3.760 (s, 2H), 3.082 (d, J=7.8 Hz, 2H), 2.981-2.943 (m, 1H), 2.457 (s, 2H), 2.45 (s, 3H) 2.243-2.125 (m, 4H).

Example 47

2-(methylsulfanyl)-5-phenyl-6-[4-({4-[5-(pyridin-2-yl)-4H-1,2,4-triazol-3-yl]piperidin-1-yl}methyl)phenyl]imidazo[2,1-b][1,3,4]thiadiazole Example 47 is prepared according to example 12

MS (M+1): 565.07

$^1$H NMR (300 MHz, CDCl$_3$):—δ 8.672 (d, J=3.9 Hz, 1H), 8.163 (d, J=7.8 Hz, 1H), 7.828 (t, J=1.2 Hz 1H), 7.637-7.561 (m, 4H), 7.448-7.338 (m, 4H), 7.288 (d, J=8.4 Hz, 2H), 3.552 (s, 2H), 3.012 (d, J=11.1 Hz, 2H), 2.873 (m, 1H), 2.73 (s, 3H), 2.195-1.970 (m, 6H).

Example 48

5-phenyl-6-[4-({4-[5-(pyridin-2-yl)-4H-1,2,4-triazol-3-yl]piperidin-1-yl}methyl) phenyl]-2-(trifluoromethyl)imidazo[2,1-b][1,3,4]thiadiazole Example 48 is prepared according to example 12

MS (M+1): 587.05

$^1$H NMR (300 MHz, CDCl$_3$):—δ 8.683 (d, J=4.5 Hz, 1H), 8.177 (d, J=7.8 Hz, 1H), 7.852 (t, J=1.5 Hz 1H), 7.643 (s, 2H), 7.616 (s, 2H), 7.511-7.439 (m, 3H), 7.402-7.32 (m, 3H), 3.637 (s, 2H), 3.065 (d, J=11.1 Hz, 1H), 2.928 (bs, 1H), 2.243-2.067 (m, 6H).

Example 49

3-phenyl-2-[4-({4-[5-(pyridin-2-yl)-4H-1,2,4-triazol-3-yl]piperidin-1-yl}methyl)phenyl]imidazo[1,2-a]pyridine-7-carbonitrile (2Z)-but-2-enedioate To 3.0 g 3-phenyl-2-(4-{[4-(5-pyridin-2-yl-1,2,4-triazol-3-yl)piperidin-1-yl]methyl}phenyl)imidazo[1,2-a]pyridine-7-carbonitrile (prepared as described under example 29) in 50 ml acetone is added a solution of 0.714 g malonic acid in 10 ml acetone dropwise. The reaction mixture is stirred at ambient temperature for 18 h. The desired compound is collected by filtration and dried. Characteristic 1H NMR (dDMSO, 300 MHz) Signals: 8.68 (d, 1H); 8.44 (s, 1H), 8.15 (d, 1H), 8.01 (d, 1H), 7.90 (t, 1H), 7.70 (m, 5H), 7.63 (t, 1H), 7.47 (d, 2H), 7.18 (d, 1H), 6.0 (2H)

Example 50

7-methyl-3-phenyl-2-[4-({4-[5-(pyridin-2-yl)-4H-1,2,4-triazol-3-yl]piperidin-1-yl}methyl) phenyl]imidazo[1,2-a]pyridine Example 50 is prepared according to example 12

MS (M+1): 526.13

$^1$H NMR (300 MHz, CDCl$_3$):—δ 8.65 (bs, 1H), 8.02 (d, J=7.5 Hz, 1H), 7.9 (d, J=7.2 Hz, 1H), 7.46-7.60 (m, 7H), 7.42 (s, 1H), 7.22 (d, J=8.1 Hz, 2H), 3.45 (s, 2H), 2.9 (d, 2H), 2.37 (s, 3H), 1.71-2.07 (m, 6H)

Example 51

2-ethyl-5-phenyl-6-(4-{[4-(5-pyridin-2-yl-4H-1,2,4-triazol-3-yl)piperidin-1-yl]methyl}phenyl)imidazo[2,1-b][1,3,4]thiadiazole Example 41 is prepared according to example 12

MS (M+1): 547.07

$^1$H NMR (300 MHz, CDCl$_3$):—δ 8.67 (s, 1H), 8.18 (d, J=7.5 Hz, 1H), 7.9-7.25 (m, 12H), 3.56 (s, 2H), 3.1-2.8 (m, 3H), 2.3-1.9 (m, 6H), 1.43 (t, J=7.5 Hz, 3H), 0.9 (m, 2H)

Example 52

'6-bromo-3-phenyl-2-(4-{[4-(5-pyridin-2-yl-4H-1,2,4-triazol-3-yl]piperidin-1-yl]methyl}phenyl)imidazo[1,2-a]pyridine-7-carbonitrile Example 52 is prepared according to example 12
MS (M+1): 417.07
$^{1}$H NMR (300 MHz, CDCl$_{3}$):—δ 8.7 (s, 1H), 8.0-8.2 (m, 4H), 7.8 (m, 1H), 7.5-7.7 (m, 4H), 7.2-7.4 (m, 5H), 3.9 (s, 2H), 3-3.3 (m, 3H), 2-2.6 (m, 6H).

Example 53

'6-methyl-3-phenyl-2-(4-{[4-(5-pyridin-2-yl-4H-1,2,4-triazol-3-yl]piperidin-1-yl]methyl}phenyl)imidazo[1,2-b]pyridazine Example 53 is prepared according to example 12
MS (M+1): 527.13
$^{1}$H NMR (300 MHz, CDCl$_{3}$):—δ 8.6 (m, 1H), 8.1 (m, 1H), 7.8-7.9 (m, 2H), 7.7 (d, 2H), 7.6 (d, 2H), 7.3-7.5 (m, 6H), 6.9 (d, 1H), 3.9 (s, 2H), 3.0-3.3 (m, 3H), 2.5 (s, 3H), 2.0-2.3 (m, 6H).

Example 54

7-chloro-3-phenyl-2-(4-{[4-(5-pyridin-2-yl-4H-1,2,4-triazol-3-yl]piperidin-1-yl]methyl}phenyl)imidazo[1,2-a]pyridine Example 54 is prepared according to example 12
MS (M+1): 546.13
$^{1}$H NMR (300 MHz, CDCl$_{3}$):—δ 8.7 (d, J=4.5 Hz, 1H), 8.1 (d, J=8.1 Hz, 1H), 7.8-7.9 (m, 2H), 7.6-7.7 (m, 3H), 7.5-7.6 (m, 3H), 7.3-7.5 (m, 5H), 6.7 (d, 1H), 3.9 (s, 2H), 3.0-3.3 (m, 3H), 2.1-2.8 (m, 6H)

Example 55

'3-phenyl-2-(4-{[4-(5-pyridin-4-yl-1H-1,2,4-triazol-3-yl) piperidin-1-yl]methyl}phenyl)imidazo[1,2-a]pyrimidine To a solution of 0.094 g (0.314 mM) 4-(3-phenylimidazo[1,2-a]pyrimidin-2-yl)benzaldehyde in 3 mL of THF is added triethylamine (2 eq). The reaction mixture is stirred for 5 minutes. To this solution is added 4-[3-(piperidin-4-yl)-1H-1,2,4-triazol-5-yl]pyridine 2HCl (1.5 eq) (Intermediate B) followed by acetic acid (2.5 eq). The reaction mixture is stirred for 10 minutes. To this mixture is added NaBH(OAc)$_{3}$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 513.2
$^{1}$H NMR (300 MHz, CDCl$_{3}$):—δ 8.66 (d, J=5.7 Hz, 2H), 8.576 (s, 1H), 8.28 (dd, J=6.6, 1.5 Hz 1H), 7.98 (d, J=6 Hz, 2H), 7.65 (d, J=8.1 Hz 2H), 7.54 (d, J=6.3 Hz, 3H), 7.457-7.431 (m, 2H), 7.265-7.216 (m, 2H), 6.880-6.843 (m, 1H) 3.57 (s, 2H), 2.97 (d, J=10.8 Hz, 3H) 2.182-2.094 (m, 2H), 1.992-1.910 (m, 4H).

Example 56

'5-phenyl-6-(4-{[4-(5-pyridin-4-yl-4H-1,2,4-triazol-3-yl)piperidin-1-yl]methyl}phenyl)imidazo[2,1-b][1,3]thiazole Example 56 is prepared according to example 55
MS (M+1): 518.0
$^{1}$H NMR (300 MHz, DMSO-d$_{6}$) δ 8.63 (d, J=6 Hz, 2H), 7.88 (d, J=4.5 Hz, 2H), 7.70 (d, J=4.5 Hz, 1H), 7.55-7.15 (m, 11H), 3.46 (s, 2H), 3.0-2.7 (m, 3H), 2.2-1.7 (m, 6H).

Example 57

'3-phenyl-2-(4-{[4-(3-pyridin-4-yl-1H-1,2,4-triazol-5-yl)piperidin-1-yl]methyl}phenyl)imidazo[1,2-a]pyridine-7-carbonitrile Example 57 is prepared according to example 55
MS (M+1): 537.13
$^{1}$H NMR (300 MHz, CDCl$_{3}$):—δ 8.69 (dd, J=4.5 Hz, 1.2 Hz, 2H), 8.123 (s, 1H), 8.011 (dd, J=7.2 Hz, 0.9 Hz, 1H), 7.95 (dd, J=4.5 Hz, 1.5 Hz, 2H), 7.63 (d, J=8.1 Hz, 2H), 7.60-7.52 (m, 2H), 7.46-7.4 (m, 2H), 7.30 (d, J=8.4 Hz, 2H) 6.90 (dd, J=6.9 Hz, 1.5 Hz, 1H), 3.60 (m, 3H), 2.44-1.91 (m, 7H)

Example 58

'3-phenyl-2-(4-{[4-(5-pyridin-4-yl-4H-1,2,4-triazol-3-yl)piperidin-1-yl]methyl}phenyl)imidazo[1,2-a]pyridine Example 58 is prepared according to example 55
MS (M+1): 512.07
$^{1}$H NMR (300 MHz, CDCl$_{3}$):—δ 8.7 (d, 2H), 8 (m, 3H), 7.7 (d, 1H), 7.4 to 7.6 (m, 7H), 7.1 to 7.3 (m, 3H), 6.8 (t, 1H), 3.6 (s, 2H), 2.7 to 2.9 (m, 3H), 1.7 to 2.2 (m, 6H).

Example 59

'3-phenyl-2-(4-{[4-(5-pyridin-4-yl-4H-1,2,4-triazol-3-yl)piperidin-1-yl]methyl}phenyl)imidazo[1,2-a]pyridine-8-carbonitrile Example 59 is prepared according to example 55
MS (M+1): 537.13
$^{1}$H NMR (300 MHz, CDCl$_{3}$):—δ 8.7 (d, 2H), 8.2 (d, 1H), 8 (d, 1H), 7.2-7.7 (m, 10H), 6.8 (t, 1H), 3.5 (s, 2H), 2.8-3.1 (m, 3H), 1.8-2.3 (m, 6H).

Example 60

'5-phenyl-6-(4-{[4-(5-pyridin-4-yl-4H-1,2,4-triazol-3-yl)piperidin-1-yl]methyl}phenyl)imidazo[2,1-b][1,3,4]thiadiazole Example 60 is prepared according to example 55
MS (M+1): 519.0
$^{1}$H NMR (300 MHz, DMSO-d$_{6}$) δ 9.22 (s, 1H), 8.65 (d, J=4.5 Hz, 2H), 7.87 (d, J=4.5 Hz, 2H), 7.6-7.3 (m, 7H), 7.26 (d, J=8.1 Hz, 2H), 3.47 (s, 2H), 2.95-2.75 (m, 3H), 2.15-1.7 (m, 6H)

Example 61

2-[4-({4-[5-(6-methylpyridin-2-yl)-4H-1,2,4-triazol-3-yl]piperidin-1-yl}methyl) phenyl]-3-phenylimidazo[1,2-a]pyridine-7-carbonitrile To a solution of 0.150 g (0.464 mM) 2-(4-formylphenyl)-3-phenylimidazo[1,2-a]pyridine-7-carbonitrile in 3 mL of THF is added triethylamine (2 eq). The reaction mixture is stirred for 5 minutes. To this solution is added 2-methyl-4-[3-(piperidin-4-yl)-1H-1,2,4-triazol-5-yl]pyridine dihydrochloride (Intermediate C) (1.5 eq) followed by acetic acid (2.5 eq). The reaction mixture is stirred for 10 minutes. To this mixture is added $NaBH(OAc)_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 551.2
$^1$H NMR (300 MHz, $CDCl_3$):—δ 8.15 (s, 1H), 7.9 (m, 2H), 7.7 (m, 3H), 7.55 (m, 3H), 7.45 (m, 2H), 7.3 (d, J=8.1 Hz, 2H), 7.2 (d, J=7.5 Hz, 1H), 6.9 (d, 1H), 3.6 (s, 2H), 3 (d, 2H), 2.9 (m, 1H), 2.5 (s, 3H), 2 to 2.6 (m, 6H).

Example 62

2-[4-({4-[5-(6-methylpyridin-2-yl)-4H-1,2,4-triazol-3-yl]piperidin-1-yl}methyl) phenyl]-3-phenylimidazo[1,2-a]pyridine-8-carbonitrile Example 62 is prepared according to example 61
MS (M+1): 551.2
$^1$H NMR (300 MHz, $CDCl_3$):—δ 8.15 (d, J=7.2 Hz, 1H), 7.9 (d, J=7.8 Hz, 1H), 7.7 (m, 4H), 7.55 (m, 3H), 7.45 (m, 2H), 7.3 (d, J=8.1 Hz, 2H), 7.2 (d, J=7.5 Hz, 1H), 6.8 (t, 1H), 3.7 (s, 2H), 3.1 (m, 2H), 2.9 (m, 1H), 2.6 (s, 3H), 2 to 2.6 (m, 6H).

Example 63

2-[4-({4-[5-(6-methylpyridin-2-yl)-4H-1,2,4-triazol-3-yl]piperidin-1-yl}methyl) phenyl]-3-phenylimidazo[1,2-a]pyrimidine Example 63 is prepared according to example 61
MS (M+1): 527.2
$^1$H NMR (300 MHz, $CDCl_3$):—δ 8.237 (dd, J=6.6, 1.8 Hz, 1H), 7.938 (d, J=7.5 Hz, 1H), 7.751-7.668 (m, 3H), 7.598-7.525 (m, 3H), 7.47-7.439 (m, 2H), 7.30 (d, J=8.1 Hz, 2H), 7.193 (d, J=7.5 Hz, 1H), 6.835-6.799 (m, 1H), 3.665 (s, 2H) 3.088-2.938 (m, 3H), 2.583 (s, 3H), 2.351 (t, J=7.8 Hz, 2H), 2.121-2.025 (m, 4H).

Example 64

2-[4-({4-[5-(6-methylpyridin-2-yl)-4H-1,2,4-triazol-3-yl]piperidin-1-yl}methyl) phenyl]-3-phenylimidazo[1,2-a]pyridine Example 64 is prepared according to example 61
MS (M+1): 526.1
$^1$H NMR (300 MHz, $CDCl_3$):—δ 8 (m, 2H), 7.6 to 7.8 (m, 4H), 7.4 to 7.6 (m, 5H), 7.1 to 7.4 (m, 4H), 6.7 (t, 1H), 3.6 (s, 2H), 2.8 to 3.1 (m, 3H), 2.5 (s, 3H), 1.8 to 2.4 (m, 6H).

Example 65

'8-methoxy-2-[4-({4-[5-(6-methylpyridin-2-yl)-4H-1,2,4-triazol-3-yl]piperidin-1-yl}methyl)phenyl]-3-phenylimidazo[1,2-a]pyrazine Example 65 is prepared according to example 61
MS (M+1): 557.13
$^1$H NMR (300 MHz, $CDCl_3$):—δ 8 (d, J=7.8 Hz, 1H), 7.65-7.75 (m, 3H), 7.49-7.57 (m, 4H), 7.4-7.48 (m, 2H), 7.27-7.35 (m, 2H), 7.2 (d, J=7.8 Hz, 1H), 4.2 (s, 2H), 3.7 (s, 2H), 2.8-3.2 (m, 3H), 2.6 (s, 3H), 2-2.3 (m, 4H).

Example 66

'6-[4-({4-[5-(6-methylpyridin-2-yl)-4H-1,2,4-triazol-3-yl]piperidin-1-yl}methyl)phenyl]-5-phenylimidazo[2,1-b][1,3]thiazole Example 66 is prepared according to example 61
MS (M+1): 532.07
$^1$H NMR (300 MHz, $CDCl_3$):—δ 7.94 (d, J=7.5 Hz, 1H), 7.75-7.15 (m, 13H), 6.81 (d, J=4.2 Hz, 1H), 3.52 (s, 2H), 3.05-2.75 (m, 3H), 2.58 (s, 3H), 2.2-1.8 (m, 6H).

Example 67

'6-[4-({4-[5-(6-methylpyridin-2-yl)-4H-1,2,4-triazol-3-yl]piperidin-1-yl}methyl)phenyl]-5-phenylimidazo[2,1-b][1,3,4]thiadiazole Example 67 is prepared according to example 61
MS (M+1): 533.13
$^1$H NMR (300 MHz, $CDCl_3$):—δ 8.54 (s, 1H), 7.94 (d, J=7.5 Hz, 1H), 7.75-7.55 (m, 4H), 7.5-7.15 (m, 8H), 3.58 (s, 2H), 3.1-2.8 (m, 3H), 2.58 (s, 3H), 2.4-1.9 (m, 6H).

Example 68

'7-methoxy-2-[4-({4-[5-(6-methylpyridin-2-yl)-4H-1,2,4-triazol-3-yl]piperidin-1-yl}methyl)phenyl]-3-phenylimidazo[1,2-a]pyridine Example 68 is prepared according to example 61
MS (M+1): 557.3
$^1$H NMR (300 MHz, $CDCl_3$):—δ 8 (m, 2H), 7.65 to 7.75 (m, 3H), 7.4 to 7.6 (m, 5H), 7.1 to 7.3 (m, 3H), 6.4 (d, 1H), 4.1 (s, 3H), 3.6 (s, 2H), 2.8 to 3.1 (m, 3H), 2.5 (s, 3H), 1.9 to 2.4 (m, 6H).

Example 69

6-methyl-2-[4-({4-[5-(6-methylpyridin-2-yl)-4H-1,2,4-triazol-3-yl]piperidin-1-yl}methyl) phenyl]-3-phenylimidazo[1,2-b]pyridazine (467395)

Example 69 is prepared according to example 61
MS (M+1): 541.13
$^1$H NMR (300 MHz, $CDCl_3$):—δ 7.85 to 7.95 (m, 2H), 7.55 to 7.75 (m, 5H), 7.4 to 7.5 (m, 3H), 7.3 to 7.4 (m, 2H), 7.2 (d, 1H), 6.9 (d, 1H), 3.7 (s, 2H), 2.9 to 3.1 (m, 3H), 2.6 (s, 3H), 2.5 (s, 3H), 2 to 2.3 (m, 6H).

Example 70

'2-[4-({4-[5-(5-methylpyridin-2-yl)-4H-1,2,4-triazol-3-yl]piperidin-1-yl}methyl) phenyl]-3-phenylimidazo[1,2-a]pyrimidine To a solution of 0.110 g (0.367 mM) 4-(3-phenylimidazo[1,2-a]pyrimidin-2-yl)benzaldehyde in 3 mL of THF is added triethylamine (2 eq). The reaction mixture is stirred for 5 minutes. To this solution is added 5-methyl-2-[3-(piperidin-4-yl)-1H-1,2,4-triazol-5-yl]pyridine dihydrochloride (Intermediate D) (1.5 eq) followed by acetic acid (2.5 eq). The reaction mixture is stirred for 10 minutes. To this mixture is added $NaBH(OAc)_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound
MS (M+1): 527.13
$^1$H NMR (300 MHz, CDCl$_3$):—δ 8.57-8.55 (q, 1H), 8.43 (bs, 1H), 8.23 (dd, J=6.9, 1.8 Hz, 1H), 8.04 (d, J=8.1 Hz, 2H), 7.64-7.59 (m, 1H), 7.58-7.52 (m, 3H), 7.49-7.47 (m, 2H), 7.30 (d, J=8.4 Hz 2H), 6.83-6.79 (q, 1H), 3.63 (s, 2H), 3.06 (d, 2H), 2.91 (bs, 1H), 2.39 (s, 3H), 2.72 (bs, 1H), 2.10-1.87 (m, 4H).

Example 71

'2-[4-({4-[5-(5-methylpyridin-2-yl)-4H-1,2,4-triazol-3-yl]piperidin-1-yl}methyl) phenyl]-3-phenylimidazo[1,2-a]pyridine-8-carbonitrile Example 71 is prepared according to example 70
MS (M+1): 551.2
$^1$H NMR (300 MHz, CDCl$_3$):—δ 8.5 (s, 1H), 8.1 (d, J=6.9 Hz, 1H), 8 (d, J=8.1 Hz, 1H), 7.6 to 7.7 (m, 4H), 7.5 to 7.6 (m, 3H), 7.4 to 7.5 (m, 2H), 7.3 (m, 2H), 6.8 (d, 1H), 3.6 (s, 2H), 2.8 to 3.1 (m, 3H), 2.4 (s, 3H), 1.9 to 2.2 (m, 6H)

Example 72

'2-[4-({4-[5-(5-methylpyridin-2-yl)-4H-1,2,4-triazol-3-yl]piperidin-1-yl}methyl) phenyl]-3-phenylimidazo[1,2-a]pyridine-7-carbonitrile Example 72 is prepared according to example 70
MS (M+1): 551.27
$^1$H NMR (300 MHz, DMSO-d$^6$) δ 8.50 (bs, 1H), 8.45 (s, 1H), 8.13 (dd, J=7.2 Hz, 0.9 Hz, 1H), 7.92 (d, J=8.1 Hz, 1H), 7.75 (bs, 1H), 7.67-7.53 (m, 7H), 7.28 (d, J=8.4 Hz, 2H), 7.17 (dd, J=7.2 Hz, 1.8 Hz, 1H) 3.47- (s, 2H), 2.87-2.72 (m, 3H), 2.11-1.74 (m, 6H)

Example 73

'6-[4-({4-[5-(5-methylpyridin-2-yl)-4H-1,2,4-triazol-3-yl]piperidin-1-yl}methyl)phenyl]-5-phenylimidazo[2,1-b][1,3]thiazole Example 73 is prepared according to example 70
MS (M+1): 532.07
$^1$H NMR (300 MHz, CDCl$_3$):—δ 8.47 (s, 1H), 8.04 (d, J=7.8 Hz, 1H), 7.65-7.2 (m, 12H), 6.81 (d, J=4.5 Hz, 1H), 3.58 (s, 2H), 3.1-2.8 (m, 3H), 2.39 (s, 3H), 2.3-1.9 (m, 6H)

Example 74

'6-[4-({4-[5-(5-methylpyridin-2-yl)-4H-1,2,4-triazol-3-yl]piperidin-1-yl}methyl) phenyl]-5-phenylimidazo[2,1-b][1,3,4]thiadiazole Example 74 is prepared according to example 70
MS (M+1): 533.07
$^1$H NMR (300 MHz, CDCl$_3$):—δ 8.53 (s, 1H), 8.47 (s, 1H), 8.04 (d, J=7.8 Hz, 1H), 7.68-7.25 (m, 11H), 3.57 (s, 2H), 3.1-2.8 (m, 3H), 2.39 (s, 3H), 2.3-1.9 (m, 6H)

Example 75

'2-[4-({4-[5-(5-chloropyridin-2-yl)-1H-1,2,4-triazol-3-yl]piperidin-1-yl}methyl) phenyl]-3-phenylimidazo[1,2-a]pyridine-8-carbonitrile To a solution of 0.230 g (0.712 mM) of 2-(4-formylphenyl)-3-phenylimidazo[1,2-a]pyridine-8-carbonitrile in 5 mL of THF is added triethylamine (2 eq). The reaction mixture is stirred for 5 minutes. To this solution is added 5-chloro-2-[3-(piperidin-4-yl)-1H-1,2,4-triazol-5-yl]pyridine dihydrochloride (Intermediate E) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 571.2
$^1$H NMR (300 MHz, CDCl$_3$):—δ 8.61 (bs, 1H), 8.11 (t, 2H), 7.78-7.58 (m, 2H), 7.71-7.7.43 (m, 6H), 7.28-7.17 (m, 4 H), 6.85 (t, 1H), 4.88 (bs, 1H), 3.55 (s, 2H), 2.97 (3H), 2.21-1.7 (m, 5H).

Example 76

'2-[4-({4-[5-(5-chloropyridin-2-yl)-4H-1,2,4-triazol-3-yl]piperidin-1-yl}methyl) phenyl]-3-phenylimidazo[1,2-a]pyrimidine Example 76 is prepared according to example 75
MS (M+1): 547.07
$^1$H NMR (300 MHz, CDCl$_3$):—δ 8.612 (bs, 1H), 8.55 (q, 1H), 8.24 (dd, J=2.1 Hz, 6.9 Hz, 1H), 8.10 (d, J=8.4 Hz, 1H), 7.75 (dd, J=2.1, 8.4 Hz, 1H), 7.68 (d, J=8.1 Hz, 2H), 7.58-7.52 (m, 3H), 7.48-7.431 (m, 2H), 7.26-7.22 (m, 2H), 6.82 (q, 1H), 3.52 (s, 2H), 2.98-2.86 (m, 3H), 2.157-1.95 (m, 6H).

Example 77

3-phenyl-2-[4-({4-[5-(pyrimidin-2-yl)-4H-1,2,4-triazol-3-yl]piperidin-1-yl}methyl) phenyl]imidazo[1,2-a]pyridine-8-carbonitrile To a solution of 0.130 g (0.582 mM) of 2-(4-formylphenyl)-3-phenylimidazo[1,2-a]pyridine-8-carbonitrile in 4 mL of THF is added triethylamine (2 eq). The reaction mixture is stirred for 5 minutes. To this solution is added 2-[3-(piperidin-4-yl)-1H1,2,4-triazol-5-yl]pyrimidine
Dihydrochloride (Intermediate F) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 538.2
$^1$H NMR (300 MHz, CDCl$_3$):—δ 8.15 (s, 1H), 7.9 (m, 2H), 7.7 (m, 3H), 7.55 (m, 3H), 7.45 (m, 2H), 7.3 (d, J=8.1 Hz, 2H), 7.2 (d, J=7.5 Hz, 1H), 6.9 (d, 1H), 3.6 (s, 2H), 3 (d, 2H), 2.9 (m, 1H), 2.5 (s, 3H), 2-2.6 (m, 6H).

Example 78

3-phenyl-2-[4-({4-[5-(pyrimidin-2-yl)-4H-1,2,4-triazol-3-yl]piperidin-1-yl}methyl)phenyl]imidazo[1,2-a]pyridine-7-carbonitrile Example 78 is prepared according to example 77
MS (M+1): 538.2
$^1$H NMR (300 MHz, CDCl$_3$):—δ 8.92 (d, J=4.5 Hz, 1H), 8.45 (s, 1H), 8.13 (d, J=7.2 Hz, 1H), 7.53-7.66 (m, 9H), 7.29

(d, J=7.8 Hz, 2H), 7.15-7.18 (dd, J=1.5 Hz, 6.9 Hz, 2H), 3.49 (s, 2H), 2.85 (bs, 2H), 1.755-2.101 (m, 5H)

Example 79

'3-phenyl-2-(4-{[4-(5-pyrimidin-2-yl-1H-1,2,4-triazol-3-yl)piperidin-1-yl]methyl}phenyl)imidazo[1,2-a]pyrimidine Example 79 is prepared according to example 77
MS (M+1): 514.13
$^1$H NMR (300 MHz, CDCl$_3$):—δ 8.88 (d, J=4.2 Hz, 2H), 8.564 (s, 1H), 8.24 (dd, J=7.5, 1.8 Hz 1H), 7.70 (d, J=8.1 Hz, 2H), 7.611-7.516 (m, 3H), 7.467-7.435 (m, 2H), 7.326 (m, 1H), 7.282-7.255 (m, 2H), 6.835-6.799 (m, 1H), 3.604 (s, 2H), 3.01 (d, J=11.1 Hz, 3H) 2.356-2.063 (m, 6H).

Example 80

'3-phenyl-2-(4-{[4-(5-pyrimidin-2-yl-4H-1,2,4-triazol-3-yl)piperidin-1-yl]methyl}phenyl)imidazo[1,2-a]pyridine Example 80 is prepared according to example 77
MS (M+1): 513.13
$^1$H NMR (300 MHz, DMSO-d$^6$) δ 9.0 (s, 2H), 8 (d, 1H), 7.4-7.7 (m, 9H), 7.1 to 7.3 (m, 3H), 6.9 (t, 1H), 3.5 (s, 2H), 2.6-3.2 (m, 3H), 1.7-2.3 (m, 6H).

Example 81

'5-phenyl-6-(4-{[4-(5-pyrimidin-2-yl-4H-1,2,4-triazol-3-yl)piperidin-1-yl]methyl}phenyl)imidazo[2,1-b][1,3]thiazole Example 81 is prepared according to example 77
MS (M+1): 519.07
$^1$H NMR (300 MHz, DMSO-d$^6$) δ 8.91 (d, J=4.2 Hz, 2H), 7.7 (d, J=4.5 Hz, 1H), 7.6-7.18 (m, 12H), 3.46 (s, 2H), 2.88-2.63 (m, 3H), 2.22-1.74 (m, 6H).

Example 82

'5-phenyl-6-(4-{[4-(5-pyrimidin-2-yl-4H-1,2,4-triazol-3-yl)piperidin-1-yl]methyl}phenyl)imidazo[2,1-b][1,3,4]thiadiazole Example 82 is prepared according to example 77
MS (M+1): 520.13
$^1$H NMR (300 MHz, CDCl$_3$):—δ 8.90 (d, J=4.8 Hz, 2H), 8.54 (s, 1H), 7.65-7.25 (m, 11H), 3.58 (s, 2H), 3.1-2.9 (m, 3H), 2.25-1.95 (m, 6H)

Example 83

'6-methyl-3-phenyl-2-(4-{[4-(5-pyrimidin-2-yl-4H-1,2,4-triazol-3-yl)piperidin-1-yl]methyl}phenyl)imidazo[1,2-b]pyridazine Example 83 is prepared according to example 77
MS (M+1): 528.2
$^1$H NMR (300 MHz, CDCl$_3$):—δ 9.0 (s, 1H), 7.9 (d, 1H), 7.7 (d, 2H), 7.3 to 7.6 (m, 8H), 6.9 (d, 1H), 4.1 (s, 2H), 3.1-3.4 (m, 3H), 2.8 (m, 3H), 2.5 (s, 1H), 2.2-2.4 (m, 3H).

Example 84

'3-phenyl-2-[4-({4-[5-(1,3-thiazol-2-yl)-1H-1,2,4-triazol-3-yl]piperidin-1-yl}methyl)phenyl]imidazo[1,2-a]pyrimidine To a solution of 0.340 g (1.137 mM) of 4-(3-phenylimidazo[1,2-a]pyrimidin-2-yl)benzaldehyde in 7 mL of THF is added triethylamine (2 eq). The reaction mixture is stirred for 5 minutes. To this solution is added 4-[5-(1,3-thiazol-2-yl)-1H-1,2,4-triazol-3-yl]piperidine dihydrochloride (Intermediate G) (1.5 eq) followed by acetic acid (2.5 eq). The reaction mixture is stirred for 10 minutes. To this mixture is added NaBH(OAc)$_3$ (6 eq) over a period of 60 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 519.07
$^1$H NMR (300 MHz, CDCl$_3$):—δ 8.567 (s, 1H), 8.26 (d, J=6 Hz 1H), 7.92 (d, J=3 Hz 1H), 7.67 (d, J=8.1 Hz, 2H), 7.549-7.364 (m, 6H), 7.227 (s, 2H), 6.852-6.816 (m, 1H), 3.585 (s, 2H), 2.99 (d, 3H) 2.211-1.971 (m, 6H).

Example 85

'3-phenyl-2-[4-({4-[5-(1,3-thiazol-2-yl)-4H-1,2,4-triazol-3-yl]piperidin-1-yl}methyl) phenyl]imidazo[1,2-a]pyridine Example 85 is prepared according to example 84
MS (M+1): 518.07
$^1$H NMR (300 MHz, CDCl$_3$):—δ 7.9-8.1 (m, 2H), 7.7 (d, 1H), 7.4-7.7 (m, 8H), 7.1-7.3 (m, 3H), 6.8 (t, 1H), 3.6 (s, 2H), 2.7-3.1 (m, 3H), 1.8-2.3 (m, 6H).

Example 86

'3-phenyl-2-[4-({4-[5-(1,3-thiazol-2-yl)-4H-1,2,4-triazol-3-yl]piperidin-1-yl}methyl)phenyl]imidazo[1,2-a]pyridine-8-carbonitrile Example 86 is prepared according to example 84
MS (M+1): 543.07
$^1$H NMR (300 MHz, CDCl$_3$):—δ 8.2 (d, 1H), 8 (s, 1H), 7.6-7.7 (m, 3H), 7.4-7.6 (m, 6H), 7.2-7.4 (m, 2H), 6.8 (t, 1H), 3.6 (s, 2H), 2.8-3.1 (m, 3H), 1.9-2.3 (m, 6H).

Example 87

'5-phenyl-6-[4-({4-[5-(1,3-thiazol-2-yl)-4H-1,2,4-triazol-3-yl]piperidin-1-yl}methyl) phenyl]imidazo[2,1-b][1,3]thiazole Example 87 is prepared according to example 84
MS (M+1): 524.07
$^1$H NMR (300 MHz, CDCl$_3$):—δ 7.95 (d, J=3.3 Hz, 1H), 7.6-7.2 (m, 12H), 6.84 (d, J=4.8 Hz, 1H), 3.59 (s, 2H), 3.05-2.85 (m, 3H), 2.3-1.9 (m, 6H).

Example 88

'5-phenyl-6-[4-({4-[5-(1,3-thiazol-2-yl)-1H-1,2,4-triazol-3-yl]piperidin-1-yl}methyl)phenyl]imidazo[2,1-b][1,3,4]thiadiazole Example 88 is prepared according to example 84
MS (M+1): 525.07
$^1$H NMR (300 MHz, CDCl$_3$):—δ 8.55 (s, 1H), 7.94 (d, J=3 Hz, 1H), 7.65-7.25 (m, 11H), 3.58 (s, 2H), 3.1-2.8 (m, 3H), 2.3-1.8 (m, 6H)

Example 89

'3-phenyl-2-[4-({4-[5-(1,3-thiazol-2-yl)-4H-1,2,4-triazol-3-yl]piperidin-1-yl}methyl)phenyl]imidazo[1,2-a]pyridine-7-carbonitrile Example 89 is prepared according to example 84
MS (M+1): 543.13
$^1$H NMR (300 MHz, CDCl$_3$):—δ 8.101 (s 1H), 8.023 (dd J=7.2 Hz, 0.9 Hz, 1H), 7.966 (d, J=3.3 Hz, 1H), 7.64 (d, J=8.1 Hz, 2H), 7.611-7.559 (m, 3H), 7.479-7.448 (m, 3H), 7.31 (d, J=8.4 Hz, 2H), 6.908 (dd, J=7.2 Hz, J=1.8 Hz, 1H) 3.615 (s, 2H), 3.053-2.915 (m, 4H), 2.24-1.993 (m, 7H)

Example 90

'2-[4-({4-[5-(2-furyl)-4H-1,2,4-triazol-3-yl]piperidin-1-yl}methyl)phenyl]-3-phenylimidazo[1,2-a]pyridine-8-carbonitrile To a solution of 0.180 g (0.557 mM) 2-(4-formylphenyl)-3-phenylimidazo[1,2-a]pyridine-8-carbonitrile in 5 mL of THF is added triethylamine (2 eq). The reaction mixture is stirred for 5 minutes. To this solution is added 4-[5-(furan-2-yl)-1H-1,2,4-triazol-3-yl]piperidine dihydrochloride (Intermediate H) (1.5 eq) followed by acetic acid (2.5 eq). The reaction mixture is stirred for 10 minutes. To this mixture is added NaBH(OAc)$_3$ (6 eq) over a period of 60 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 526.13
$^1$H NMR (300 MHz, CDCl$_3$):—δ 8.2 (d, 1H), 7.6-7.7 (m, 3H), 7.5-7.6 (m, 3H), 7.5 (m, 1H), 7.4-7.5 (m, 2H), 7.2-7.3 (m, 2H), 7 (d, 1H), 6.8 (t, 1H), 6.5 (q, 1H), 3.6 (s, 2H), 2.8-3.1 (m, 3H), 1.8-2.3 (m, 6H).

Example 91

'2-[4-({4-[5-(2-furyl)-4H-1,2,4-triazol-3-yl]piperidin-1-yl}methyl)phenyl]-3-phenylimidazo[1,2-a]pyridine Example 91 is prepared according to example 90
MS (M+1): 501.13
$^1$H NMR (300 MHz, CDCl$_3$):—δ 8 (d, 1H), 7.7 (d, 1H), 7.4-7.7 (m, 9H), 7.2-7.3 (m, 3H), 7 (d, 1H), 6.8 (t, 1H), 6.5 (q, 1H), 3.6 (s, 2H), 2.8-3 (m, 3H), 1.8-2.2 (m, 6H).

Example 92

'2-[4-({4-[5-(2-furyl)-4H-1,2,4-triazol-3-yl]piperidin-1-yl}methyl)phenyl]-6-methyl-3-phenylimidazo[1,2-b]pyridazine Example 92 is prepared according to example 90
MS (M+1): 516.13
$^1$H NMR (300 MHz, CDCl$_3$):—δ 7.9 (d, 1H), 7.6 (m, 4H), 7.4 to 7.5 (m, 4H), 7.2 to 7.3 (m, 2H), 6.9 to 7 (m, 2H), 6.5 (q, 1H), 3.6 (s, 2H), 2.8 to 3.1 (m, 3H), 2.5 (s, 3H), 1.9 to 2.2 (m, 6H).

Example 93

'6-[4-({4-[5-(2-furyl)-4H-1,2,4-triazol-3-yl]piperidin-1-yl}methyl)phenyl]-5-phenylimidazo[2,1-b][1,3]thiazole Example 93 is prepared according to example 90
MS (M+1): 507.07
$^1$H NMR (300 MHz, CDCl$_3$):—δ 8.55 (s, 1H), 7.65-7.2 (m, 12H), 6.98 (d, J=3.3 Hz, 1H), 6.55-6.45 (m, 1H), 3.56 (s, 2H), 3.1-2.8 (m, 3H), 2.3-1.8 (m, 6H)

Example 94

'6-[4-({4-[5-(2-furyl)-4H-1,2,4-triazol-3-yl]piperidin-1-yl}methyl)phenyl]-5-phenylimidazo[2,1-b][1,3,4]thiadiazole Example 94 is prepared according to example 90
MS (M+1): 508.07
$^1$H NMR (300 MHz, CDCl$_3$):—δ 7.6-7.15 (m, 11H), 6.97 (d, J=3 Hz, 1H), 6.82 (d, J=4.5 Hz, 1H), 6.55-6.45 (m, 1H), 3.51 (s, 2H), 3.0-2.8 (m, 3H), 2.2-1.8 (m, 6H).

Example 95

'2-[4-({4-[5-(2-furyl)-4H-1,2,4-triazol-3-yl]piperidin-1-yl}methyl)phenyl]-3-phenylimidazo[1,2-a]pyrimidine Example 95 is prepared according to example 90
MS (M+1): 502.2
$^1$H NMR (300 MHz, CDCl$_3$):—δ 8.57-8.55 (m, 1H), 8.25 (dd, J=6.6, 1.8 Hz, 1H), 7.69 (d, J=8.4 Hz 2H), 7.56-7.43 (m, 6H), 7.24 (s, 2H), 6.98 (d, J=3.3 Hz, 1H), 6.84-6.81 (m, 1H), 6.50-6.48 (m, 1H), 3.581 (s, 2H), 3.02-2.91 (m, 3H) 2.18 (t, 2H), 2.085-1.93 (m, 4H).

Example 96

'2-[4-({4-[5-(2-furyl)-4H-1,2,4-triazol-3-yl]piperidin-1-yl}methyl)phenyl]-3-phenylimidazo[1,2-a]pyridine-7-carbonitrile Example 96 is prepared according to example 90
MS (M+1): 526.13
$^1$H NMR (300 MHz, CDCl$_3$):—δ 8.07 (s, 1H), 7.51 (d, J=5.4 Hz, 1H), 7.64 (d, J=8.4 Hz, 2H), 7.58-7.43 (m 6H), 7.29 (d, J=8.1 Hz, 2H), 7.98 (d, J=3.3 Hz, 1H), 6.89 (dd, J=6.9 Hz, 4.5 Hz, 1H), 6.51 (dd, J=3.3 Hz, 1.8 Hz, 1H) 3.6 (s, 2H), 3.04-2.91 (m, 3H), 2.4-1.94 (m, 8H)

Example 97

'3-phenyl-2-[4-({4-[5-(2-thienyl)-4H-1,2,4-triazol-3-yl]piperidin-1-yl}methyl)phenyl]imidazo[1,2-a]pyridine To a solution of 0.120 g (0.402 mM) of 4-(3-phenylimidazo[1,2-a]pyridin-2-yl)benzaldehyde in 5 mL of THF is added triethylamine (2 eq). The reaction mixture is stirred for 5 minutes. To this solution is added 4-[5-(thiophen-2-yl)-1H-1,2,4-triazol-3-yl]piperidine dihydrochloride (Intermediate I) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 517.13

$^1$H NMR (300 MHz, CDCl$_3$):—δ 8 (d, 1H), 7.4-7.7 (m, 9H), 7.2-7.4 (m, 4H), 7.1 (m, 1H), 6.8 (t, 1H), 3.6 (s, 2H), 2.8-3.1 (m, 3H), 1.8-2.2 (m, 6H).

Example 98

'3-phenyl-2-[4-({4-[5-(2-thienyl)-4H-1,2,4-triazol-3-yl]piperidin-1-yl}methyl)phenyl]imidazo[1,2-a]pyridine-8-carbonitrile Example 98 is prepared according to example 97
MS (M+1): 542.13
$^1$H NMR (300 MHz, CDCl$_3$):—δ 8.1 (d, 1H), 7.6-7.7 (m, 4H), 7.5-7.6 (m, 3H), 7.4-7.5 (m, 2H), 7.2-7.4 (m, 3H), 7.1 (m, 1H), 6.8 (t, 1H), 3.6 (s, 2H), 2.8-3.1 (m, 3H), 1.8-2.3 (m, 6H).

Example 99

'6-methyl-3-phenyl-2-[4-({4-[5-(2-thienyl)-4H-1,2,4-triazol-3-yl]piperidin-1-yl}methyl)phenyl]imidazo[1,2-b]pyridazine Example 99 is prepared according to example 97
MS (M+1): 532.13
$^1$H NMR (300 MHz, CDCl$_3$):—δ 7.9 (d, J=9.3 Hz, 1H), 7.5-7.7 (m, 5H), 7.4-7.5 (m, 3H), 7.3-7.35 (d, J=5.1 Hz, 1H), 7.2-7.3 (m, 2H), 3.6 (s, 2H), 2.8-3 (m, 3H), 2.5 (s, 3H), 1.8-2.2 (m, 6H).

Example 100

'5-phenyl-6-[4-({4-[5-(2-thienyl)-4H-1,2,4-triazol-3-yl]piperidin-1-yl}methyl)phenyl]imidazo[2,1-b][1,3]thiazole Example 100 is prepared according to example 97
MS (M+1): 523.07
$^1$H NMR (300 MHz, CDCl$_3$):—δ 7.66-7.0 (m, 14H), 6.825 (d, J=4.5 Hz, 1H), 3.61 (s, 2H), 3.15-2.85 (m, 3H), 2.3-1.9 (m, 6H).

Example 101

'5-phenyl-6-[4-({4-[5-(2-thienyl)-4H-1,2,4-triazol-3-yl]piperidin-1-yl}methyl)phenyl]imidazo[2,1-b][1,3,4]thiadiazole Example 101 is prepared according to example 97
MS (M+1): 524.07
$^1$H NMR (300 MHz, CDCl$_3$):—δ 8.57 (s, 1H), 7.7-7.05 (m, 13H), 3.61 (s, 2H), 3.14-2.85 (m, 3H), 2.3-1.9 (m, 6H).

Example 102

'3-phenyl-2-[4-({4-[5-(2-thienyl)-4H-1,2,4-triazol-3-yl]piperidin-1-yl}methyl)phenyl]imidazo[1,2-a]pyridine-7-carbonitrile Example 102 is prepared according to example 97
MS (M+1): 542.13
$^1$H NMR (300 MHz, DMSO-d$^6$) δ 8.44 (s, 1H), 8.13 (d, J=7.2 Hz, 1H), 7.64=7.5 (m, 10H), 7.28 (d, J=5.4 Hz, 2H), 7.72-7.12 (m, 2H), 3.51 (bs, 3H), 2.89-2.78 (m 3H), 2.1-1.74 (m, 6H)

Example 103

7-chloro-3-phenyl-2-[4-({4-[5-(2-thienyl)-4H-1,2,4-triazol-3-yl]piperidin-1-yl}methyl)phenyl]imidazo[1,2-a]pyridine Example 103 is prepared according to example 97
MS (M+1): 551.07
$^1$H NMR (300 MHz, CDCl$_3$):—δ 7.9 (d, J=7.5 Hz, 1H), 7.7 (d, J=2.1 Hz, 1H), 7.5-7.67 (m, 5H), 7.4-7.5 (m, 2H), 7.18-7.35 (m, 3H), 7.09 (q, 1H), 6.7 (q, 1H), 3.5 (s, 2H), 2.8-3 (m, 3H), 1.7-2.2 (m, 6H)

Example 104

'6-methyl-3-phenyl-2-[4-({4-[5-(1H-pyrrol-2-yl)-4H-1,2,4-triazol-3-yl]piperidin-1-yl}methyl)phenyl]imidazo[1,2-b]pyridazine To a solution of 0.150 g (0.479 mM) of 4-(6-methyl-3-phenylimidazo[1,2-b]pyridazin-2-yl)benzaldehyde in 6 mL of THF is added triethylamine (2 eq). The reaction mixture is stirred for 5 minutes. To this solution is added 4-[5-(1H-pyrrol-2-yl)-1H-1,2,4-triazol-3-yl]piperidine dihydrochloride (Intermediate J) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.

MS (M+1): 515.13
$^1$H NMR (300 MHz, CDCl$_3$):—δ 9.5 (s, 1H), 7.9 (d, J=9 Hz, 1H), 7.55-7.65 (m, 4H), 7.4-7.5 (m, 3H), 7.2-7.3 (m, 2H), 6.8-7 (m, 2H), 6.7 (s, 1H), 6.2-6.3 (m, 1H), 3.5 (s, 2H), 2.8-3 (m, 3H), 2.5 (s, 3H) 1.7-2.2 (m, 6H)

Example 105

'3-phenyl-2-[4-({4-[5-(1H-pyrrol-2-yl)-4H-1,2,4-triazol-3-yl]piperidin-1-yl}methyl)phenyl]imidazo[1,2-a]pyridine-8-carbonitrile Example 105 is prepared according to example 104
MS (M+1): 525.13
$^1$H NMR (300 MHz, CDCl$_3$):—δ 9.5 (s, 1H), 8.1 (d, J=6.9 Hz, 1H), 7.6-7.7 (m, 3H), 7.5-7.6 (m, 3H), 7.4-7.5 (m, 2H), 7.2-7.3 (m, 2H), 6.5-7 (m, 3H), 6.3 (m, 1H), 3.5 (s, 2H), 2.8-3 (m, 3H), 1.7-2.2 (m, 6H).

Example 106

'3-phenyl-2-[4-({4-[5-(1H-pyrrol-2-yl)-4H-1,2,4-triazol-3-yl]piperidin-1-yl}methyl)phenyl]imidazo[1,2-a]pyrimidine Example 106 is prepared according to example 104
MS (M+1): 501.13
$^1$H NMR (300 MHz, CDCl$_3$):—δ 8.56 (q, J=2.1 Hz, 1H), 8.25 (dd, J=6.9, 2.1 Hz, 1H), 7.68 (d, J=8.1 Hz, 2H), 7.60-7.51 (m, 3H), 7.45-7.428 (m, 2H), 7.24 (s, 2H), 6.91-6.76 (m, 3H), 6.24 (q, J=3.3 Hz, 1H), 3.56 (s, 2H), 2.98 (d, J=11.1 Hz, 2H), 2.88-2.81 (m, 1H), 2.18-1.93 (m, 6H), Example 107

'7-chloro-3-phenyl-2-[4-({4-[5-(1H-pyrrol-2-yl)-4H-1,2,4-triazol-3-yl]piperidin-1-yl}methyl)phenyl]imidazo[1,2-a]pyridine Example 107 is prepared according to example 104
MS (M+1): 534.13
$^1$H NMR (300 MHz, CDCl$_3$):—δ 8.56 (q, J=2.1 Hz, 1H), 8.25 (dd, J=6.9, 2.1 Hz, 1H), 7.68 (d, J 9.5 (s, 1H), 7.9 (d, J=7.5 Hz, 1H), 7.4-7.7 (m, 8H), 7.2-7.3 (m, 2H), 6.9 (m, 1H), 6.7-6.8 (m, 2H), 6.3 (q, 1H), 3.5 (s, 2H), 2.8-3 (m, 3H), 1.8-2.2 (m, 6H).

Example 108

'5-phenyl-6-[4-({4-[5-(1H-pyrrol-2-yl)-4H-1,2,4-triazol-3-yl]piperidin-1-yl}methyl)phenyl]imidazo[2,1-b][1,3,4]thiadiazole Example 108 is prepared according to example 104
MS (M+1): 507.13
$^1$H NMR (300 MHz, CDCl$_3$):—δ 9.7 (s, 1H), 8.54 (s, 1H), 7.66-7.24 (m, 10H), 6.87 (br s, 1H), 6.73 (br s, 1H), 6.26 (m, 1H), 3.57 (s, 2H), 3.1-2.6 (m, 3H), 2.25-1.85 (m, 6H).

Example 109

'5-phenyl-6-[4-({4-[5-(1H-pyrrol-2-yl)-4H-1,2,4-triazol-3-yl]piperidin-1-yl}methyl)phenyl]imidazo[2,1-b][1,3]thiazole Example 109 is prepared according to example 104
MS (M+1): 506.13
$^1$H NMR (300 MHz, CDCl$_3$):—δ 9.93 (s, 1H), 7.6-7.2 (m, 10H), 6.9-6.7 (m, 3H), 6.3-6.2 (m, 1H), 3.59 (s, 2H), 3.0-2.8 (m, 3H), 2.3-1.8 (m, 7H)

Example 110

'3-phenyl-2-[4-({4-[5-(1H-pyrrol-2-yl)-4H-1,2,4-triazol-3-yl]piperidin-1-yl}methyl)phenyl]imidazo[1,2-a]pyridine-7-carbonitrile Example 110 is prepared according to example 104
MS (M+1): 525.2
$^1$H NMR (300 MHz, CDCl$_3$):—δ 8.06 (s, 1H), 8.8 (d, J=7.2 Hz, 1H), 7.614 (d, J=4.2 Hz, 2H), 7.59-7.57 (m 3H), 7.46-7.43 (m, 2H), 7.26 (s, 2H), 6.91-6.87 (m, 2H), 6.725 (s, 1H) 6.28 (dd, J=6 Hz, 2.7 Hz, 1H), 3.515 (s, 1H), 2.96 (d, 2H), 2.82 (m, 1H), 2.15-1.71 (m, 7H)

Example 111

'3-phenyl-2-(4-{[4-(3-pyridin-2-yl-1H-pyrazol-5-yl)piperidin-1-yl]methyl}phenyl)imidazo[1,2-a]pyridine To a solution of 0.250 g (0.838 mM) of 4-(3-phenylimidazo[1,2-a]pyridin-2-yl)benzaldehyde in 6 mL of THF is added triethylamine (2 eq). The reaction mixture is stirred for 5 minutes. To this solution is added 2-[3-(piperidin-4-yl)-1H-pyrazol-5-yl]pyridine dihydrochloride (Intermediate K) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 511.13
$^1$H NMR (300 MHz, CDCl$_3$):—δ 8.6 (d, 1H), 7.9 (d, 1H), 7.6-7.8 (m, 5H), 7.4-7.6 (m, 5H), 7.15-7.4 (m, 4H), 6.8 (t, 1H), 6.6 (s, 1H), 3.7 (s, 2H), 3.1 (m, 2H), 2.8 (m, 1H), 1.8-2.4 (m, 6H).

Example 112

'5-phenyl-6-(4-{[4-(5-pyridin-2-yl-1H-pyrazol-3-yl)piperidin-1-yl]methyl}phenyl)imidazo[2,1-b][1,3,4]thiadiazole Example 112 is prepared according to example 111
MS (M+1): 518.07
$^1$H NMR (300 MHz, CDCl$_3$):—δ 9.22 (s, 1H), 8.53 (s, 1H), 7.9-7.75 (m, 2H), 7.6-7.2 (m, 10H), 6.61 (s, 1H), 3.49 (s, 2H), 3.0-2.5 (m, 3H), 2.2-1.6 (m, 6H)

Example 113

'5-phenyl-6-(4-{[4-(5-pyridin-2-yl-1H-pyrazol-3-yl)piperidin-1-yl]methyl}phenyl)imidazo[2,1-b][1,3]thiazole Example 113 is prepared according to example 111
MS (M+1): 517.07
$^1$H NMR (300 MHz, CDCl$_3$):—δ 12.75 (s, 1H), 8.53 (d, J=4.8 Hz, 1H), 7.92-7.18 (m, 14H), 6.6 (s, 1H), 3.45 (s, 2H), 2.95-2.55 (m, 3H), 2.2-1.55 (m, 5H).

Example 114

'3-phenyl-2-(4-{[4-(5-pyridin-2-yl-4H-1,2,4-triazol-3-yl) piperidin-1-yl]methyl}phenyl)imidazo[1,2-a]pyridine-7-carbonitrile Example 114 is prepared according to example 111
MS (M+1): 536.2
$^1$H NMR (300 MHz, CDCl$_3$):—δ 8.57 (d, J=4.8 Hz, 1H), 8.06 (s, 1H), 8.02 (d, J=7.2 Hz, 1H), 7.73-7.44 (m, 9H), 7.30 (d, J=8.1 Hz, 2H), 7.23-7.19 (m, 1H), 6.89 (dd, J=7.2 Hz, 1.8 Hz, 1H), 6.59 (s, 1H), 3.56 (s, 2H), 2.50 (d, 2H), 2.74 (m, 1H), 2.15-1.82 (m, 14H)

Example 115

'3-phenyl-2-(4-{[4-(5-pyridin-2-yl-1,2,4-oxadiazol-3-yl)piperidin-1-yl]methyl}phenyl)imidazo[1,2-a]pyridine-7-carbonitrile To a solution of 0.250 g (0.838 mM) of 2-(4-formylphenyl)-3-phenylimidazo[1,2-a]pyridine-7-carbonitrile in 6 mL of THF is added triethylamine (2 eq). The reaction mixture is stirred for 5 minutes. To this solution is added 2-[3-(piperidin-4-yl)1,2,4-oxadiazol-5-yl]pyridine dihydrochloride (Intermediate L) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 537.6
$^1$H NMR (300 MHz, DMSO-d$^6$) δ 8.74 (d, J=4.8 Hz, 1H), 8.43 (s, 1H), 8.113 (d, J=7.2 Hz, 1H), 8.061-7.99 (m, 2H), 7.64-7.51 (m, 8H), 7.3 (d, J=8.1 Hz, 2H), 7.15 (dd, J=6.9 Hz 1.5 Hz, 1H), 3.47- (s, 2H), 2.84-2.80 (m, 2H), 2.17-2.05 (m, 4H), 1.83-1.79 (m, 2H)

Example 116

'3-phenyl-2-(4-{[4-(5-pyridin-2-yl-1,2,4-oxadiazol-3-yl)piperidin-1-yl]methyl}phenyl)imidazo[1,2-a]pyrimidine Example 116 is prepared according to example 115
MS (M+1): 514.13
$^1$H NMR (300 MHz, DMSO-d$^6$) 68.75 (d, J=4.8 Hz, 1H), 8.59 (q, 1H), 8.55-8.44 (m, 1H), 8.07-7.98 (m, 2H), 7.64-7.47 (m, 8H), 7.03 (q, 1H), 7.31 (m, 2H), 3.49 (s, 2H), 3.19-3.14 (m, 1H), 2.91-2.82 (m, 2H), 2.24-2.06 (m, 4H), 1.89-1.81 (m, 2H).

Example 117

3-phenyl-2-(4-{[4-(5-phenyl-4H-1,2,4-triazol-3-yl)piperidin-1-yl]methyl}phenyl)imidazo[1,2-a]pyridine-8-carbonitrile To a solution of 0.250 g (0.838 mM) of 2-(4-formylphenyl)-3-phenylimidazo[1,2-a]pyridine-8-carbonitrile in 6 mL of THF is added triethylamine (2 eq). The reaction mixture is stirred for 5 minutes. To this solution is added 4-(5-phenyl-1H-1,2,4-triazol-3-yl) piperidine (Intermediate M) (1.5 eq) followed by acetic acid (2.5 eq). The reaction mixture is stirred for 10 minutes. To this mixture is added NaBH(OAc)$_3$ (6 eq) over a period of 40 minutes. The reaction mixture is stirred overnight. The reaction mixture is quenched with methanol and concentrated. The residue obtained is taken up in chloroform and washed with water, dried and concentrated. The crude is purified on a flash column chromatography to obtain the desired compound.
MS (M+1): 536.2
$^1$H NMR (300 MHz, CDCl$_3$):—δ 8.1 (d, 1H), 8.0 (m, 2H), 7.6-7.7 (m, 3H), 7.5-7.6 (m, 3H), 7.4-7.5 (m, 5H), 7.2-7.3 (m, 2H), 6.8 (t, 1H), 3.6 (s, 2H), 2.8-3.1 (m, 3H), 1.9-2.3 (m, 6H).

Example 118

3-phenyl-2-(4-{[4-(5-phenyl-4H-1,2,4-triazol-3-yl)piperidin-1-yl]methyl}phenyl)imidazo[1,2-a]pyridine-7-carbonitrile Example 118 is prepared according to example 117
MS (M+1): 536.2
$^1$H NMR (300 MHz, CDCl$_3$):—δ 8.1 (s, 1H), 8.03-7.9 (m, 3H), 7.62 (d, J=8.4 Hz, 2H), 7.57-7.54 (m, 3H), 7.46-7.39 (m, 5H), 7.3 (d, J=9.6 Hz, 2H), 6.9 (dd, J=4.2 Hz, 0.6 Hz, 1H), 3.54 (s, 2H), 3.02-2.91 (m, 3H), 2.185-1.87 (m, 6H)

Example 119

6-methyl-3-phenyl-2-(4-{[4-(5-phenyl-4H-1,2,4-triazol-3-yl) piperidin-1-yl]methyl}phenyl)imidazo[1,2-b]pyridazine Example 119 is prepared according to example 117
MS (M+1): 526.13
$^1$H NMR (300 MHz, CDCl$_3$):—δ 8.1 (d, J=8.1 Hz, 2H), 7.9 (d, J=9.3 Hz, 1H), 7.6 (m, 4H), 7.4 to 7.5 (m, 6H), 7.2 to 7.3 (m, 2H), 6.9 (d, J=9 Hz, 1H), 3.6 (s, 2H), 2.8 to 3.1 (m, 3H), 2.5 (s, 3H), 1.8 to 2.2 (m, 6H).

Example 120

7-chloro-3-phenyl-2-(4-{[4-(5-phenyl-4H-1,2,4-triazol-3-yl)piperidin-1-yl]methyl}phenyl)imidazo[1,2-a]pyridine Example 120 is prepared according to example 117
MS (M+1): 445.2
$^1$H NMR (300 MHz, CDCl$_3$):—δ 8.1 (d, 2H), 7.9 (d, J=7.5 Hz, 1H), 7.7 (d, 1H), 7.6 to 7.65 (m, 2H), 7.4 to 7.6 (m, 7H), 7.2 to 7.3 (m, 2H), 6.8 (dd, J=7.2 Hz, 1H), 3.6 (s, 2H), 2.8 to 3.1 (m, 3H), 1.6 to 2.2 (m, 6H).

Example 121

3-phenyl-2-(4-{[4-(5-phenyl-4H-1,2,4-triazol-3-yl)piperidin-1-yl]methyl}phenyl)imidazo[1,2-a]pyrimidine Example 121 is prepared according to example 117
MS (M+1): 512.27
1H NMR (DMSO d6):—δ 8.59 (q, J=2.4 Hz, 1H), 8.476 (dd, J=6.9, 1.8 Hz, 1H), 7.975 (d, J=7.2 Hz 2H), 7.646-7.529 (m, 7H), 7.437-7.411 (m, 3H), 7.281 (d, J=7.8 Hz, 2H), 7.034 (q, 1H), 3.485 (s, 2H), 2.873 (d J=9.9 Hz, 2H), 2.729 (t, 1H) 2.087 (t, 2H), 1.925 (t, 2H), 1.799 (t, 2H).

Example 122

5-phenyl-6-(4-{[4-(5-phenyl-4H-1,2,4-triazol-3-yl)piperidin-1-yl]methyl}phenyl)imidazo[2,1-b][1,3]thiazole Example 122 is prepared according to example 117
MS (M+1): 517.07
$^1$H NMR (300 MHz, CDCl$_3$):—δ 8.05-8.00 (m, 2H), 7.6-7.21 (m, 13H), 6.82 (d, J=4.5 Hz, 1H), 3.58 (s, 2H), 3.1-2.85 (m, 3H), 2.3-1.9 (m, 6H).

Example 123

5-phenyl-6-(4-{[4-(5-phenyl-4H-1,2,4-triazol-3-yl)piperidin-1-yl]methyl}phenyl)imidazo[2,1-b][1,3,4]thiadiazole Example 123 is prepared according to example 117
MS (M+1): 518.13
$^1$H NMR (300 MHz, CDCl$_3$):—δ 8.54 (s, 1H), 8.07-7.98 (m, 2H), 7.68-7.22 (m, 12H), 3.56 (s, 2H), 3.1-2.8 (m, 3H), 2.25-1.8 (m, 6H).

Example 124 methyl 3-phenyl-2-[4-({4-[5-(pyridin-2-yl)-4H-1,2,4-triazol-3-yl]piperidin-1-yl}methyl)phenyl]imidazo[1,2-a]pyridine-7-carboxylate Example 124 is prepared according to example 12
MS (M+1); 570.1
$^1$H NMR (300 MHz, CDCl$_3$):—δ 8.67 (d, J=4.2 Hz, 1H), 8.414 (s, 1H), 8.161 (d, J=7.8 Hz 1H), 7.967 (d, J=6.6 Hz, 1H), 7.825 (t, J=1.5 Hz 1H), 7.621 (d, J=8.1 Hz, 2H), 7.564-

7.517 (m, 3H), 7.373-7.319 (m, 2H), 7.295 (s, 2H) 3.97 (s, 3H), 3.535 (s, 2H), 2.98 (d, J=11.4 Hz, 2H), 2.175-1.948 (m, 6H).

Example 125

3-phenyl-2-[4-({4-[5-(pyridin-2-yl)-4H-1,2,4-triazol-3-yl]piperidin-1-yl}methyl)phenyl]imidazo[1,2-a]pyridine-7-carboxylic acid To as solution of example 124 (0.100 gm 0.175 mM) in methanol (3 ml) is added 1N NaOH solution (1 ml). The resulting reaction mixture is stirred at room temperature for overnight. Reaction mass is then concentrated to remove methanol, diluted with 4 ml of water and neutralized (pH ~7). Solid precipitated is filtered and dried to afford the desired compound.

MS (M+1): 556.13
$^1$H NMR (DMSO-$d_6$):—δ 8.653 (bs, 1H), 8.32 (s, 1H), 8.174 (s, 1H), 8.079-8.015 (m, 2H), 7.93 (bs, 1H), 7.65-7.532 (m, 7H), 7.462 (bs, 1H), 7.337-7.263 (m, 3H), 3.5 (s, 3H), 2.877 (d, J=10.8 Hz, 2H) 2.729 (m, 21H), 2.118 (t, J=11.1 Hz, 2H), 1.953 (d, 2H), 1.80 (t, J=10.5 Hz, 2H).

Example 126 methoxy[5-phenyl-6-(4-{[4-(5-pyridin-2-yl-1H-1,2,4-triazol-3-yl)piperidin-1-yl]methyl}phenyl)imidazo[2,1-b][1,3]thiazol-2-yl]methanol Example 126 is prepared according to example 12
MS (M+1): 573.13
$^1$H NMR (300 MHz, CDCl$_3$):—δ 8.675 (d, J=4.5 Hz, 1H), 8.175 (d, J=7.8 Hz, 1H), 8.09 (s, 1H), 7.844 (td, J=7.8 Hz, 1.8 Hz, 1H), 7.60 (d, J=8.1 Hz, 2H), 7.511-7.46 (m, 5H), 7.395-7.349 (m, 1H), 7.292 (d, J=6.3 Hz, 1H) 3.934 (s, 3H), 3.55 (s, 2H), 3.011 (d, J=11.4 Hz, 2H), 2.88 (m, 2H), 2.257-1.975 (m, 8H)

Example 127

'5-phenyl-6-(4-{[4-(5-pyridin-2-yl-4H-1,2,4-triazol-3-yl)piperidin-1-yl]methyl}phenyl)imidazo[2,1-b][1,3]thiazole-2-carboxylic acid To as solution of example 126 (0.125 gm 0.219 mM) in methanol 3 ml and water 2 ml is added potassium carbonate (3 eq.). The resulting reaction mixture is stirred at room temperature for overnight. Reaction mass is then concentrated to remove methanol, diluted with 4 ml of water and neutralized (pH ~7). Solid precipitated is filtered and dried to afford the desired compound.

MS (M+1): 562.07
$^1$H NMR (300 MHz, DMSO-$d_6$) δ 14.44 (bs, 1H), 8.67 (d, J=3 Hz, 1H), 8.02 (d, J=7.5 Hz, 1H), 7.95 (s, 1H), 7.68 (s, 1H), 7.57-7.44 (m, 8H), 7.34 (d, J=7.5 Hz, 2H), 3.83-3.75 (bs, 2H) 3.17-2.89 (m, 4H), 2.18-1.69 (m, 4H)

Commercial Utility

The compounds of formula (I) and the stereoisomers of the compounds of formula (I) according to the invention are hereinafter referred to as the compounds of the invention. In particular, the compounds of the invention are pharmaceutically acceptable. The compounds according to the invention have valuable pharmaceutical properties, which make them commercially utilizable. In particular, they inhibit the Pi3K/Akt pathway and exhibit cellular activity. They are expected to be commercially applicable in the therapy of diseases (e.g. diseases dependent on overactivated Pi3K/Akt.

Cellular activity and analogous terms in the present invention is used as known to persons skilled in the art, as an example, induction of apoptosis or chemosensitization.

Chemosensitization and analogous terms in the present invention is used as known to persons skilled in the art. These stimuli include, for example, effectors of death receptor and survival pathways as well as cytotoxic/chemotherapeutic and targeted agents and finally radiation therapy. Induction of apoptosis and analogous terms according to the present invention are used to identify a compound which executes programmed cell death in cells contacted with that compound or in combination with other compounds routinely used for therapy. Apoptosis in the present invention is used as known to persons skilled in the art. Induction of apoptosis in cells contacted with the compound of this invention might not necessarily be coupled with inhibition of cell proliferation. Preferably, the inhibition of proliferation and/or induction of apoptosis are specific to cells with aberrant cell growth.

Further on, the compounds according to the present invention inhibit protein kinase activity in cells and tissues, causing a shift towards dephosphorylated substrate proteins and as functional consequence, for example the induction of apoptosis, cell cycle arrest and/or sensitization towards chemotherapeutic and target-specific cancer drugs. In a preferred embodiment, inhibition of Pi3K/Akt pathway induces cellular effects as mentioned herein alone or in combination with standard cytotoxic or targeted cancer drugs.

Compounds according to the present invention exhibit anti-proliferative and/or pro-apoptotic and/or chemosensitizing properties. Accordingly, the compounds of the present invention are useful for treatment of hyperproliferative disorders, in particular cancer. Therefore the compounds of the present invention are used in the production of an anti-proliferative and/or pro-apoptotic and/or chemosensitizing effect in mammals such as human being suffering from a hyperproliferative disorders, like cancer.

Compounds according to the present invention exhibit anti-proliferative and/or pro-apoptotic properties in mammals such as humans due to inhibition of metabolic activity of cancer cells which are able to survive despite of unfavourable growth conditions such as glucose depletion, hypoxia or other chemo stress.

Thus, the compounds according to the present invention are for treating, ameliorating or preventing diseases of benign or malignant behaviour as described herein, such as e.g. for inhibiting cellular neoplasia.

Neoplasia in the present invention is used as known to persons skilled in the art. A benign neoplasia is described by hyperproliferation of cells, incapable of forming an aggressive, metastasizing tumor in-vivo. In contrast, a malignant neoplasia is described by cells with multiple cellular and biochemical abnormalities, capable of forming a systemic disease, for example forming tumor metastasis in distant organs.

The compounds according to the present invention can be preferably used for the treatment of malignant neoplasia. Examples of malignant neoplasia treatable with the compounds according to the present invention include solid and hematological tumors. Solid tumors can be exemplified by tumors of the breast, bladder, bone, brain, central and peripheral nervous system, colon, endocrine glands (e.g. thyroid and adrenal cortex), esophagus, endometrium, germ cells, head and neck, kidney, liver, lung, larynx and hypopharynx, mesothelioma, ovary, pancreas, prostate, rectum, renal, small intestine, soft tissue, testis, stomach, skin, ureter, vagina and vulva. Malignant neoplasias include inherited cancers exemplified by Retinoblastoma and Wilms tumor. In addition, malignant neoplasias include primary tumors in said organs and corresponding secondary tumors in distant organs ("tumor metastases"). Hematological tumors can be exemplified by aggressive and indolent forms of leukemia and lymphoma, namely non-Hodgkins disease, chronic and acute myeloid leukemia (CML/AML), acute lymphoblastic leukemia (ALL), Hodgkins disease, multiple myeloma and T-cell lymphoma. Also included are myelodysplastic syndrome, plasma cell neoplasia, paraneoplastic syndromes, and cancers of unknown primary site as well as AIDS related malignancies.

It is noted that a malignant neoplasia does not necessarily require the formation of metastases in distant organs. Certain tumors exert devastating effects on the primary organ itself through their aggressive growth properties. These can lead to the destruction of the tissue and organ structure finally resulting in failure of the assigned organ function and death.

Drug resistance is of particular importance for the frequent failure of standard cancer therapeutics. This drug resistance is caused by various cellular and molecular mechanisms. One aspect of drug resistance is caused by constitutive activation of anti-apoptotic survival signals with PKB/Akt as a key signalling kinase. Inhibition of the Pi3K/Akt pathway leads to a resensitization towards standard chemotherapeutic or target specific cancer therapeutics. As a consequence, the commercial applicability of the compounds according to the present invention is not limited to $1^{st}$ line treatment of cancer patients. In a preferred embodiment, cancer patients with resistance to cancer chemotherapeutics or target specific anti-cancer drugs are also amenable for treatment with these compounds for e.g. $2^{nd}$ or $3^{rd}$ line treatment cycles. In particular, the compounds according to the present invention might be used in combination with standard chemotherapeutic or targeted drugs to resensitize tumors towards these agents.

In the context of their properties, functions and utilities mentioned herein, the compounds according to the present invention are distinguished by unexpected valuable and desirable effects related therewith, such as e.g. superior therapeutic window, superior bioavailability (such as e.g. good oral absorption), low toxicity and/or further beneficial effects related with their therapeutic and pharmaceutical qualities.

Compounds according to the present invention are for treatment, prevention or amelioration of the diseases of benign and malignant behavior as described before, such as e.g. benign or malignant neoplasia, particularly cancer, especially a cancer that is sensitive to Pi3K/Akt pathway inhibition.

The present invention further includes a method for treating, prevention or amelioration mammals, including humans, which are suffering from one of the abovementioned conditions, illnesses, disorders or diseases. The method is characterized in that a pharmacologically active and therapeutically effective and tolerable amount of one or more of compounds according to the present invention is administered to the subject in need of such treatment.

The present invention further includes a method for treating, preventing or ameliorating diseases responsive to inhibition of the Pi3K/Akt pathway, in a mammal, including human, comprising administering a pharmacologically active and therapeutically effective and tolerable amount of one or more of the compounds according to the present invention to said mammal.

The present invention further includes a method for treating hyperproliferative diseases of benign or malignant behaviour and/or disorders responsive to induction of apoptosis, such as e.g. cancer, particularly any of those cancer diseases described above, in a mammal, comprising administering a pharmacologically active and therapeutically effective and tolerable amount of one or more of the compounds according to the present invention to said mammal.

The present invention further includes a method for inhibiting cellular hyperproliferation or arresting aberrant cell growth in a mammal, comprising administering a pharmacologically active and therapeutically effective and tolerable amount of one or more of the compounds according to the present invention to said mammal.

The present invention further includes a method for inducing apoptosis in the therapy of benign or malignant neoplasia, particularly cancer, comprising administering a pharmacologically active and therapeutically effective and tolerable amount of one or more of the compounds according to the present invention to a subject in need of such therapy.

The present invention further includes a method for inhibiting protein kinase activity in cells comprising administering a pharmacologically active and therapeutically effective and tolerable amount of one or more of the compounds according to the present invention to a patient in need of such therapy.

The present invention further includes a method for sensitizing towards chemotherapeutic or target-specific anti-cancer agents in a mammal, comprising administering a pharmacologically active and therapeutically effective and tolerable amount of one or more of the compounds according to the present invention to said mammal.

The present invention further includes a method for treating benign and/or malignant neoplasia, particularly cancer, in a mammal, including human, comprising administering a pharmacologically active and therapeutically effective and tolerable amount of one or more of the compounds according to the present invention to said mammal.

The present invention further relates to the use of the compounds for the production of pharmaceutical compositions, which are employed for the treatment, prophylaxis, and/or amelioration of one or more of the illnesses mentioned.

The present invention further relates to the use of the compounds for the manufacture of pharmaceutical compositions for treating, preventing or ameliorating hyperproliferative diseases and/or disorders responsive to the induction of apoptosis, such as e.g. benign or malignant neoplasia, in particular cancer.

The present invention further relates to the use of the compounds according to this invention for the production of pharmaceutical compositions for treating, preventing or ameliorating benign or malignant neoplasia, particularly cancer, such as e.g. any of those cancer diseases described above.

The invention further relates to a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The invention further relates to a pharmaceutical composition, comprising a compound according to the invention or a pharmaceutically acceptable salt thereof, for the treatment and/or prophylaxis of (hyper)proliferative diseases and/or disorders responsive to induction of apoptosis, which include benign neoplasia and malignant neoplasia, including cancer.

The present invention further relates to the use of compounds and pharmaceutically acceptable salts according to the present invention for the manufacture of pharmaceutical compositions, which can be used for sensitizing towards chemotherapeutic and/or target specific anti-cancer agents.

The present invention further relates to the use of compounds according to the present invention for the manufacture of pharmaceutical compositions, which can be used for sensitizing towards radiation therapy of those diseases mentioned herein, particularly cancer.

The present invention further relates to the use of the compounds according to the present invention for the manufacture of pharmaceutical compositions, which can be used in the treatment of diseases sensitive to protein kinase inhibitor therapy and different to cellular neoplasia. These non-malignant diseases include, but are not limited to benign prostate hyperplasia, neurofibromatosis, dermatoses, and myelodysplastic syndromes.

The present invention further relates to pharmaceutical compositions comprising one or more of the compounds according to this invention and a pharmaceutically acceptable carrier or diluent.

The present invention further relates to pharmaceutical compositions comprising one or more of the compounds according to this invention and pharmaceutically acceptable auxiliaries and/or excipients.

The pharmaceutical compositions according to this invention are prepared by processes, which are known per se and familiar to the person skilled in the art. As pharmaceutical compositions, the compounds of the invention (=active compounds) are either employed as such, or preferably in combination with suitable pharmaceutical auxiliaries and/or excipients, e.g. in the form of tablets, coated tablets, dragees, pills, cachets, granules, capsules, caplets, suppositories, patches (e.g. as TTS), emulsions (such as e.g. micro-emulsions or lipid emulsions), suspensions (such as e.g. nano suspensions), gels, solubilisates or solutions (e.g. sterile solutions), or encapsuled in liposomes or as beta-cyclodextrine or beta-cyclodextrin derivative inclusion complexes or the like, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries, vehicles, excipients, diluents, carriers or adjuvants which are suitable for the desired pharmaceutical formulations, preparations or compositions on account of his/her expert knowledge. In addition to solvents, gel formers, ointment bases and other active compound excipients, for example antioxidants, dispersants, emulsifiers, preservatives, solubilizers (such as e.g. polyoxyethylenglyceroltriricinoleat 35, PEG 400, Tween 80, Captisol, Solutol HS15 or the like), colorants, complexing agents, permeation promoters, stabilizers, fillers, binders, thickeners, disintegrating agents, buffers, pH regulators (e.g. to obtain neutral, alkaline or acidic formulations), polymers, lubricants, coating agents, propellants, tonicity adjusting agents, surfactants, flavorings, sweeteners or dyes, can be used.

In particular, auxiliaries and/or excipients of a type appropriate to the desired formulation and the desired mode of administration are used.

The administration of the compounds, pharmaceutical compositions or combinations according to the invention may be performed in any of the generally accepted modes of administration available in the art. Illustrative examples of suitable modes of administration include intravenous, oral, nasal, parenteral, topical, transdermal and rectal delivery. Oral and intravenous deliveries are preferred.

Generally, the pharmaceutical compositions according to the invention can be administered such that the dose of the active compound is in the range customary for Pi3K/Akt pathway inhibitors. In particular, a dose in the range of from 0.01 to 4000 mg of the active compound per day is preferred for an average adult patient having a body weight of 70 kg. In this respect, it is to be noted that the dose is dependent, for example, on the specific compound used, the species treated, age, body weight, general health, sex and diet of the subject treated, mode and time of administration, rate of excretion, severity of the disease to be treated and drug combination.

The pharmaceutical composition can be administered in a single dose per day or in multiple subdoses, for example, 2 to 4 doses per day. A single dose unit of the pharmaceutical composition can contain e.g. from 0.01 mg to 4000 mg, preferably 0.1 mg to 2000 mg, more preferably 0.5 to 1000 mg, most preferably 1 to 500 mg, of the active compound. Furthermore, the pharmaceutical composition can be adapted to weekly, monthly or even more infrequent administration, for example by using an implant, e.g. a subcutaneous or intramuscular implant, by using the active compound in form of a sparingly soluble salt or by using the active compound coupled to a polymer.

The choice of the optimal dosage regime and duration of medication, particularly the optimal dose and manner of administration of the active compounds necessary in each case can be determined by a person skilled in the art.

The present invention further relates to combinations comprising one or more first active ingredients selected from the compounds of the invention and one or more second active ingredients selected from chemotherapeutic anti-cancer agents and target-specific anti-cancer agents e.g. for treating, preventing or ameliorating diseases responsive or sensitive to inhibition of the Pi3K/Akt pathway, such as hyperproliferative diseases of benign or malignant behaviour and/or disorders responsive to the induction of apoptosis, particularly cancer, such as e.g. any of those cancer diseases described above.

The invention further relates to the use of a pharmaceutical composition comprising one or more of the compounds according to this invention as sole active ingredient(s) and a pharmaceutically acceptable carrier or diluent in the manufacture of pharmaceutical products for the treatment and/or prophylaxis of the illnesses mentioned above.

Depending upon the particular disease, to be treated or prevented, additional therapeutic active agents, which are normally administered to treat or prevent that disease, may optionally be coadministered with the compounds according to this invention. As used herein, additional therapeutic agents that are normally administered to treat or prevent a particular disease are known as appropriate for the disease being treated.

The above mentioned second active ingredient, which is a chemotherapeutic anti-cancer agents, includes but is not limited to (i) alkylating/carbamylating agents such as Cyclophosphamid (Endoxan®), Ifosfamid (Holoxan®), Thiotepa (Thiotepa Lederle®), Melphalan (Alkeran®), or chloroethylnitrosourea (BCNU); (ii) platinum derivatives like cis-platin (Platinex® BMS), oxaliplatin (Eloxatin®), satraplatin or carboplatin (Cabroplat® BMS); (iii) antimitotic agents/tubulin inhibitors such as vinca alkaloids (vincristine, vinblastine, vinorelbine), taxanes such as Paclitaxel (Taxol®), Docetaxel (Taxotere®) and analogs as well as new formulations and conjugates thereof (like the nanoparticle formulation Abraxane® with paclitaxel bound to albumin), epothilones such as Epothilone B (Patupilone®), Azaepothilone (Ixabepilone®) or ZK-EPO, a fully synthetic epothilone B analog; (iv) topoisomerase inhibitors such as anthracyclines (exemplified by Doxorubicin/Adriblastin®), epipodophyllotoxines (exemplified by Etoposide/Etopophos®) and camptothecin and camptothecin analogs (exemplified by Irinotecan/Camptosar® or Topotecan/Hycamtin®); (v) pyrimidine antagonists such as 5-fluorouracil (5-FU), Capecitabine (Xeloda®), Arabinosylcytosine/Cytarabin (Alexan®) or Gemcitabine (Gemzar®); (vi) purin antagonists such as 6-mercaptopurine (PuriNethol®), 6-thioguanine or fludarabine (Fludara®) and (vii) folic acid antagonists such as methotrexate (Farmitrexat®) or premeterxed (Alimta®).

The above mentioned second active ingredient, which is a target specific anti-cancer agent, includes but is not limited to (i) kinase inhibitors such as e.g. Imatinib (Glivec®), ZD-1839/Gefitinib (Iressa®), Bay43-9006 (Sorafenib, Nexavar®), SU11248/Sunitinib (Sutent®), OSI-774/Erlotinib (Tarceva®), Dasatinib (Sprycel®), Lapatinib (Tykerb®), or, see also below, Vatalanib, Vandetanib (Zactima®) or Pazopanib; (ii) proteasome inhibitors such as PS-341/Bortezumib (Velcade®); (iii) histone deacetylase inhibitors like SAHA (Zolinza®), PXD101, MS275, MGCD0103, Depsipeptide/FK228, NVP-LBH589, Valproic acid (VPA), CRA/PCI 24781, ITF2357, SB939 and butyrates (iv) heat shock protein 90 inhibitors like 17-allylaminogeldanamycin (17-AAG) or 17-dimethylaminogeldanamycin (17-DMAG); (v) vascular targeting agents (VTAs) like combretastin A4 phosphate or AVE8062/AC7700 and anti-angiogenic drugs like the VEGF antibodies, such as Bevacizumab (Avastin®), or KDR tyrosine kinase inhibitors such as PTK787/ZK222584 (Vatalanib®) or Vandetanib (Zactima®) or Pazopanib; (vi) monoclonal antibodies such as Trastuzumab (Herceptin®), Rituximab (MabThera/Rituxan®), Alemtuzumab (Campath®), Tositumomab (Bexxar®), C225/Cetuximab (Erbitux®), Avastin (see above) or Panitumumab (Vectibix®) as well as mutants and conjugates of monoclonal antibodies, e.g. Gemtuzumab ozogamicin (Mylotarg®) or Ibritumomab tiuxetan (Zevalin®), and antibody fragments; (vii) oligonucleotide based therapeutics like G-3139/Oblimersen (Genasense®) or the DNMT1 inhibitor MG98; (viii) Toll-like receptor/TLR 9 agonists like Promune®, TLR 7 agonists like Imiquimod (Aldara®) or Isatoribine and analogues thereof, or TLR 7/8 agonists like Resiquimod as well as immunostimulatory RNA as TLR 7/8 agonists; (ix) protease inhibitors; (x) hormonal therapeutics such as anti-estrogens (e.g. Tamoxifen or Raloxifen), antiandrogens (e.g. Flutamide or Casodex), LHRH analogs (e.g. Leuprolide, Goserelin or Triptorelin) and aromatase inhibitors (e.g. Femara, Arimedex or Aromasin).

Other target specific anti-cancer agents includes bleomycin, retinoids such as all-trans retinoic acid (ATRA), DNA methyltransferase inhibitors such as 5-Aza-2'-deoxycytidine (Decitabine, Dacogen®) and 5-azacytidine (Vidaza®), alanosine, cytokines such as interleukin-2, interferons such as interferon α2 or interferon-γ, bcl2 antagonists (e.g. ABT-737 or analogs), death receptor agonists, such as TRAIL, DR4/5 agonistic antibodies, FasL and TNF-R agonists (e.g. TRAIL receptor agonists like mapatumumab or lexatumumab).

Specific examples of the second active ingredient include, but is not limited 5 FU, actinomycin D, ABARELIX, ABCIXIMAB, ACLARUBICIN, ADAPALENE, ALEMTUZUMAB, ALTRETAMINE, AMINOGLUTETHIMIDE, AMIPRILOSE, AMRUBICIN, ANASTROZOLE, ANCITABINE, ARTEMISININ, AZATHIOPRINE, BASILIXIMAB, BENDAMUSTINE, BEVACIZUMAB, BEXXAR, BICALUTAMIDE, BLEOMYCIN, BORTEZOMIB, BROXURIDINE, BUSULFAN, CAMPATH, CAPECITABINE, CARBOPLATIN, CARBOQUONE, CARMUSTINE, CETRORELIX, CHLORAMBUCIL, CHLORMETHINE, CISPLATIN, CLADRIBINE, CLOMIFENE, CYCLOPHOSPHAMIDE, DACARBAZINE, DACLIZUMAB, DACTINOMYCIN, DASATINIB, DAUNORUBICIN, DECITABINE, DESLORELIN, DEXRAZOXANE, DOCETAXEL, DOXIFLURIDINE, DOXORUBICIN, DROLOXIFENE, DROSTANOLONE, EDELFOSINE, EFLORNITHINE, EMITEFUR, EPIRUBICIN, EPITIOSTANOL, EPTAPLATIN, ERBITUX, ERLOTINIB, ESTRAMUSTINE, ETOPOSIDE, EXEMESTANE, FADROZOLE, FINASTERIDE, FLOXURIDINE, FLUCYTOSINE, FLUDARABINE, FLUOROURACIL, FLUTAMIDE, FORMESTANE, FOSCARNET, FOSFESTROL, FOTEMUSTINE, FULVESTRANT, GEFITINIB, GENASENSE, GEMCITABINE, GLIVEC, GOSERELIN, GUSPERIMUS, HERCEPTIN, IDARUBICIN, IDOXURIDINE, IFOSFAMIDE, IMATINIB, IMPROSULFAN, INFLIXIMAB, IRINOTECAN, IXABEPILONE, LANREOTIDE, LAPATINIB, LETROZOLE, LEUPRORELIN, LOBAPLATIN, LOMUSTINE, LUPROLIDE, MELPHALAN, MERCAPTOPURINE, METHOTREXATE, METUREDEPA, MIBOPLATIN, MIFEPRISTONE, MILTEFOSINE, MIRIMOSTIM, MITOGUAZONE, MITOLACTOL, MITOMYCIN, MITOXANTRONE, MIZORIBINE, MOTEXAFIN, MYLOTARG, NARTOGRASTIM, NEBAZUMAB, NEDAPLATIN, NILUTAMIDE, NIMUSTINE, OCTREOTIDE, ORMELOXIFENE, OXALIPLATIN, PACLITAXEL, PALIVIZUMAB, PANITUMUMAB, PATUPILONE, PAZOPANIB, PEGASPARGASE, PEGFILGRASTIM, PEMETREXED, PENTETREOTIDE, PENTOSTATIN, PERFOSFAMIDE, PIPOSULFAN, PIRARUBICIN, PLICAMYCIN, PREDNIMUSTINE, PROCARBAZINE, PROPAGERMANIUM, PROSPIDIUM CHLORIDE, RALOXIFEN, RALTITREXED, RANIMUSTINE, RANPIRNASE, RASBURICASE, RAZOXANE, RITUXIMAB, RIFAMPICIN, RITROSULFAN, ROMURTIDE, RUBOXISTAURIN, SARGRAMOSTIM, SATRAPLATIN, SIROLIMUS, SOBUZOXANE, SORAFENIB, SPIROMUSTINE, STREPTOZOCIN, SUNITINIB, TAMOXIFEN, TASONERMIN, TEGAFUR, TEMOPORFIN, TEMOZOLOMIDE, TENIPOSIDE, TESTOLACTONE, THIOTEPA, THYMALFASIN, TIAMIPRINE, TOPOTECAN, TOREMIFENE, TRAIL, TRASTUZUMAB, TREOSULFAN, TRIAZIQUONE, TRIMETREXATE, TRIPTORELIN, TROFOSFAMIDE, UREDEPA, VALRUBICIN, VATALANIB, VANDETANIB, VERTEPORFIN, VINBLASTINE, VINCRISTINE, VINDESINE, VINORELBINE, VOROZOLE, ZEVALIN and ZOLINZA.

The anti-cancer agents mentioned herein above as combination partners of the compounds according to this invention are meant to include pharmaceutically acceptable derivatives thereof, such as e.g. their pharmaceutically acceptable salts.

The person skilled in the art is aware of the total daily dosage(s) and administration form(s) of the additional therapeutic agent(s) coadministered. Said total daily dosage(s) can vary within a wide range.

In practicing the present invention, the compounds according to this invention may be administered in combination therapy separately, sequentially, simultaneously, concurrently or chronologically staggered (such as e.g. as combined unit dosage forms, as separate unit dosage forms, as adjacent discrete unit dosage forms, as fixed or non-fixed combinations, as kit-of-parts or as admixtures) with one or more standard therapeutics (chemotherapeutic and/or target specific anti-cancer agents), in particular art-known anti-cancer agents, such as any of e.g. those mentioned above.

In this context, the present invention further relates to a combination comprising a first active ingredient, which is at least one compound according to this invention, and a second active ingredient, which is at least one art-known anti-cancer agent, such as e.g. one or more of those mentioned herein above, for separate, sequential, simultaneous, concurrent or chronologically staggered use in therapy, such as e.g. in therapy of any of those diseases mentioned herein.

The term "combination" in the present invention is used as known to persons skilled in the art and may be present as a fixed combination, a non-fixed combination or kit-of-parts.

A "fixed combination" in the present invention is used as known to persons skilled in the art and is defined as a combination wherein the said first active ingredient and the said second active ingredient are present together in one unit dosage or in a single entity. One example of a "fixed combination" is a pharmaceutical composition wherein the said first active ingredient and the said second active ingredient are present in admixture for simultaneous administration, such as in a formulation. Another example of a "fixed combination" is a pharmaceutical combination wherein the said first active ingredient and the said second active ingredient are present in one unit without being in admixture.

A non-fixed combination or "kit-of-parts" in the present invention is used as known to persons skilled in the art and is defined as a combination wherein the said first active ingredient and the said second active ingredient are present in more than one unit. One example of a non-fixed combination or kit-of-parts is a combination wherein the said first active ingredient and the said second active ingredient are present separately. The components of the non-fixed combination or kit-of-parts may be administered separately, sequentially, simultaneously, concurrently or chronologically staggered.

The present invention further relates to a pharmaceutical composition comprising a first active ingredient, which is at least one compound according to this invention, and a second active ingredient, which is at least one art-known anti-cancer agent, such as e.g. one or more of those mentioned herein above, and, optionally, a pharmaceutically acceptable carrier or diluent, for separate, sequential, simultaneous, concurrent or chronologically staggered use in therapy.

The present invention further relates to a combination product comprising
a.) at least one compound according to this invention formulated with a pharmaceutically acceptable carrier or diluent, and
b.) at least one art-known anti-cancer agent, such as e.g. one or more of those mentioned herein above, formulated with a pharmaceutically acceptable carrier or diluent.

The present invention further relates to a kit-of-parts comprising a preparation of a first active ingredient, which is a compound according to this invention, and a pharmaceutically acceptable carrier or diluent; a preparation of a second active ingredient, which is an art-known anti-cancer agent, such as one of those mentioned above, and a pharmaceutically acceptable carrier or diluent; for simultaneous, concurrent, sequential, separate or chronologically staggered use in therapy. Optionally, said kit comprises instructions for its use in therapy, e.g. to treat hyperproliferative diseases and diseases responsive or sensitive to inhibition of the Pi3K/Akt pathway, such as e.g. benign or malignant neoplasia, particularly cancer, more precisely, any of those cancer diseases described above.

The present invention further relates to a combined preparation comprising at least one compound according to this invention and at least one art-known anti-cancer agent for simultaneous, concurrent, sequential or separate administration.

The present invention further relates to combinations, compositions, formulations, preparations or kits according to the present invention having Pi3K/Akt pathway inhibitory activity.

In addition, the present invention further relates to a method for treating in combination therapy hyperproliferative diseases and/or disorders responsive to the induction of apoptosis, such as e.g. cancer, in a patient comprising administering a combination, composition, formulation, preparation or kit as described herein to said patient in need thereof.

In addition, the present invention further relates to a method for treating hyperproliferative diseases of benign or malignant behaviour and/or disorders responsive to the induction of apoptosis, such as e.g. cancer, in a patient comprising administering in combination therapy separately, simultaneously, concurrently, sequentially or chronologically staggered a pharmaceutically active and therapeutically effective and tolerable amount of a pharmaceutical composition, which comprises a compound according to this invention and a pharmaceutically acceptable carrier or diluent, and a pharmaceutically active and therapeutically effective and tolerable amount of one or more art-known anti-cancer agents, such as e.g. one or more of those mentioned herein, to said patient in need thereof.

In further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering separately, simultaneously, concurrently, sequentially or chronologically staggered to said patient in need thereof an amount of a first active compound, which is a compound according to the present invention, and an amount of at least one second active compound, said at least one second active compound being a standard therapeutic agent, particularly at least one art-known anti-cancer agent, such as e.g. one or more of those chemotherapeutic and target-specific anti-cancer agents mentioned herein, wherein the amounts of the first active compound and said second active compound result in a therapeutic effect.

In yet further addition, the present invention relates to a method for treating, preventing or ameliorating hyperproliferative diseases and/or disorders responsive to induction of apoptosis, such as e.g. benign or malignant neoplasia, e.g. cancer, particularly any of those cancer diseases mentioned herein, in a patient comprising administering a combination according to the present invention.

In addition, the present invention further relates to the use of a composition, combination, formulation, preparation or kit according to this invention in the manufacture of a pharmaceutical product, such as e.g. a commercial package or a medicament, for treating, preventing or ameliorating hyperproliferative diseases, such as e.g. cancer, and/or disorders responsive to the induction of apoptosis, particularly those diseases mentioned herein, such as e.g. malignant or benign neoplasia.

The present invention further relates to a commercial package comprising one or more compounds of the present invention together with instructions for simultaneous, concurrent, sequential or separate use with one or more chemotherapeutic and/or target specific anti-cancer agents, such as e.g. any of those mentioned herein.

The present invention further relates to a commercial package consisting essentially of one or more compounds of the present invention as sole active ingredient together with instructions for simultaneous, concurrent, sequential or separate use with one or more chemotherapeutic and/or target specific anti-cancer agents, such as e.g. any of those mentioned herein.

The present invention further relates to a commercial package comprising one or more chemotherapeutic and/or target specific anti-cancer agents, such as e.g. any of those mentioned herein, together with instructions for simultaneous, concurrent, sequential or separate use with one or more compounds according to the present invention.

The compositions, combinations, preparations, formulations, kits or packages mentioned in the context of the combination therapy according to this invention may also include more than one of the compounds according to this invention and/or more than one of the art-known anti-cancer agents mentioned.

The first and second active ingredient of a combination or kit-of-parts according to this invention may be provided as separate formulations (i.e. independently of one another), which are subsequently brought together for simultaneous, concurrent, sequential, separate or chronologically staggered use in combination therapy; or packaged and presented together as separate components of a combination pack for simultaneous, concurrent, sequential, separate or chronologically staggered use in combination therapy.

The type of pharmaceutical formulation of the first and second active ingredient of a combination or kit-of-parts according to this invention can be according, i.e. both ingredients are formulated in separate tablets or capsules, or can be different, i.e. suited for different administration forms, such as e.g. one active ingredient is formulated as tablet or capsule and the other is formulated for e.g. intravenous administration.

The amounts of the first and second active ingredients of the combinations, compositions or kits according to this invention may together comprise a therapeutically effective amount for the treatment, prophylaxis or amelioration of a hyperproliferative diseases and/or a disorder responsive to the induction of apoptosis, particularly one of those diseases mentioned herein, such as e.g. malignant or benign neoplasia, especially cancer, like any of those cancer diseases mentioned herein.

In addition, compounds according to the present invention can be used in the pre- or post-surgical treatment of cancer.

In further addition, compounds of the present invention can be used in combination with radiation therapy.

A combination according to this invention can refer to a composition comprising both the compound(s) according to this invention and the other active anti-cancer agent(s) in a fixed combination (fixed unit dosage form), or a medicament pack comprising the two or more active ingredients as discrete separate dosage forms (non-fixed combination). In case of a medicament pack comprising the two or more active ingredients, the active ingredients are preferably packed into blister cards, which are suited for improving compliance.

Each blister card preferably contains the medicaments to be taken on one day of treatment. If the medicaments are to be taken at different times of day, the medicaments can be disposed in different sections on the blister card according to the different ranges of times of day at which the medicaments are to be taken (for example morning and evening or morning, midday and evening). The blister cavities for the medicaments to be taken together at a particular time of day are accommodated in the respective range of times of day. The various times of day are, of course, also put on the blister in a clearly visible way. It is also possible, of course, for example to indicate a period in which the medicaments are to be taken, for example stating the times.

The daily sections may represent one line of the blister card, and the times of day are then identified in chronological sequence in this column.

Medicaments which must be taken together at a particular time of day are placed together at the appropriate time on the blister card, preferably a narrow distance apart, allowing them to be pushed out of the blister easily, and having the effect that removal of the dosage form from the blister is not forgotten.

Biological Investigations
Cellular PI3K/Akt Pathway Assay

In order to study the cellular activity of the compounds according to the present invention, an Enzyme Linked Immunosorbent Assay (ELISA)-based assay has been used specific phospho-AKT. The assay is based on a Sandwich ELISA kit (PathScan™ Phospho-Akt1 (Ser473); Cell Signaling, USA; #7160).

The ELISA Kit detects endogenous levels of phosphorylated Akt protein. A phospho-Akt (Ser473) antibody (Cell Signaling, USA; #9271) has been coated onto the microwells. After incubation with cell lysates, the coated antibody captures the phosphorylated Akt protein. Following extensive washing, Akt1 monoclonal antibody (Cell Signaling, USA; #2967) is added to detect the captured phospho-Akt1 protein. HRP-linked anti-mouse antibody (HRP: horseradish peroxidase; Cell Signaling, USA; #7076) is then used to recognize the bound detection antibody. HRP substrate (=3,3',5,5'-tetramethylbenzidine (TMB); Cell Signaling, USA; #7160) is added to develop colour. The magnitude of optical density for this developed color is proportional to the quantity of phosphorylated Akt protein. MCF7 cells (ATCC HTB-22) are seeded into 96 well fate bottom plates at a density of 10000 cells/well. 24 hours after seeding, the cells are serum starved using low-serum medium (IMEM media including 0.1% charcoal treated FCS (FCS: fetal calf serum)). After 24 hours 1 µl each of the compound dilutions (test compounds were dissolved as 10 mM solutions in dimethylsulfoxide (DMSO) and subsequently diluted) are added into each well of the 96 well plates and incubated for 48 h at 37° C. in a humidified atmosphere containing 5% $CO_2$. To stimulate Akt phosphorylation, β-Heregulin (20 ng/ml β-HRG) is added in parallel to the compounds. Wells containing unstimulated control cells (no β-Heregulin stimulation) are incubated with or without the diluted compound. Wells containing untreated control cells (no compound) are filled with medium containing 0.5% v:v DMSO and are or are not stimulated with β-Heregulin.

Cells are harvested and lysed with brief sonification in 1× cell lysis buffer (20 mM Tris (pH7.5), 150 mM NaCl, 1 mM ethylene diaminetetraacetate (EDTA), 1 mM ethylene glycolbis(2-aminoethyl)-N,N,N',N'-tetraacetic acid (EGTA), 1 vol % Triton X-100, 2.5 mM sodium pyrophosphate, 1 mM β-glycerolphosphate, 1 mM $Na_3VO_4$, 1 µg/ml leupeptin). The lysate is centrifuged for 10 min. at 4° C. and the supernatant is transferred to a new tube. 100 µl of sample diluent (0.1 vol % Tween-20, 0.1 vol % sodium azide in phosphate buffered saline (PBS)) are added to a microcentrifuge tube and 100 µl of cell lysate are transferred into the tube and vortexed. 100 µl of each diluted cell lysate are added to the appropriate ELISA well, and incubated overnight at 4° C. The plates are washed 4 times with 1× wash buffer (1 vol % tween-20, 0.33 vol % thymol, in PBS). Next 100 µl of detection antibody (Akt1 (2H10) monoclonal detection antibody; Cell Signaling, USA; #2967) are added to each well and incubation continued for 1 h at 37° C. The washing procedure is repeated between each step. 100 µl of secondary antibody (anti-mouse IgG HRP-linked antibody; Cell Signaling, USA; #7076) are added to each well and incubated for 30 min. at 37° C. Than, 100 µl of TMB substrate (0.05% 3,3',5,5' tetramethylbenzidine, 0.1% hydrogen peroxide, complex polypeptides in a buffered solution; Cell Signaling, USA; #7160) are added to each well and incubated for 30 min. at 25° C. Finally 100 µl of STOP solution (0.05 vol % α and β unsaturated carbonyl compound) are added to each well and the plate are shaked gently. The absorbance is measured at λ 450 nm (Wallac Victor2; Perkin Elmer, USA) within 30 min. after adding the STOP solution. The analysis of the data is performed using a statistical program (Excel; Microsoft, USA). Preferred compounds show an inhibitory activity towards Akt phosphorylation below 10 µM.

Cellular pGSK3 Assay:

In order to study the cellular activity of the compounds according to the present invention, an ELISA-based assay has been established for the phosphorylated protein glycogen synthetase kinase 3 (GSK3). The assay is based on a solid phase sandwich ELISA that detects endogenous levels of phosphorylated GSK3 using a phospho-GSK3 (Ser9) specific antibody (BioSource International, Inc.; Catalog #KHO0461). After incubation with cell lysates, the coated antibody captures the phosphorylated GSK3 protein. Following extensive washing, GSK3 polyclonal antibody is added to detect the captured phospho-GSK3 protein. Secondary antibody (anti-rabbit IgG-HRP) is then used to recognize the bound detection antibody. After the second incubation and washing to remove all the excess anti-rabbit IgG-HRP, a substrate solution is added, which is acted upon by the bound enzyme to produce color. The intensity of this colored product is directly proportional to the concentration of GSK-3β [pS9] present in the original specimen.

MCF7 cells (ATCC HTB-22) were seeded into 96 well fate bottom plates at a density of 10000 cells/well. After 24 h 1 µl each of the compound dilutions (test compounds were dissolved as 10 mM solutions in dimethylsulfoxide (DMSO) and subsequently diluted) were added into each well of the 96 well plates and incubated for 48 h at 37° C. in a humidified atmosphere containing 5% $CO_2$. Cells were harvested and lysed in cell extraction buffer (10 mM Tris, pH 7.4, 100 mM NaCl, 1 mM EDTA, 1 mM EGTA, 1 mM NaF, 20 mM $Na_4P_2O_7$, 2 mM $Na_3VO_4$, 1% Triton X-100, 10 vol % glycerol, 0.1 vol % SDS, 0.5 vol % deoxycholate, 1 mM phenylmethylsulfonylfluorid (PMSF)). The lysate were centrifuged for 10 min. at 4° C. and the supernatant were transferred to a new tube. 50 µl of sample diluent (standard diluent buffer, Biosource) were added and 100 µl of cell lysate transferred into the tube and vortexed. 100 µl of each diluted cell lysate were added to the appropriate ELISA well plate and incubated for 3 h at room temperature. The plates were washed 4 times with 1× wash buffer (Biosource). 50 µl of detection antibody (GSK3 (Ser9) detection antibody; BioSource) were added to each well and incubated for 30 min. at room temperature. The washing procedure was repeated between each step. 100 µl of HRP-linked secondary antibody (anti-mouse IgG HRP-linked antibody) were added to each well and incubated for 30 min. at room temperature. 100 µl of TMB substrate (0.05 vol % 3,3',5,5' tetramethylbenzidine, 0.1 vol % hydrogen peroxide, complex polypeptides in a buffered solution; Biosource) were added to each well and incubated for 30 min. at room temperature. Finally 100 µl of Stop solution (0.05 vol % α and β unsaturated carbonyl compound) were added to each well and the plate were shaked gently for a few seconds. The absorbance was measured at λ 450 nm (Wallac Victor2; Perkin Elmer, USA) within 30 min. after adding the stop solution.

The analysis of the data was performed using a statistical program (Excel; Microsoft, USA) and the IC50 of pGSK3 inhibition was determined.

TABLE

Cellular PI3K/Akt pathway inhibition//Cellular pGSK3 assay

| Example No. | Cellular PI3K/Akt pathway assay | Cellular pGSK3 pathway assay |
|---|---|---|
| 1 | +++ | ++ |
| 2 | +++ | ++ |
| 3 | +++ | +++ |
| 4 | | ++ |
| 5 | +++ | +++ |
| 6 | +++ | ++ |
| 7 | +++ | ++ |
| 8 | +++ | ++ |
| 9 | ++ | ++ |
| 10 | +++ | +++ |
| 11 | +++ | ++ |
| 12 | +++ | +++ |
| 13 | +++ | ++ |
| 14 | +++ | ++ |
| 15 | + | ++ |
| 16 | ++ | ++ |
| 17 | +++ | ++ |
| 18 | ++ | ++ |
| 19 | +++ | +++ |
| 20 | + | + |
| 21 | +++ | ++ |
| 22 | +++ | ++ |
| 23 | +++ | ++ |
| 24 | +++ | +++ |
| 25 | +++ | +++ |
| 26 | | ++ |
| 27 | +++ | ++ |
| 28 | | ++ |
| 29 | +++ | +++ |
| 30 | ++ | +++ |
| 31 | +++ | +++ |
| 32 | +++ | ++ |
| 33 | ++ | + |
| 34 | +++ | +++ |
| 35 | | ++ |
| 36 | | ++ |
| 37 | +++ | ++ |
| 38 | +++ | +++ |
| 39 | +++ | ++ |
| 40 | +++ | +++ |
| 41 | +++ | ++ |
| 42 | +++ | + |
| 43 | ++ | |
| 44 | +++ | ++ |
| 45 | | |
| 46 | +++ | ++ |
| 47 | | |
| 48 | | |
| 49 | | |
| 50 | | |
| 51 | | |
| 52 | | |
| 53 | | |
| 54 | | |
| 55 | | |
| 56 | | |
| 57 | | |
| 58 | | |
| 59 | +++ | |
| 60 | | |
| 61 | +++ | |
| 62 | +++ | |
| 63 | | |
| 64 | | |
| 65 | +++ | |
| 66 | +++ | |
| 67 | | |
| 68 | +++ | |
| 69 | | |
| 70 | | |
| 71 | +++ | |
| 72 | | |
| 73 | | |
| 74 | | |

TABLE-continued

Cellular PI3K/Akt pathway inhibition//Cellular pGSK3 assay

| Example No. | Cellular PI3K/Akt pathway assay | Cellular pGSK3 pathway assay |
|---|---|---|
| 75 | | |
| 76 | | |
| 77 | +++ | |
| 78 | | |
| 79 | | |
| 80 | | |
| 81 | | |
| 82 | | |
| 83 | | |
| 84 | | |
| 85 | | |
| 86 | | |
| 87 | | |
| 88 | | |
| 89 | | |
| 90 | | |
| 91 | | |
| 92 | | |
| 93 | +++ | |
| 94 | | |
| 95 | | |
| 96 | | |
| 97 | | |
| 98 | +++ | |
| 99 | | |
| 100 | | |
| 101 | | |
| 102 | | |
| 103 | | |
| 104 | | |
| 105 | +++ | |
| 106 | +++ | |
| 107 | | |
| 108 | | |
| 109 | | |
| 110 | | |
| 111 | | |
| 112 | | |
| 113 | | |
| 114 | | |
| 115 | | |
| 116 | | |
| 117 | +++ | |
| 118 | | |
| 119 | | |
| 120 | | |
| 121 | | |
| 122 | | |
| 123 | | |
| 125 | | |
| 124 | +++ | |
| 126 | | |
| 127 | | |

IC50 > 10 μM +
10 μM > IC50 > 1 μM ++
1 μM > IC50 +++

Cellular Proliferation/Cytotoxicity Assay:

The anti-proliferative activity of the compounds as described herein, is evaluated using the OvCAR3, HCT116 and A549 cell lines and the Alamar Blue (Resazurin) cell viability assay (O'Brien et al. Eur J Biochem 267, 5421-5426, 2000). Resazurin is reduced to the fluorescent resorufin by cellular dehydrogenase activity, correlating with viable, proliferating cells. Test compounds are dissolved as 10 mM solutions in DMSO and subsequently diluted. Cells like HCT116 or A549 cells were seeded into 96 well flat bottom plates at a density of 10000 cells/well (OvCAR3 cells), 1000 cells/well (HCT116 cells) or 2000 cells/well (A549 cells) in a volume of 200 μl/well. 24 hours after seeding, 1 μl each of the compound dilutions are added into each well of the 96 well plates. Each compound dilution is tested as at least as duplicates. Wells containing untreated control cells were filled with 200 μl DMEM (Dulbecco's Modified Eagle Medium) containing 0.5 vol % v:v DMSO. The cells are then incubated with the substances for 72 h at 37° C. in a humidified atmosphere containing 5 vol % $CO_2$. To determine the viability of the cells, 20 μl of a Resazurin solution (90 mg/l) are added. After 4 h incubation at 37° C., the fluorescence is measured by extinction at λ=544 nm and an emission of λ=590 nm (Wallac Victor2; Perkin Elmer, USA). For the calculation of the cell viability, the emission value from untreated cells is set as 100% viability and the fluorescence intensity of treated cells are set in relation to the values of untreated cells. Viabilities are expressed as % values. The corresponding IC50 values of the compounds for cytotoxic activity are determined from the concentration-effect curves by means of non-linear regression. The analysis of the data is performed using a biostatistical program (Graph Pad Prism, USA).

Representative IC50 values for anti-proliferative/cytotoxic potency determined in the aforementioned assay follow from the following table, in which the numbers of the compound correspond to the numbers of the examples.

TABLE

Anti-proliferative/Cytotoxic activity (OvCAR3 cells and A549 cells)

| Example No. | Anti-proliferative/ Cytotoxic activity (A549 cells) | Anti-proliferative/ Cytotoxic activity (OvCAR3 cells) |
|---|---|---|
| 1 | + | ++ |
| 2 | ++ | ++ |
| 3 | | ++ |
| 4 | + | + |
| 5 | ++ | ++ |
| 6 | ++ | ++ |
| 7 | ++ | ++ |
| 8 | ++ | ++ |
| 9 | ++ | + |
| 10 | ++ | ++ |
| 11 | ++ | ++ |
| 12 | ++ | ++ |
| 13 | ++ | ++ |
| 14 | ++ | ++ |
| 15 | ++ | + |
| 16 | + | ++ |
| 17 | ++ | ++ |
| 18 | + | ++ |
| 19 | ++ | ++ |
| 20 | + | + |
| 21 | ++ | ++ |
| 22 | + | ++ |
| 23 | + | ++ |
| 24 | ++ | ++ |
| 25 | ++ | ++ |
| 26 | + | ++ |
| 27 | ++ | ++ |
| 28 | + | ++ |
| 29 | + | ++ |
| 30 | + | ++ |
| 31 | + | ++ |
| 32 | ++ | ++ |
| 33 | ++ | ++ |
| 34 | + | ++ |
| 35 | + | ++ |
| 36 | + | + |
| 37 | + | ++ |
| 38 | + | ++ |
| 39 | + | ++ |
| 40 | + | ++ |
| 41 | + | ++ |
| 42 | ++ | ++ |
| 43 | | |
| 44 | + | ++ |

TABLE-continued

Anti-proliferative/Cytotoxic activity (OvCAR3 cells and A549 cells)

| Example No. | Anti-proliferative/ Cytotoxic activity (A549 cells) | Anti-proliferative/ Cytotoxic activity (OvCAR3 cells) |
|---|---|---|
| 45 | + | |
| 46 | ++ | |
| 47 | + | |
| 48 | + | |
| 49 | | |
| 50 | + | |
| 51 | ++ | |
| 52 | + | |
| 53 | ++ | |
| 54 | ++ | |
| 55 | + | |
| 56 | ++ | |
| 57 | ++ | |
| 58 | ++ | |
| 59 | ++ | |
| 60 | ++ | |
| 61 | + | |
| 62 | + | |
| 63 | + | |
| 64 | ++ | |
| 65 | ++ | |
| 66 | ++ | |
| 67 | ++ | |
| 68 | ++ | |
| 69 | ++ | |
| 70 | ++ | |
| 71 | ++ | |
| 72 | ++ | |
| 73 | ++ | |
| 74 | ++ | |
| 75 | + | |
| 76 | ++ | |
| 77 | + | |
| 78 | ++ | |
| 79 | + | |
| 80 | + | |
| 81 | + | |
| 82 | ++ | |
| 83 | + | |
| 84 | + | |
| 85 | + | |
| 86 | + | |
| 87 | ++ | |
| 88 | ++ | |
| 89 | ++ | |
| 90 | + | |
| 91 | ++ | |
| 92 | ++ | |
| 93 | ++ | |
| 94 | ++ | |
| 95 | + | |
| 96 | ++ | |
| 97 | ++ | |
| 98 | + | |
| 99 | ++ | |
| 100 | ++ | |
| 101 | ++ | |
| 102 | ++ | |
| 103 | ++ | |
| 104 | ++ | |
| 105 | ++ | |
| 106 | + | |
| 107 | ++ | |
| 108 | ++ | |
| 109 | ++ | |
| 110 | ++ | |
| 111 | ++ | |
| 112 | ++ | |
| 113 | ++ | |
| 114 | ++ | |
| 115 | + | |
| 116 | ++ | |
| 117 | + | |
| 118 | ++ | |
| 119 | ++ | |
| 120 | ++ | |
| 121 | ++ | |
| 122 | ++ | |
| 123 | ++ | |
| 125 | + | |
| 124 | + | |
| 127 | + | |
| 126 | ++ | |

IC50 > 10 μM +
10 μM > IC50 ++

Chemosensitization Assay:

The herein disclosed compounds are evaluated for the ability to sensitize cancer cells towards apoptotic stimuli. Inhibitors of Akt are tested alone and in combination with chemotherapeutic and targeted cancer therapeutics to determine the effect on apoptosis induction.

Cancer cells are seeded in 96 well plates at concentrations ranging from $2 \times 10^3$ to $1 \times 10^4$ cells per well in their respective growth media. 48-72 hours later, the apoptosis assay are set up as follows:

For combination assays with a chemotherapeutic agent especially preferred topoisomerase inhibitors (such as doxorubicin, etoposide, camptothecin or mitoxantrone) or antimitotic agents/tubulin inhibitors (such as vincristine), compounds are added at respective concentrations indicated and plates incubated at 37° C. in a $CO_2$ incubator for 18 hours. For standard combination assays utilizing treatment with chemotherapeutic agent are added at the same time at the respective concentrations indicated.

For combinations assays involving addition of targeted pro-apoptotic agents like the death receptor ligand TRAIL/Apo2L (Research Diagnostics) compounds are added for 1.5 hours prior to addition of TRAIL and plates incubated an additional 3 to 4 hours post TRAIL addition. In the case of the time course, plates are incubated for 2, 3, 4 and 6 hours with TRAIL ligand before ending the assay. For both procedures, total final volumes do not exceed 250 μl. At the end of the incubation time, the cells are pelleted by centrifugation (200× g; 10 min. at RT) and the supernatant is discarded. The cells are resuspended and incubated using lysis buffer for 30 min. at RT (Cell Death Detection ELISA$^{PLUS}$, Roche, Cat. No. 11774425001). After the centrifugation is repeated (200×g; 10 min. at RT) an aliquot of the supernatant is transferred to a streptavidin-coated well of a microplate. Followed by the incubation (2 h, RT) and binding of nucleosomes in the supernatant with, anti-histone antibody (biotin-labeled) and anti-DNA antibody (peroxidase-conjugated; Cell Death Detection ELISA$^{PLUS}$, Roche, Cat. No. 11774425 001). The antibody-nucleosome complexes are bound to the microplate. The immobilized antibody-histone complexes are washed three times at RT to remove cell components that are not immunoreactive. The substrate solution (2,2'-AZINO-bis[3-ethyl-benziazoline-6-sulfonic acid (ABTS); Cell Death Detection ELISA$^{PLUS}$, Roche, Cat. No. 11 774 425 001) is added and the samples were incubated for 15 min., RT. The amount of colored product is determined spectrophotometrically (absorbance at λ=405 nm). Data are expressed as percent activity of control with cisplatin used as a positive control. Apoptosis induction by 50 μM cisplatin is arbitrarily defined as 100 cisplatin units (100 CPU).

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding Indian application No. 1573/MUM/2007, filed Aug. 14, 2007, and of corresponding European application No. 07 118 733.0-2101, filed Oct. 18, 2007, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:
1. A compound of formula (I)

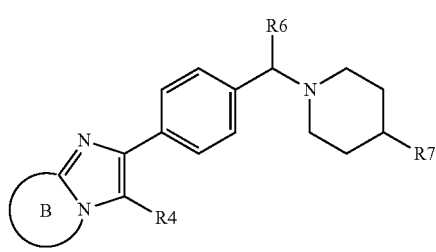

wherein ring B and the imidazole to which it is fused form a

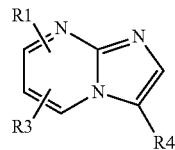

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10
R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, thiazolyl or oxazolyl,
R5 is 1-4C-alkyl, halogen or 1-4C-alkoxy,
R6 is hydrogen or 1-4C-alkyl,
R7 is —W—Y,
W is a monocyclic 5-membered heteroarylene comprising 1 nitrogen atom and optionally 1 or 2 further heteroatoms independently selected from oxygen, nitrogen and sulphur,
and wherein the heteroarylene is optionally substituted by R8,
R8 is 1-4C-alkyl or 3-7C-cycloalkyl,
Y is phenyl or a monocyclic 5- or 6-membered heteroaryl comprising 1 nitrogen atom and optionally 1 or 2 further heteroatoms independently selected from oxygen, nitrogen, sulphur,
and wherein the heteroaryl is optionally substituted by R9,
R9 is 1-4C-alkyl, 1-4C-alkoxy or halogen,
R10 is hydrogen or 1-4C-alkyl,
or a pharmaceutically acceptable salt, tautomer, or stereoisomer of said compound, or a pharmaceutically acceptable salt of said tautomer or said stereoisomer.

2. The compound according to claim 1, wherein ring B and the imidazole to which it is fused form a

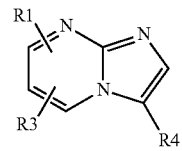

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR 10
R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, oxazolyl or thiazolyl,
R5 is 1-4C-alkyl, halogen or 1-4C-alkoxy,
R6 is hydrogen or methyl,
R7 is —W—Y,
W is triazolylene, pyrazolylene, oxadiazolylene or imidazolylene, each of which is optionally substituted by R8,
R8 is 1-4C-alkyl or 3-7C-cycloalkyl,
Y is phenyl, furanyl, thienyl, pyrrolyl, thiazolyl, oxazolyl, thiadiazolyl, oxadiazolyl, pyridinyl, pyrimidinyl, pyrazinyl or pyridazinyl, each of which is optionally substituted by R9,
R9 is 1-4C-alkyl, 1-4C-alkoxy or halogen,
R10 is hydrogen or 1-4C-alkyl,
or a pharmaceutically acceptable salt, tautomer, or stereoisomer of said compound, or a pharmaceutically acceptable salt of said tautomer or said stereoisomer.

3. The compound according to claim 1, wherein ring B and the imidazole to which it is fused form a

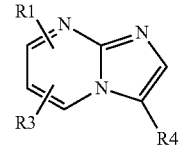

wherein
R1 is hydrogen, 1-4C-alkyl, halogen, amino, —SR2, trifluoromethyl, cyano, 3-7C-cycloalkyl, 2-4C-alkenyl, 2-4C-alkynyl, 1-4C-alkoxy, 3-7C-cycloalkoxy, mono- or di-1-4C-alkylamino, mono- or di-1-4C-alkylaminocarbonyl, —C(NH)NH2, —C(O)NH2 or —C(O)OR10

R2 is hydrogen, 1-4C-alkyl or 3-7C-cycloalkyl,
R3 is hydrogen, 1-4C-alkyl or halogen,
R4 is phenyl substituted by R5, unsubstituted phenyl, thienyl, pyridinyl, oxazolyl or thiazolyl,
R5 is 1-4C-alkyl, halogen or 1-4C-alkoxy,
R6 is hydrogen or methyl,
R7 is —W—Y,
W is 1,2,4-triazolylene, pyrazolylene, 1,2,4-oxadiazolylene or imidazolylene,
Y is phenyl, furan-2-yl, thien-2-yl, pyrrol-2-yl, pyridin-4-yl, thiazol-2-yl, thiazol-4-yl, oxazol-2-yl, oxazol-4-yl, 1,3,4-thiadiazol-2-yl, 1,3,4-oxadiazol-2-yl, pyridin-2-yl, pyrimidin-2-yl, pyrimidin-4-yl, pyrazin-2-yl or pyridazin-3-yl, each of which is optionally substituted by R9,
R9 is 1-4C-alkyl, 1-4C-alkoxy or halogen,
R10 is hydrogen or 1-4C-alkyl,
or a pharmaceutically acceptable salt, tautomer, or stereoisomer of said compound, or a pharmaceutically acceptable salt of said tautomer or said stereoisomer.

4. The compound according to claim 1, wherein ring B and the imidazole to which it is fused form a

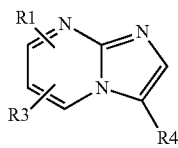

wherein
R1 is hydrogen, 1-4C-alkyl, halogen, —SR2, amino, trifluoromethyl, cyano, 2-4C-alkenyl, 2-4C-alkynyl, 1-4C-alkoxy, mono- or di-1-4C-alkylamino, mono- or di-1-4C-alkylaminocarbonyl, —C(NH)NH2, —C(O)NH2 or —C(O)OR10
R2 is 1-4C-alkyl,
R3 is hydrogen or halogen,
R4 is phenyl substituted by R5, unsubstituted phenyl, thienyl, pyridinyl, oxazolyl or thiazolyl,
R6 is hydrogen,
R7 is —W—Y,
W is 1,2,4-triazolylene, pyrazolylene or 1,2,4-oxadiazolylene,
Y is phenyl, furan-2-yl, thien-2-yl, pyrrol-2-yl, pyridin-4-yl, thiazol-2-yl, pyridin-2-yl, pyrimidin-2-yl, pyrimidin-4-yl, pyrazin-2-yl or pyridazin-3-yl, each of which is optionally substituted by R9,
R9 is 1-4C-alkyl, 1-4C-alkoxy or halogen,
R10 is hydrogen or 1-4C-alkyl,
or a pharmaceutically acceptable salt, tautomer, or stereoisomer of said compound, or a pharmaceutically acceptable salt of said tautomer or said stereoisomer.

5. A compound according to claim 1, selected from the group consisiting of
3-phenyl-2-(4-{[4-(5-pyridin-2-yl-1,2,4-triazol-3-yl)piperidin-1-yl]methyl}phenyl)imidazo[1,2-a]pyrimidine;
3-phenyl-2-(4-{[4-(3-pyrazin-2-yl-1,2,4-oxadiazol-5-yl)piperidin-1-yl]methyl}phenyl)imidazo[1,2-a]pyrimidine;
6-bromo-3-phenyl-2-(4-{[4-(5-pyridin-2-yl-1,2,4-triazol-3-yl)piperidin-1-yl]methyl}phenyl)imidazo[1,2-a]pyrimidine;
3-(4-fluorophenyl)-2-(4-{[4-(5-pyridin-2-yl-1,2,4-triazol-3-yl)piperidin-1-yl]methyl}phenyl)imidazo[1,2-a]pyrimidine;
7-methyl-3-phenyl-2-(4-{[4-(5-pyridin-2-yl-1,2,4-triazol-3-yl)piperidin-1-yl]methyl}phenyl)imidazo[1,2-a]pyrimidine;
3-(4-methoxyphenyl)-2-(4-{[4-(5-pyridin-2-yl-1,2,4-triazol-3yl)piperidin-1-yl]methyl}phenyl)imidazo[1,2-a]pyrimidine;
6-chloro-3-phenyl-2-(4-{[4-(5-pyridin-2-yl-1,2,4-triazol-3-yl)piperidin-1-yl]methyl}phenyl)imidazo[1,2-a]pyrimidine;
6-iodo-3-phenyl-2-(4-{[4-(5-pyridin-2-yl-1,2,4-triazol-3-yl)piperidin-1-yl]methyl}phenyl)imidazo[1,2-a]pyrimidine;
7-methoxy-3-phenyl-2-(4-{[4-(5-pyridin-2-yl-1,2,4-triazol-3-yl)pipendin-1-yl]methyl}phenyl)imidazo[1,2-a]pyrimidine;
3-phenyl-2-(4-{[4-(5-pyridin-2-yl-1,2,4-triazol-3-yl)pipendin-1-yl]methyl}phenyl)-7-(trifluoromethyl)imidazo[1,2-a]pyrimidine;
3-phenyl-2-(4-{[4-(3-pyridin-2-yl-pyrazol-5-yl)piperidin-1-yl]methyl}phenyl)imidazo[1,2-a]pyrimidine;
2-(4-{[4-(5-pyridin-2-yl-1,2,4-triazol-3-yl)piperidin-1-yl]methyl}phenyl)-3-(3-thienyl)imidazo[1,2-a]pyrimidine;
2-(4-{[4-(5-pyridin-2-yl-1,2,4-triazol-3-yl)piperidin-1-yl]methyl}phenyl)-3-(2-thienyl)imidazo[1,2-a]pyrimidine;
3-pyridin-4-yl-2-(4-{[4-(5-pyridin-2-yl-1,2,4-triazol-3-yl)piperidin-1-yl]methyl}phenyl)imidazo[1,2-a]pyrimidine;
2-(4-{[4-(5-pyridin-2-yl-1,2,4-triazol-3-yl)piperidin-1-yl]methyl}phenyl)-3-(1,3-thiazol-2-yl)imidazo[1,2-a]pyrimidine;
3-(2-fluorophenyl)-2-(4-{[4-(5-pyridin-2-yl-1,2,4-triazol-3-yl)piperidin-1-yl]methyl}phenyl)imidazo[1,2-a]pyrimidine
3-phenyl-2-(4-{[4-(5-pyridin-4-yl-1H-1,2,4-triazol-3-yl)piperidin-1-yl]methyl}phenyl)imidazo[1,2-a]pyrimidine;
2-[4-({4-[5-(6-methylpyridin-2-yl)-4H-1,2,4-triazol-3-yl]piperidin-1-yl}methyl)phenyl]-3-phenyl imidazo[1,2-a]pyrimidine;
2-[4-({4-5-(5-methylpyridin-2-yl)-4H-1,2,4-triazol-3-yl]piperidin-1-yl}methyl)phenyl]-3-phenylimidazo[1,2-a]pyrimidine;
2-[4-({4-[5-(5-chloropyridin-2-yl)-4H-1,2,4-triazol-3-yl]piperidin-1-yl}methyl)phenyl]-3-phenylimidazo[1,2-a]pyrimidine;
3-phenyl-2-(4-{[4-(5-pyrimidin-2-yl-1H-1,2,4-triazol-3-yl)piperidin-1-yl]methyl}phenyl)imidazo[1,2-a]pyrimidine;
3-phenyl-2-[4-({4-5-(1,3-thiazol-2-yl)-1H-1,2,4-triazol-3-yl]piperidin-1-yl}methyl)phenyl]imidazo[1,2-a]pyrimidine;
2-[4-({4-[5-(2-furyl)-4H-1,2,4-triazol-3-yl]piperidin-1-yl}methyl)phenyl]-3-phenylimidazo[1,2-a]pyrimidine;
3-phenyl-2-[4-({4-[5-(1H-pyrrol-2-yl)-4H-1,2,4-triazol-3-yl]piperidin-1-yl}methyl)phenyl]imidazo[1,2-a]pyrimidine;
3-phenyl-2-(4-{[4-(5-pyridin-2-yl-1,2,4-oxadiazol-3-yl)piperidin-1-yl]methyl}phenyl)imidazo[1,2-a]pyrimidine; and 3-phenyl-2-(4-{[4-(5-phenyl-4H-1,2,4-triazol-3-yl)piperidin-1-yl]methyl}phenyl)imidazo[1,2-a]pyrimidine;

or a pharmaceutically acceptable salt, tautomer, or stereoisomer of said compound, or a pharmaceutically acceptable salt of said tautomer or said stereoisomer.

6. A pharmaceutical composition comprising at least one compound, tautomer of said compound or stereoisomer of said compound, or a pharmaceutically acceptable salt of said compound, tautomer or stereoisomer according to claim 1, together with at least one pharmaceutically acceptable auxiliary.

7. A pharmaceutical composition according to claim 6, further comprising one or more chemotherapeutic anti-cancer agents or target-specific anti-cancer agents.

8. A method for the treatment or amelioration of breast cancer comprising administering to a patient in need thereof a compound, or a tautomer of said compound, or a stereoisomer of said compound or a pharmaceutically acceptable salt of said compound, tautomer or stereoisomer according to claim 1.

9. A method for the treatment or amelioration of breast cancer comprising administering to a patient in need thereof a compound, or a tautomer of said compound, or a stereoisomer of said compound or a pharmaceutically acceptable salt of said compound, tautomer or stereoisomer according to claim 2.

10. A method for the treatment or amelioration of breast cancer comprising administering to a patient in need thereof a compound, or a tautomer of said compound, or a stereoisomer of said compound or a pharmaceutically acceptable salt of said compound, tautomer or stereoisomer according to claim 3.

11. A method for the treatment or amelioration of breast cancer comprising administering to a patient in need thereof a compound, or a tautomer of said compound, or a stereoisomer of said compound or a pharmaceutically acceptable salt of said compound, tautomer or stereoisomer according to claim 4.

12. A method for the treatment or amelioration of breast cancer comprising administering to a patient in need thereof a compound, or a tautomer of said compound, or a stereoisomer of said compound or a pharmaceutically acceptable salt of said compound, tautomer or stereoisomer according to claim 5.

* * * * *